US011136324B2

(12) United States Patent
Gao et al.

(10) Patent No.: US 11,136,324 B2
(45) Date of Patent: Oct. 5, 2021

(54) SUBSTITUTED IMIDAZOLES AS APOPTOSIS SIGNAL REGULATING KINASE 1 INHIBITORS

(71) Applicants: Jiangsu Hansoh Pharmaceutical Group Co., Ltd., Jiangsu (CN); Shanghai Hansoh Biomedical Co., Ltd., Shanghai (CN)

(72) Inventors: Peng Gao, Jiangsu (CN); Guangjun Sun, Jiangsu (CN); Shaobao Wang, Jiangsu (CN); Fujun Zhang, Jiangsu (CN); Lei Liu, Jiangsu (CN); Rudi Bao, Jiangsu (CN)

(73) Assignees: Jiangsu Hansoh Pharmaceutical Group Co., Ltd., Lianyungang (CN); Shanghai Hansoh Biomedical Co., Ltd., Shanghai (CN)

( * ) Notice: Subject to any disclaimer, the term of this patent is extended or adjusted under 35 U.S.C. 154(b) by 16 days.

(21) Appl. No.: 16/490,157

(22) PCT Filed: Mar. 2, 2018

(86) PCT No.: PCT/CN2018/077869
§ 371 (c)(1),
(2) Date: Aug. 30, 2019

(87) PCT Pub. No.: WO2018/157856
PCT Pub. Date: Sep. 7, 2018

(65) Prior Publication Data
US 2021/0032249 A1 Feb. 4, 2021

(30) Foreign Application Priority Data

Mar. 3, 2017 (CN) .......................... 201710123799.7
Aug. 18, 2017 (CN) .......................... 201710713967.8
Jan. 17, 2018 (CN) .......................... 201810045023.2

(51) Int. Cl.
*A61K 31/4178* (2006.01)
*C07D 233/54* (2006.01)
*C07D 487/04* (2006.01)
*C07D 498/04* (2006.01)

(52) U.S. Cl.
CPC ......... *C07D 487/04* (2013.01); *C07D 498/04* (2013.01)

(58) Field of Classification Search
CPC .......................... A61K 31/4178; C07D 233/54
USPC ....................................... 514/397; 548/335.1
See application file for complete search history.

(56) References Cited

U.S. PATENT DOCUMENTS

2010/0029619 A1   2/2010 Uchikawa et al.

FOREIGN PATENT DOCUMENTS

| CN | 102482257 A | 5/2012 | |
|---|---|---|---|
| CN | 102985418 A | 3/2013 | |
| CN | 104080771 A | 10/2014 | |
| CN | 104918936 A | 9/2015 | |
| CN | 105980382 A | 9/2016 | |
| EP | 1724262 B1 | 5/2012 | |
| WO | 2008008375 A2 | 1/2008 | |
| WO | 2011008709 A1 | 1/2011 | |
| WO | 2012003387 A1 | 1/2012 | |
| WO | 2016025474 A1 | 2/2016 | |
| WO | 2016105453 A1 | 6/2016 | |
| WO | 2016106384 A1 | 6/2016 | |
| WO | WO-2018151830 A1 * | 8/2018 | ........... C07D 471/04 |

OTHER PUBLICATIONS

Rong et al, "Synthesis of Gamma-Lactams by Mild, o-Benzoquinone-Induced Oxidation of Pyrrolidines Containing Oxidation-Sensitive Functional Groups," The Journal of Organic Chemistry, vol. 82, pp. 532-540 (2017).
Hoye et al, "Total Synthesis of (−)-Sessilifoliamide C and (−)-8-epi-Stemoamide," Organic Letters, vol. 13, No. 10, pp. 2634-2637 (2011).
Int'l Search Report dated May 25, 2018 in Int'l Application No. PCT/CN2018/077869.
Registry 1518316-27-2/RN, 1508008-76-1/RN, 1506777-35-0/RN STN (Jan. 13, 2014).

* cited by examiner

*Primary Examiner* — Douglas M Willis
(74) *Attorney, Agent, or Firm* — Ice Miller LLP

(57) ABSTRACT

An amide derivative inhibitor and a preparation method and an application thereof. Specifically relating to the compound shown in general formula (I), a preparation method for same, a pharmaceutical composition comprising said compound, and an application of same as an ASK inhibitor for the treatment of neurodegenerative disease, cardiovascular disease, inflammation, autoimmune and metabolic disease, each of the substituents in the general formula (I) being as defined in the description.

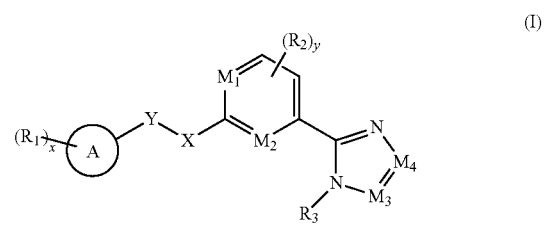

18 Claims, No Drawings

SUBSTITUTED IMIDAZOLES AS APOPTOSIS SIGNAL REGULATING KINASE 1 INHIBITORS

CROSS-REFERENCE TO RELATED APPLICATION

This application is a Section 371 of International Application No. PCT/CN2018/077869, filed Mar. 2, 2018, which was published in the Chinese language on Sep. 7, 2018, under International Publication No. WO 2018/157856 A1, which claims priority under 35 U.S.C. § 119(b) to Chinese Application No. 201710123799.7, filed Mar. 3, 2017, Chinese Application No. 201710713967.8, filed Aug. 18, 2017 and Chinese Application No. 201810045023.2, filed Jan. 17, 2018, the disclosures of which are incorporated herein by reference in their entirety.

FIELD OF THE INVENTION

The present invention belongs to the field of drug synthesis, and in particular relates to an amide derivative inhibitor, a method for preparing the same, and a use thereof.

BACKGROUND OF THE INVENTION

Mitogen-activated protein kinase (MAPK) signaling pathway mediates a variety of cellular functions, including cell growth, differentiation, inflammation, survival, and apoptosis, and is a key signaling pathway for cell mitosis and apoptosis. MAPK is classified into three major types, namely mitogen-activated protein kinase kinase kinase (MAP3K), mitogen-activated protein kinase kinase (MAP2K) and mitogen-activated protein kinase (MAPK). MAP3K is activated by environmental signal stimulation, and then activates MAP2K. MAP2K further activates MAPK, which mediates the corresponding cellular effects by the phosphorylation of its downstream substrates such as transcription factors and the like.

Apoptosis signal regulating kinase 1 (ASK1), also known as mitogen-activated protein kinase kinase kinase 5 (MAP3K5), is a member of the MAPK family and mediates MAPK signaling pathway activation. ASK1 can be activated by autophosphorylation under stress conditions including oxidative stress, endoplasmic reticulum stress and calcium influx, thereby activating its downstream MAP2K (such as MKK3/6 and MKK4/7), and further activating c-Jun N-terminal kinase (JNK) and p38 mitogen-activated protein kinase, leading to corresponding cellular effects such as apoptosis and the like. ASK1 activation and its signaling pathway play an important role in neurodegenerative diseases, cardiovascular diseases, inflammation, autoimmune and metabolic diseases.

The incidence of non-alcoholic steatohepatitis (NASH) is high, with approximately 2% to 5% of NASH patients worldwide or domestically. The market size of NASH is expected to reach $35 billion to $40 billion by 2025. At present, there are no drugs approved for treating NASH. The targets for treating NASH in preliminary development include FXR, PPAR, GLP and the like. However, the targets FXR and PPAR have many safety issues. GLP is a target for preliminary diabetes treatment, the efficacy of which has not been verified by exact clinical endpoint, and the drugs targeting GLP belong to peptide drugs, which need to be administrated subcutaneously every day. ASK1 is becoming a new mechanism and a new target in the field of NASH treatment. Its signaling pathway plays an important role in the occurrence and development of NASH by promoting liver tissue inflammation and fibrosis. ASK1 inhibitors have great potential for the clinical treatment of NASH, and have potential valuable application in the treatment of other diseases including neurodegenerative diseases, cardiovascular diseases, inflammation, autoimmune metabolic diseases and the like.

Patent applications that disclose selective ASK1 inhibitors include WO2011008709, WO2016025474, WO2012003387, WO2016105453, WO2016106384, WO2008008375 and the like.

ASK1 inhibitor as a drug has a good application prospect in the pharmaceutical industry. The present invention will provide a novel structure of a selective ASK1 inhibitor, and finds that the compounds having such a structure exhibit an excellent efficacy and effect.

SUMMARY OF THE INVENTION

The objective of the present invention is to provide a compound of formula (I), a stereoisomer thereof, or a pharmaceutically acceptable salt thereof, wherein the structure of the compound of formula (I) is as follows:

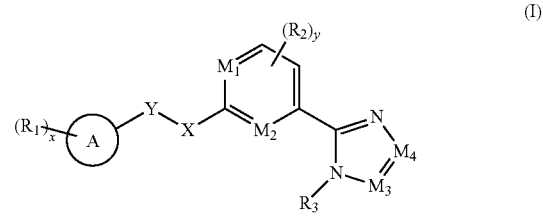

wherein:

$M_1$, $M_2$, $M_3$ and $M_4$ are each independently selected from the group consisting of N and —$CR_6$;

X and Y are each independently selected from the group consisting of a bond,

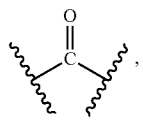

—$NR_7$—, —$CR_7R_8$—, —$S(O)_m$—,

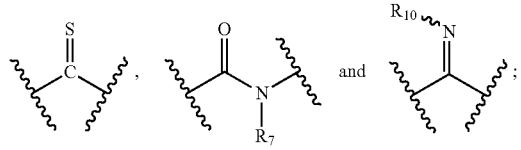

ring A is selected from the group consisting of aryl and heteroaryl, wherein the aryl and heteroaryl are each optionally further substituted by one or more substituents selected from the group consisting of deuterium, alkyl, deuterated alkyl, halogen, amino, nitro, hydroxy, cyano, alkoxy, hydroxyalkyl, cycloalkyl, heterocyclyl, aryl, heteroaryl, —$(CH_2)_nOR_9$, —$(CH_2)_nSR_9$, —$(CH_2)_nC(O)R_9$, —$(CH_2)_nC(O)OR_9$, —$(CH_2)_nS(O)_mR_9$, —$(CH_2)_nNR_{10}R_{11}$, —$(CH_2)_nC(O)NR_{10}R_{11}$, —$(CH_2)_nC(O)NHR_{10}$, —$(CH_2)_nNR_{10}C(O)R_9$ and —$(CH_2)_nNR_{10}S(O)_mR_9$;

each $R_1$ is identical or different and each is independently selected from the group consisting of hydrogen, deuterium, alkyl, deuterated alkyl, haloalkyl, alkoxy, haloalkoxy, halogen, amino, nitro, hydroxy, cyano, cycloalkyl, heterocyclyl, aryl, heteroaryl, $-(CH_2)_nOR_9$, $-(CH_2)_nSR_9$, $-(CH_2)_nC(O)R_9$, $-(CH_2)_nC(O)OR_9$, $-(CH_2)_nS(O)_mR_9$, $-(CH_2)_nNR_{10}R_{11}$, $-(CH_2)_nC(O)NR_{10}R_{11}$, $-(CH_2)_nC(O)NHR_{10}$, $-(CH_2)_nNR_{10}C(O)R_9$ and $-(CH_2)_nNR_{10}S(O)_mR_9$, wherein the alkyl, haloalkyl, cycloalkyl, heterocyclyl, aryl and heteroaryl are each optionally further substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl, heteroaryl, $-(CH_2)_nOR_{12}$, $-(CH_2)_nSR_{12}$, $-(CH_2)_nC(O)R_{12}$, $-(CH_2)_nC(O)OR_{12}$, $-(CH_2)_nS(O)_mR_{12}$, $-(CH_2)_nNR_{12}R_{13}$, $-(CH_2)_nC(O)NR_{12}R_{13}$, $-(CH_2)_nC(O)NHR_{13}$, $-(CH_2)_nNR_{13}C(O)R_{12}$ and $-(CH_2)_nNR_{13}S(O)_mR_{12}$;

each $R_2$ is identical or different and each is independently selected from the group consisting of hydrogen, deuterium, alkyl, deuterated alkyl, haloalkyl, alkoxy, haloalkoxy, halogen, amino, nitro, hydroxy, cyano, cycloalkyl, heterocyclyl, aryl, heteroaryl, $-(CH_2)_nOR_9$, $-(CH_2)_nSR_9$, $-(CH_2)_nC(O)R_9$, $-(CH_2)_nC(O)OR_9$, $-(CH_2)_nS(O)_mR_9$, $-(CH_2)_nNR_{10}R_{11}$, $-(CH_2)_nC(O)NR_{10}R_{11}$, $-(CH_2)_nC(O)NHR_{10}$, $-(CH_2)_nNR_{10}C(O)R_9$ and $-(CH_2)_nNR_{10}S(O)_mR_9$;

$R_3$ is selected from the group consisting of hydrogen, deuterium, alkyl, deuterated alkyl, haloalkyl, hydroxy, amino, cycloalkyl, heterocyclyl, aryl and heteroaryl, wherein the alkyl, haloalkyl, cycloalkyl, heterocyclyl, aryl and heteroaryl are each optionally further substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl, heteroaryl, $-(CH_2)_nOR_9$, $-(CH_2)_nSR_9$, $-(CH_2)_nC(O)R_9$, $-(CH_2)_nC(O)OR_9$, $-(CH_2)_nS(O)_mR_9$, $-(CH_2)_nNR_{10}R_{11}$, $-(CH_2)_nC(O)NR_{10}R_{11}$, $-(CH_2)_nC(O)NHR_{10}$, $-(CH_2)_nNR_{10}C(O)R_9$ and $-(CH_2)_nNR_{10}S(O)_mR_9$;

or, $R_3$ and $M_3$, $M_3$ and $M_4$ are bonded to form a cycloalkyl, heterocyclyl, aryl or heteroaryl, respectively, wherein the cycloalkyl, heterocyclyl, aryl or heteroaryl is optionally further substituted by one or more substituents selected from the group consisting of deuterium, alkyl, deuterated alkyl, haloalkyl, halogen, amino, nitro, hydroxy, cyano, alkenyl, alkynyl, alkoxy, hydroxyalkyl, cycloalkyl, heterocyclyl, aryl, heteroaryl, $-(CR_9R_{10})_n-$, $-(CH_2)_nOR_9$, $-(CH_2)_nSR_9$, $-(CH_2)_nC(O)R_9$, $-(CH_2)_nC(O)OR_9$, $-(CH_2)_nS(O)_mR_9$, $-(CH_2)_nNR_{10}R_{11}$, $-(CH_2)_nC(O)NR_{10}R_{11}$, $-(CH_2)_nC(O)NHR_{10}$, $-(CH_2)_nNR_{10}C(O)R_9$ and $-(CH_2)_nNR_{10}S(O)_mR_9$;

or, $R_1$ and X or Y, $M_1$ and X or Y are bonded to form a cycloalkyl, heterocyclyl, aryl or heteroaryl, respectively, wherein the cycloalkyl, heterocyclyl, aryl or heteroaryl is optionally further substituted by one or more substituents selected from the group consisting of deuterium, alkyl, deuterated alkyl, haloalkyl, halogen, amino, nitro, hydroxy, cyano, alkenyl, alkynyl, alkoxy, hydroxyalkyl, cycloalkyl, heterocyclyl, aryl, heteroaryl, $-(CR_9R_{10})_n-$, $-(CH_2)_nOR_9$, $-(CH_2)_nSR_9$, $-(CH_2)_nC(O)R_9$, $-(CH_2)_nC(O)OR_9$, $-(CH_2)_nS(O)_mR_9$, $-(CH_2)_nNR_{10}R_{11}$, $-(CH_2)_nC(O)NR_{10}R_{11}$, $-(CH_2)_nC(O)NHR_{10}$, $-(CH_2)_nNR_{10}C(O)R_9$ and $-(CH_2)_nNR_{10}S(O)_mR_9$;

$R_6$, $R_7$ and $R_8$ are identical or different and are each independently selected from the group consisting of hydrogen, deuterium, alkyl, deuterated alkyl, haloalkyl, alkoxy, haloalkoxy, halogen, amino, nitro, hydroxy, cyano, cycloalkyl, heterocyclyl, aryl, heteroaryl, $-(CH_2)_nOR_9$, $-(CH_2)_nSR_9$, $-(CH_2)_nC(O)R_9$, $-(CH_2)_nC(O)OR_9$, $-(CH_2)_nS(O)_mR_9$, $-(CH_2)_nNR_{10}R_{11}$, $-(CH_2)_nC(O)NR_{10}R_{11}$, $-(CH_2)_nC(O)NHR_{10}$, $-(CH_2)_nNR_{10}C(O)R_9$ and $-(CH_2)_nNR_{10}S(O)_mR_9$, wherein the alkyl, haloalkyl, cycloalkyl, heterocyclyl, aryl and heteroaryl are each optionally further substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl, heteroaryl, $-(CH_2)_nOR_{12}$, $-(CH_2)_nSR_{12}$, $-(CH_2)_nC(O)R_{12}$, $-(CH_2)_nC(O)OR_{12}$, $-(CH_2)_nS(O)_mR_{12}$, $-(CH_2)_nNR_{12}R_{13}$, $-(CH_2)_nC(O)NR_{12}R_{13}$, $-(CH_2)_nC(O)NHR_{13}$, $-(CH_2)_nNR_{13}C(O)R_{12}$ and $-(CH_2)_nNR_{13}S(O)_mR_{12}$;

$R_9$ is selected from the group consisting of hydrogen, deuterium, alkyl, deuterated alkyl, haloalkyl, hydroxy, amino, alkoxy, haloalkoxy, cycloalkyl, heterocyclyl, aryl and heteroaryl, wherein the alkyl, haloalkyl, cycloalkyl, heterocyclyl, aryl and heteroaryl are each optionally further substituted by one or more substituents selected from the group consisting of deuterium, alkyl, halogen, amino, nitro, cyano, hydroxy, hydroxyalkyl, alkoxy, cycloalkyl, heterocyclyl, aryl, heteroaryl, $-(CH_2)_nOR_{12}$, $-(CH_2)_nSR_{12}$, $-(CH_2)_nC(O)R_{12}$, $-(CH_2)_nC(O)OR_{12}$, $-(CH_2)_nS(O)_mR_{12}$, $-(CH_2)_nNR_{12}R_{13}$, $-(CH_2)_nC(O)NR_{12}R_{13}$, $-(CH_2)_nC(O)NHR_{13}$, $-(CH_2)_nNR_{13}C(O)R_{12}$ and $-(CH_2)_nNR_{13}S(O)_mR_{12}$;

$R_{10}$ and $R_{11}$ are identical or different and are each independently selected from the group consisting of hydrogen, deuterium, alkyl, deuterated alkyl, haloalkyl, hydroxy, amino, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium, alkyl, halogen, hydroxy, amino, nitro, cyano, alkoxy, hydroxyalkyl, cycloalkyl, heterocyclyl, aryl, heteroaryl, $-(CH_2)_nOR_{12}$, $-(CH_2)_nSR_{12}$, $-(CH_2)_nC(O)R_{12}$, $-(CH_2)_nC(O)OR_{12}$, $-(CH_2)_nS(O)_mR_{12}$, $-(CH_2)_nNR_{12}R_{13}$, $-(CH_2)_nC(O)NR_{12}R_{13}$, $-(CH_2)_nC(O)NHR_{13}$, $-(CH_2)_nNR_{13}C(O)R_{12}$ and $-(CH_2)_nNR_{13}S(O)_mR_{12}$;

$R_{12}$ and $R_{13}$ are identical or different and are each independently selected from the group consisting of hydrogen, deuterium, alkyl, deuterated alkyl, haloalkyl, hydroxy, amino, ester group, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium, alkyl, halogen, hydroxy, amino, nitro, cyano, ester group, alkoxy, hydroxyalkyl, cycloalkyl, heterocyclyl, aryl and heteroaryl;

x is an integer of 0, 1, 2, 3 or 4;
y is an integer of 0, 1 or 2;
m is an integer of 0, 1 or 2; and
n is an integer of 0, 1, 2, 3, 4 or 5.

In a preferred embodiment of the present invention, the compound of formula (I) is a compound of formula (II), a stereoisomer thereof, or a pharmaceutically acceptable salt thereof:

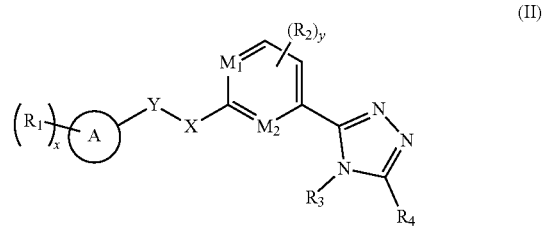

wherein:

$R_4$ is selected from the group consisting of hydrogen, deuterium, alkyl, deuterated alkyl, haloalkyl, alkoxy, haloalkoxy, halogen, amino, nitro, hydroxy, cyano, cycloalkyl, heterocyclyl, aryl, heteroaryl, —$(CH_2)_nOR_9$, —$(CH_2)_nSR_9$, —$(CH_2)_nC(O)R_9$, —$(CH_2)_nC(O)OR_9$, —$(CH_2)_nS(O)_mR_9$, —$(CH_2)_nNR_{10}R_{11}$, —$(CH_2)_nC(O)NR_{10}R_{11}$, —$(CH_2)_nC(O)NHR_{10}$, —$(CH_2)_nNR_{10}C(O)R_9$ and —$(CH_2)_nNR_{10}S(O)_mR_9$, wherein the alkyl, haloalkyl, cycloalkyl, heterocyclyl, aryl and heteroaryl are each optionally further substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl, heteroaryl, —$(CH_2)_nOR_{12}$, —$(CH_2)_nSR_{12}$, —$(CH_2)_nC(O)R_{12}$, —$(CH_2)_nC(O)OR_{12}$, —$(CH_2)_nS(O)_mR_{12}$, —$(CH_2)_nNR_{12}R_{13}$, —$(CH_2)_nC(O)NR_{12}R_{13}$, —$(CH_2)_nC(O)NHR_{13}$, —$(CH_2)_nNR_{13}C(O)R_{12}$ and —$(CH_2)_nNR_{13}S(O)_mR_{12}$;

$R_3$ and $R_4$ are bonded to form a heterocyclyl or heteroaryl, wherein the heterocyclyl or heteroaryl is optionally further substituted by one or more substituents selected from the group consisting of deuterium, alkyl, deuterated alkyl, haloalkyl, halogen, amino, nitro, hydroxy, cyano, alkenyl, alkynyl, alkoxy, hydroxyalkyl, cycloalkyl, heterocyclyl, aryl, heteroaryl, —$(CR_9R_{10})_n$—, —$(CH_2)_nOR_9$, —$(CH_2)_nSR_9$, —$(CH_2)_nC(O)R_9$, —$(CH_2)_nC(O)OR_9$, —$(CH_2)_nS(O)_mR_9$, —$(CH_2)_nNR_{10}R_{11}$, —$(CH_2)_nC(O)NR_{10}R_{11}$, —$(CH_2)_nC(O)NHR_{10}$, —$(CH_2)_nNR_{10}C(O)Rd$ and —$(CH_2)_nNR_{10}S(O)_mR_9$;

or, $R_3$ and $R_4$ are bonded to form a heterocyclyl or heteroaryl, any two substituents on the heterocyclyl or heteroaryl can form a cycloalkyl, heterocyclyl, aryl or heteroaryl, wherein the cycloalkyl, aryl, heterocyclyl or heteroaryl is optionally further substituted by one or more substituents selected from the group consisting of deuterium, alkyl, deuterated alkyl, haloalkyl, halogen, amino, nitro, hydroxy, cyano, alkenyl, alkynyl, alkoxy, hydroxyalkyl, cycloalkyl, heterocyclyl, aryl, heteroaryl, —$(CR_9R_{10})_n$—, —$(CH_2)_nOR_9$, —$(CH_2)_nSR_9$, —$(CH_2)_nC(O)R_9$, —$(CH_2)_nC(O)OR_9$, —$(CH_2)_nS(O)_mR_9$, —$(CH_2)_nNR_{10}R_{11}$, —$(CH_2)_nC(O)NR_{10}R_{11}$, —$(CH_2)_nC(O)NHR_{10}$, —$(CH_2)_nNR_{10}C(O)R_9$ and —$(CH_2)_nNR_{10}S(O)_mR_9$;

ring A, $M_1$, $M_2$, X, Y, $R_1$ to $R_3$, x, y, m and n are as defined in formula (I).

In a preferred embodiment of the present invention, the compound of formula (I) is a compound of formula (III), a stereoisomer thereof, or a pharmaceutically acceptable salt thereof:

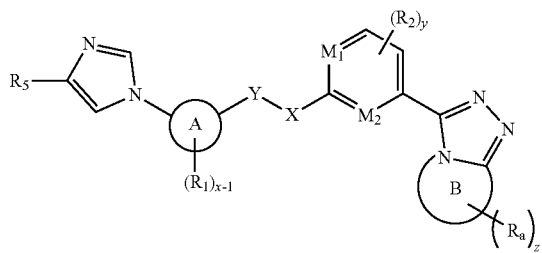

(III)

wherein:

ring B is selected from the group consisting of heterocyclyl and heteroaryl;

$R_5$ is selected from the group consisting of hydrogen, alkyl, deuterated alkyl, haloalkyl, alkoxy, haloalkoxy, halogen, amino, nitro, hydroxy, hydroxyalkyl, cyano, cycloalkyl, heterocyclyl, aryl, heteroaryl, —$(CH_2)_nOR_9$, —$(CH_2)_nSR_9$, —$(CH_2)_nC(O)R_9$, —$(CH_2)_nC(O)OR_9$, —$(CH_2)_nS(O)_mR_9$, —$(CH_2)_nNR_{10}R_{11}$, —$(CH_2)_nC(O)NR_{10}R_{11}$, —$(CH_2)_nC(O)NHR_{10}$, —$(CH_2)_nNR_{10}C(O)R_9$ and —$(CH_2)_nNR_{10}S(O)_mR_9$, wherein the alkyl, haloalkyl, cycloalkyl, heterocyclyl, aryl and heteroaryl are each optionally further substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl, heteroaryl, —$(CH_2)_nOR_{12}$, —$(CH_2)_nSR_{12}$, —$(CH_2)_nC(O)R_{12}$, —$(CH_2)_nC(O)OR_{12}$, —$(CH_2)_nS(O)_mR_{12}$, —$(CH_2)_nNR_{12}R_{13}$, —$(CH_2)_nC(O)NR_{12}R_{13}$, —$(CH_2)_nC(O)NHR_{13}$, —$(CH_2)_nNR_{13}C(O)R_{12}$ and —$(CH_2)_nNR_{13}S(O)_mR_{12}$; and preferably cyclopropyl;

$R_a$ is selected from the group consisting of hydrogen, deuterium, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CR_9R_{10})_n$—, —$(CH_2)_nOR_9$, —$(CH_2)_nSR_9$, —$(CH_2)_nC(O)R_9$, —$(CH_2)_nC(O)OR_9$, —$(CH_2)_nS(O)_mR_9$, —$(CH_2)_nNR_{10}R_{11}$, —$(CH_2)_nC(O)NR_{10}R_{11}$, —$(CH_2)_nC(O)NHR_{10}$, —$(CH_2)_nNR_{10}C(O)R_9$ and —$(CH_2)_nNR_{10}S(O)_mR_9$, wherein the alkyl, alkenyl, alkynyl, haloalkyl, cycloalkyl, heterocyclyl, aryl and heteroaryl are each optionally further substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl, heteroaryl, —$(CH_2)_nOR_{12}$, —$(CH_2)_nSR_{12}$, —$(CH_2)_nC(O)R_{12}$, —$(CH_2)_nC(O)OR_{12}$, —$(CH_2)_nS(O)_mR_{12}$, —$(CH_2)_nNR_{12}R_{13}$, —$(CH_2)_nC(O)NR_{12}R_{13}$, —$(CH_2)_nC(O)NHR_{13}$, —$(CH_2)_nNR_{13}C(O)R_{12}$ and —$(CH_2)_nNR_{13}S(O)_mR_{12}$; and preferably $C_{1-8}$ alkyl, $C_{1-8}$ alkoxy, $C_{1-8}$ cycloalkyl;

or, any two $R_a$ on ring B can form a new cycloalkyl, heterocyclyl, aryl and heteroaryl, wherein the newly formed cycloalkyl, aryl, heterocyclyl or heteroaryl is optionally further substituted by one or more substituents selected from the group consisting of hydrogen, deuterium, alkyl, deuterated alkyl, haloalkyl, halogen, amino, nitro, hydroxy, cyano, alkoxy, hydroxyalkyl, cycloalkyl, heterocyclyl, aryl, heteroaryl, —$(CR_9R_{10})_n$—, —$(CH_2)_nOR_9$, —$(CH_2)_nSR_9$, —$(CH_2)_nC(O)R_9$, —$(CH_2)_nC(O)OR_9$, —$(CH_2)_nS(O)_mR_9$, —$(CH_2)_nNR_{10}R_{11}$, —$(CH_2)_nC(O)NR_{10}R_{11}$, —$(CH_2)_nC(O)NHR_{10}$, —$(CH_2)_nNR_{10}C(O)R_9$ and —$(CH_2)_nNR_{10}S(O)_mR_9$;

x–1 is an integer of 1, 2, 3 or 4; and z is an integer of 0, 1, 2, 3, 4 or 5;

ring A, $M_1$, $M_2$, X, Y, $R_1$ to $R_5$, x, y, m and n are as defined in formula (I).

In a preferred embodiment of the present invention, the compound of formula (I) is a compound of formula (IV), a stereoisomer thereof, or a pharmaceutically acceptable salt thereof:

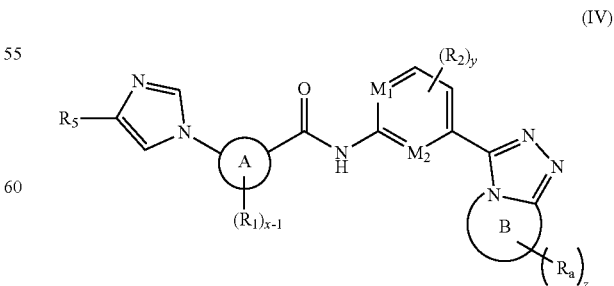

(IV)

wherein: ring A, ring B, $M_1$, $M_2$, $R_1$, $R_2$, $R_5$, $R_a$, x–1, y and z are as defined in formula (I).

In a preferred embodiment of the present invention, the compound of formula (I) is a compound of formula (V), a stereoisomer thereof, or a pharmaceutically acceptable salt thereof:

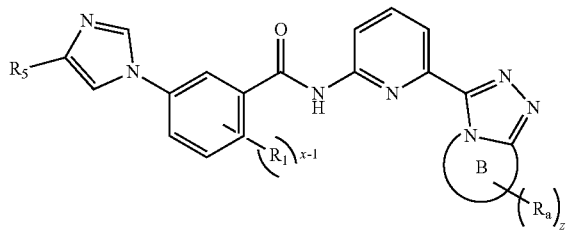

(V)

wherein:
ring B, $R_1$, $R_5$, $R_a$, x-1 and z are as defined in formula (I).

In a preferred embodiment of the present invention, the compound of formula (I) is a compound of formula (VI-A), a stereoisomer thereof, or a pharmaceutically acceptable salt thereof:

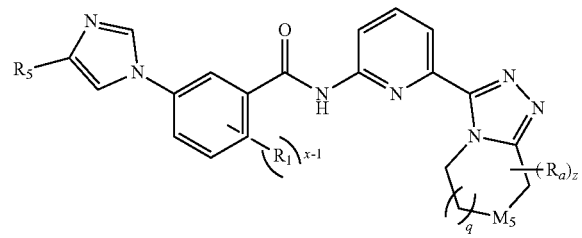

(VI-A)

wherein:
$M_5$ is O, —$CR_6$ or —$NR_7$;
$R_1$ is selected from the group consisting of hydrogen, $C_{1-8}$ alkyl and halogen;
$R_5$ is selected from the group consisting of $C_{1-8}$ alkyl, $C_{3-8}$ cycloalkyl, $C_{1-8}$ haloalkyl, $C_{1-8}$ hydroxyalkyl and 3 to 6 membered heterocyclyl;
each $R_a$ is identical or different and each is independently selected from the group consisting of hydrogen, cyano, $C_{1-8}$ alkyl, $C_{2-8}$ alkenyl, $C_{2-8}$ alkynyl, $C_{1-8}$ haloalkyl, $C_{1-8}$ hydroxyalkyl, $C_{1-8}$ alkoxy, $C_{3-8}$ cycloalkyl, —$(CH_2)_nOR_9$, —$(CR_9R_{10})_n$— and —$(CH_2)_nC(O)R_9$, wherein the $C_{1-8}$ alkyl, $C_{2-8}$ alkenyl, $C_{2-8}$ alkynyl, $C_{1-8}$ haloalkyl, $C_{1-8}$ hydroxyalkyl, $C_{1-8}$ alkoxy and $C_{3-8}$ cycloalkyl are each optionally further substituted by one or more substituents selected from the group consisting of hydrogen, deuterium, halogen, cyano, hydroxy, $C_{1-8}$ alkyl, $C_{1-8}$ hydroxyalkyl and $C_{1-8}$ alkoxy; or, any two $R_a$ form a $C_{3-8}$ cycloalkyl or $C_{3-8}$ heterocyclyl;
$R_9$ and $R_{10}$ are identical or different and are each independently selected from the group consisting of hydrogen, $C_{1-8}$ alkyl, $C_{1-8}$ haloalkyl, $C_{1-8}$ hydroxyalkyl and $C_{1-8}$ alkoxy;
x-1 is an integer of 1, 2, 3 or 4;
q is 0, 1 or 2; and
z is an integer of 0, 1, 2, 3, 4 or 5.

In a preferred embodiment of the present invention, the compound of formula (I) is a compound of formula (VI), a stereoisomer thereof, or a pharmaceutically acceptable salt thereof:

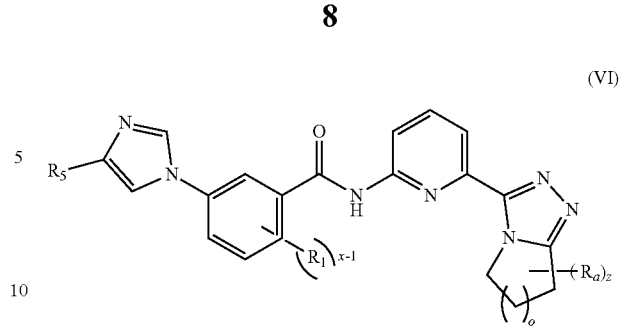

(VI)

o is an integer of 0, 1, 2, 3, 4 or 5; and
$R_1$, $R_5$, $R_a$, x and z are as defined in formula (VI).

In a preferred embodiment of the present invention, the compound of formula (I) is a compound of formula (VII), a stereoisomer thereof, or a pharmaceutically acceptable salt thereof:

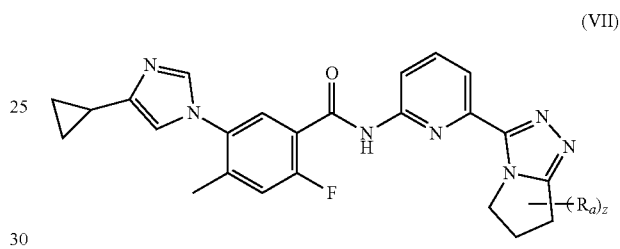

(VII)

wherein:
each $R_a$ is identical or different and each is independently selected from the group consisting of hydrogen, cyano, $C_{1-6}$ alkyl, $C_{2-6}$ alkenyl, $C_{2-6}$ alkynyl, $C_{1-6}$ haloalkyl, $C_{1-6}$ alkoxy, $C_{3-6}$ cycloalkyl, —$(CH_2)_nOR_9$ and —$(CR_9R_{10})_n$—, wherein the $C_{1-6}$ alkyl, $C_{2-6}$ alkenyl, $C_{2-6}$ alkynyl, $C_{1-6}$ haloalkyl, $C_{1-6}$ alkoxy and $C_{3-6}$ cycloalkyl are each optionally further substituted by one or more substituents selected from the group consisting of hydrogen, halogen, cyano, hydroxy, $C_{1-6}$ alkyl and $C_{1-6}$ alkoxy; or, any two $R_a$ can form a 3 to 6 membered cycloalkyl, and
z is an integer of 0, 1, 2 or 3.

In a preferred embodiment of the present invention, the compound of formula (I) is a compound of formula (VIII), a stereoisomer thereof, or a pharmaceutically acceptable salt thereof:

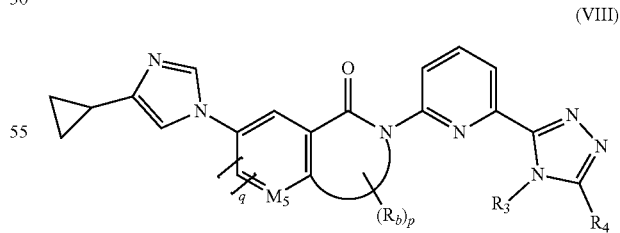

(VIII)

wherein:
$M_5$ is selected from the group consisting of S and CH;
$R_3$ is selected from the group consisting of $C_{1-8}$ alkyl, $C_{1-8}$ deuterated alkyl, $C_{1-8}$ alkoxy, $C_{1-8}$ haloalkoxy, $C_{3-8}$ cycloalkyl and 3 to 10 membered heterocyclyl, wherein the $C_{1-8}$ alkyl, $C_{1-8}$ deuterated alkyl, $C_{1-8}$ alkoxy, $C_{1-8}$ haloalkoxy, $C_{3-8}$ cycloalkyl and 3 to 10 membered heterocyclyl are each optionally further substituted by one or more substituents selected from the group consisting of hydrogen, deuterium, $C_{1-8}$ alkyl, $C_{1-8}$ deuterated alkyl, $C_{1-8}$ haloalkyl, halogen, amino, hydroxy, cyano, $C_{1-8}$ alkoxy, $C_{1-8}$ hydroxyalkyl, $C_{3-8}$ cycloalkyl, 3 to 10 membered heterocyclyl, 6 to 10 membered aryl and 5 to 10 membered heteroaryl;

$R_4$ is selected from the group consisting of hydrogen, $C_{1-8}$ alkyl, $C_{1-8}$ deuterated alkyl, $C_{1-8}$ alkoxy, $C_{1-8}$ haloalkoxy, $C_{3-8}$ cycloalkyl and 3 to 10 membered heterocyclyl;

or, $R_3$ and $R_4$ are bonded to form a 3 to 10 membered heterocyclyl or 5 to 10 membered heteroaryl, wherein the 3 to 10 membered heterocyclyl or 5 to 10 membered heteroaryl is optionally further substituted by one or more substituents selected from the group consisting of deuterium, alkyl, deuterated alkyl, haloalkyl, halogen, amino, nitro, hydroxy, cyano, alkenyl, alkynyl, alkoxy, hydroxyalkyl, cycloalkyl, heterocyclyl, aryl, heteroaryl, —(CR$_9$R$_{10}$)$_n$—, —(CH$_2$)$_n$OR$_9$, —(CH$_2$)$_n$SR$_9$, —(CH$_2$)$_n$C(O)R$_9$, —(CH$_2$)$_n$C(O)OR$_9$, —(CH$_2$)$_n$S(O)$_m$R$_9$, —(CH$_2$)$_n$NR$_{10}$R$_{11}$, —(CH$_2$)$_n$C(O)NR$_{10}$R$_{11}$, —(CH$_2$)$_n$C(O)NHR$_{10}$, —(CH$_2$)$_n$NR$_{10}$C(O)R$_9$ and —(CH$_2$)$_n$NR$_{10}$S(O)$_m$R$_9$;

$R_b$ is selected from the group consisting of hydrogen, $C_{1-8}$ alkyl, $C_{1-8}$ deuterated alkyl and $C_{1-8}$ haloalkyl; wherein $R_b$ can be substituted on the oxo ring or on the $M_5$ ring;

p is an integer of 0, 1, 2, 3 or 4; and q is an integer of 0 or 1.

In a more preferred embodiment of the present invention, the compound of formula (I) is a compound of formula (VIII-A), a stereoisomer thereof, or a pharmaceutically acceptable salt thereof:

(VIII-A)

wherein:

$R_3$ and $R_4$ are bonded to form a 3 to 10 membered heterocyclyl or 5 to 10 membered heteroaryl, wherein the 3 to 10 membered heterocyclyl or 5 to 10 membered heteroaryl is optionally further substituted by one or more substituents selected from the group consisting of deuterium, alkyl, deuterated alkyl, haloalkyl, halogen, amino, nitro, hydroxy, cyano, alkenyl, alkynyl, alkoxy, hydroxyalkyl, cycloalkyl, heterocyclyl, aryl, heteroaryl, —(CR$_9$R$_{10}$)$_n$—, —(CH$_2$)$_n$OR$_9$, —(CH$_2$)$_n$SR$_9$, —(CH$_2$)$_n$C(O)R$_9$, —(CH$_2$)$_n$C(O)OR$_9$, —(CH$_2$)$_n$S(O)$_m$R$_9$, —(CH$_2$)$_n$NR$_{10}$R$_{11}$, —(CH$_2$)$_n$C(O)NR$_{10}$R$_{11}$, —(CH$_2$)$_n$C(O)NHR$_{10}$, —(CH$_2$)$_n$NR$_{10}$C(O)R$_9$ and —(CH$_2$)$_n$NR$_{10}$S(O)$_m$R$_9$;

$R_b$ is selected from the group consisting of hydrogen, $C_{1-8}$ alkyl, $C_{1-8}$ deuterated alkyl and $C_{1-8}$ haloalkyl;

$R_1$ is selected from the group consisting of hydrogen, $C_{1-8}$ alkyl, $C_{1-8}$ deuterated alkyl and $C_{1-8}$ haloalkyl;

x-1 is an integer of 0, 1, 2 or 3;

p is an integer of 0, 1, 2, 3 or 4; and q is an integer of 0 or 1.

In a more preferred embodiment of the present invention, the compound of formula (I) is a compound of formula (VIII-B), a stereoisomer thereof, or a pharmaceutically acceptable salt thereof:

(VIII-B)

wherein:

ring C is 4 to 7 membered heterocyclyl or heteroaryl, preferably 5 membered heterocyclyl;

each $R_a$ is identical or different and each is independently selected from the group consisting of hydrogen, cyano, $C_{1-6}$ alkyl, $C_{1-6}$ haloalkyl, $C_{1-6}$ alkoxy, $C_{3-6}$ cycloalkyl, —(CH$_2$)$_n$OR$_9$, —(CR$_9$R$_{10}$)$_n$— and —(CH$_2$)$_n$C(O)R$_9$, or, any two $R_a$ can form a 3 to 6 membered cycloalkyl;

$R_b$ is selected from the group consisting of hydrogen, $C_{1-8}$ alkyl, $C_{1-8}$ deuterated alkyl and $C_{1-8}$ haloalkyl;

$R_9$ and $R_{10}$ are independently selected from the group consisting of hydrogen and $C_{1-8}$ alkyl;

z is an integer of 0, 1, 2, 3 or 4; and p is 0, 1 or 2.

In a preferred embodiment of the present invention, the compound of each formula, the stereoisomer thereof, or the pharmaceutically acceptable salt thereof is characterized in that $R_1$ is selected from the group consisting of $C_{1-8}$ alkyl, $C_{3-8}$ cycloalkyl, 5 to 10 membered heteroaryl and halogen, preferably 5 to 6 membered heteroaryl, halogen and $C_{1-6}$ alky, and more preferably pyrazole, fluorine and methyl.

In a preferred embodiment of the present invention, the compound of each formula, the stereoisomer thereof, or the pharmaceutically acceptable salt thereof is characterized in that $R_a$ is selected from the group consisting of hydrogen, cyano, $C_{1-8}$ alkyl, $C_{2-8}$ alkenyl, $C_{2-8}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, —(CH$_2$)$_n$OR$_9$, —(CR$_9$R$_{10}$)$_n$— and —(CH$_2$)$_n$C(O)R$_9$, preferably hydrogen, cyano, hydroxy, $C_{1-6}$ alkyl, $C_{2-6}$ alkenyl, $C_{2-6}$ alkynyl, hydroxyC$_{1-6}$ alkyl, $C_{1-6}$ haloalkyl, 3 to 6 membered heterocyclyl and $C_{3-6}$ cycloalkyl; and most preferably methyl, ethyl, vinyl, ethynyl and trifluoromethyl.

In a preferred embodiment of the present invention, the compound of each formula, the stereoisomer thereof, or the pharmaceutically acceptable salt thereof is characterized in that $R_5$ is selected from the group consisting of hydrogen, $C_{1-8}$ alkyl, $C_{1-8}$ haloalkyl, $C_{1-8}$ hydroxyalkyl, $C_{1-8}$ alkoxy, $C_{1-8}$ haloalkoxy, halogen, $C_{3-8}$ cycloalkyl and 3 to 10 membered heterocyclyl, preferably hydrogen, $C_{1-6}$ alkyl, hydroxyC$_{1-6}$ alkyl, $C_{1-6}$ haloalkyl, $C_{3-6}$ cycloalkyl and 3 to 6 membered heterocyclyl; and most preferably cyclopropyl, isopropyl, hydroxyisopropyl, tert-butyl, trifluoromethyl and In another aspect, the present invention relates to a pharmaceutical composition comprising a therapeutically effective amount of the compound of each formula, the stereoisomer thereof, or the pharmaceutically acceptable salt thereof, and one or more pharmaceutically acceptable carriers, diluents or excipients.

In a preferred embodiment, the present invention also relates to an intermediate for preparing the compound of formula (I) according to claim 1 that is the compound of formula (III), the stereoisomer thereof, or the pharmaceutically acceptable salt thereof. The intermediate is a compound of formula (IX), a stereoisomer thereof, or a pharmaceutically acceptable salt thereof,

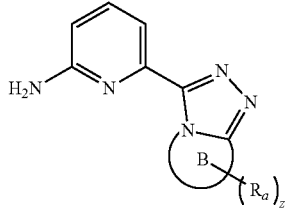

wherein:
ring B is heterocyclyl;
$R_a$ is selected from the group consisting of hydrogen, cyano, $C_{1-8}$ alkyl, $C_{2-8}$ alkenyl, $C_{2-8}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, $-(CH_2)_nOR_9$, $-(CR_9R_{10})_n-$ and $-(CH_2)_nC(O)R_9$, preferably hydrogen, cyano, hydroxy, $C_{1-6}$ alkyl, $C_{2-6}$ alkenyl, $C_{2-6}$ alkynyl, $C_{1-6}$ hydroxyalkyl, halo$C_{1-6}$ alkyl, 3 to 6 membered heterocyclyl and $C_{3-6}$ cycloalkyl; and most preferably methyl, ethyl, vinyl, ethynyl and $C_{1-3}$ haloalkyl;
z is 0, 1, 2, 3, 4 or 5.

In a preferred embodiment, the present invention also relates to a method for preparing the compound of formula (I) according to claim 1 that is the compound of formula (III), the stereoisomer thereof, or the pharmaceutically acceptable salt thereof, comprising the following step of:

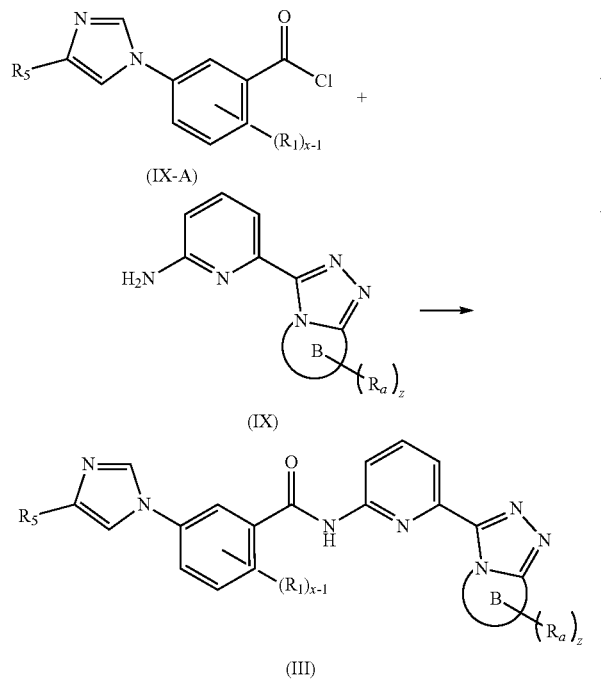

coupling a compound of formula (IX-A) with a compound of formula (IX) to obtain the compound of formula (III).

In a preferred embodiment, the present invention also relates to an intermediate for preparing the compound of formula (I) according to claim 1 that is the compound of formula (III), the stereoisomer thereof, or the pharmaceutically acceptable salt thereof. The intermediate is a compound of formula (X), a stereoisomer thereof, or a pharmaceutically acceptable salt thereof,

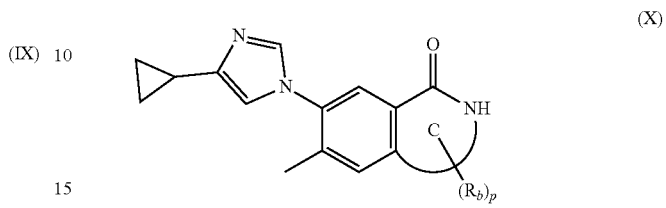

wherein:
ring C is heterocyclyl or heteroaryl;
$R_b$ is selected from the group consisting of hydrogen, $C_{1-8}$ alkyl, $C_{1-8}$ deuterated alkyl and $C_{1-8}$ haloalkyl; and
p is 0, 1 or 2.

In a preferred embodiment, the present invention also relates to a method for preparing the compound of formula (I) according to claim 1 that is the compound of formula (VIII-B), the stereoisomer thereof, or the pharmaceutically acceptable salt thereof, comprising the following step of:

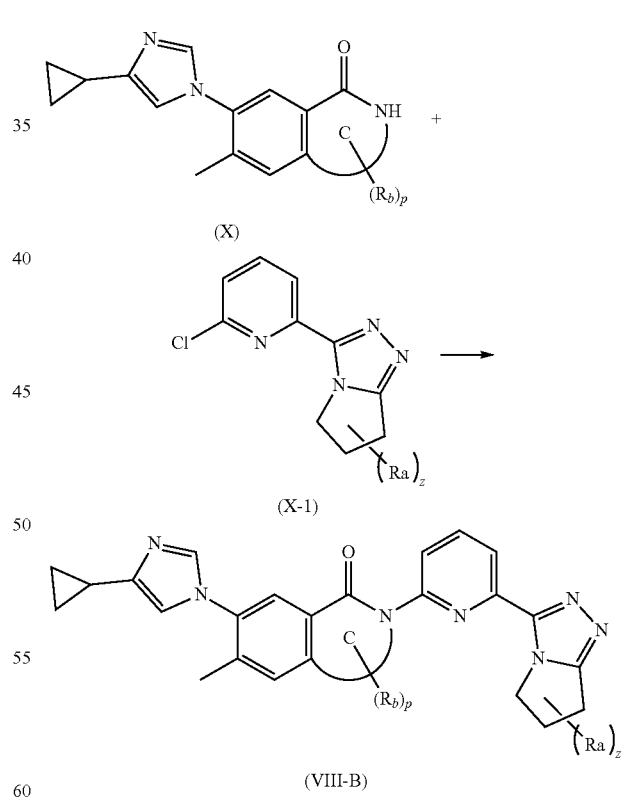

coupling a compound of formula (X-1) with a compound of formula (X) to obtain the compound of formula (VIII-B).

The present invention also relates to a synthetic scheme of the intermediate compound of formula (IX), the stereoisomer thereof, or the pharmaceutically acceptable salt thereof,

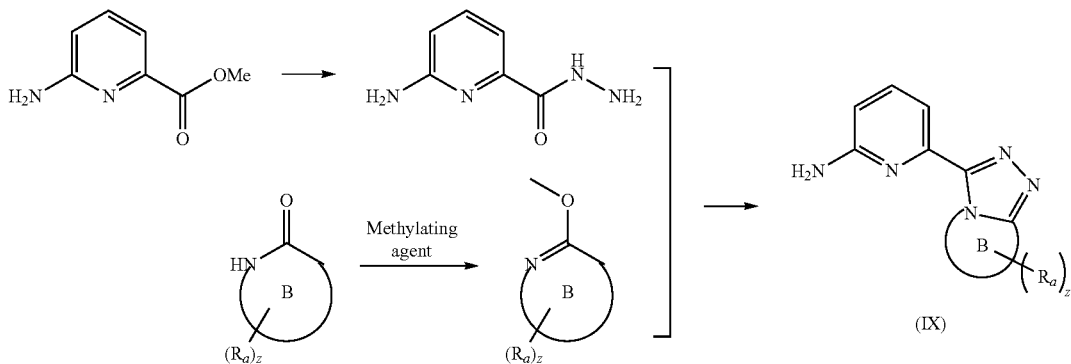

the compound of formula (IX) is synthesized by the above one-pot scheme, wherein each group is as defined in formula (IX).

The present invention also relates to a method for treating and/or preventing an ASK1-mediated disease with pathological features, comprising administering to a patient a therapeutically effective amount of the compound of formula (I), the stereoisomer thereof, or the pharmaceutically acceptable salt thereof, or the pharmaceutical composition thereof.

The present invention further relates to a use of the compound of formula (I), the stereoisomer thereof, or the pharmaceutically acceptable salt thereof, or the pharmaceutical composition thereof in the preparation of an ASK1 inhibitor medicament.

The present invention further relates to a use of the compound of formula (I), the stereoisomer thereof, or the pharmaceutically acceptable salt thereof, or the pharmaceutical composition thereof in the preparation of a medicament for treating neurodegenerative disorder, cardiovascular disorder, inflammatory disorder, metabolic disorder and ASK1, wherein the inflammatory disorder is preferably non-alcoholic steatohepatitis (NASH).

The present invention further relates to a use of the compound of formula (I), the stereoisomer thereof, or the pharmaceutically acceptable salt thereof, or the pharmaceutical composition thereof in the preparation of a medicament for treating non-alcoholic steatohepatitis (NASH).

The present invention also relates to a method for treating and/or preventing neurodegenerative disorder, cardiovascular disorder, inflammatory disorder, metabolic disorder, comprising administering to a patient a therapeutically effective amount of the compound of formula (I), the stereoisomer thereof, or the pharmaceutically acceptable salt thereof, or the pharmaceutical composition thereof.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, oxo, carboxy and carboxylate group, and preferably methyl, ethyl, isopropyl, tert-butyl, haloalkyl, deuterated alkyl, alkoxy-substituted alkyl and hydroxy-substituted alkyl.

The term "alkylene" refers to an alkyl of which a hydrogen atom is further substituted, for example, "methylene" refers to —$CH_2$—, "ethylene" refers to —$(CH_2)_2$—, "propylene" refers to —$(CH_2)_3$—, "butylene" refers to —$(CH_2)_4$— and the like. The above substituents can be bonded to different carbon atoms to form a carbon chain, or can be bonded to one carbon atom to form a cycloalkyl. The term "alkenyl" refers to an alkyl as defined above that consists of at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 8 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl and cycloheptyl.

The term "heterocyclyl" refers to a 3 to 20 membered saturated or partially unsaturated monocyclic or polycyclic hydrocarbon substituent group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, the heterocyclyl has 3 to 8 ring atoms; and most preferably 3 to 8 ring atoms. Non-limiting examples of monocyclic heterocyclyl include pyrrolidinyl, imidazolidinyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl, pyranyl and the like, and preferably tetrahydrofuranyl, pyrazolyl, morpholinyl, piperazinyl and pyranyl. Polycyclic heterocyclyl includes a heterocyclyl having a spiro ring, fused ring or bridged ring. The heterocyclyl having a spiro ring, fused ring or bridged ring is optionally bonded to another group via a single bond, or further bonded to other cycloalkyl, heterocyclyl, aryl and heteroaryl via any two or more atoms on the ring. The heterocyclyl group can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, oxo, carboxy and carboxylate group.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, for example, phenyl and naphthyl, and more preferably phenyl. The ring of aryl can be fused to the ring of heteroaryl, heterocyclyl or cycloalkyl, wherein the ring bonded to the parent structure is aryl ring. Non-limiting examples thereof include:

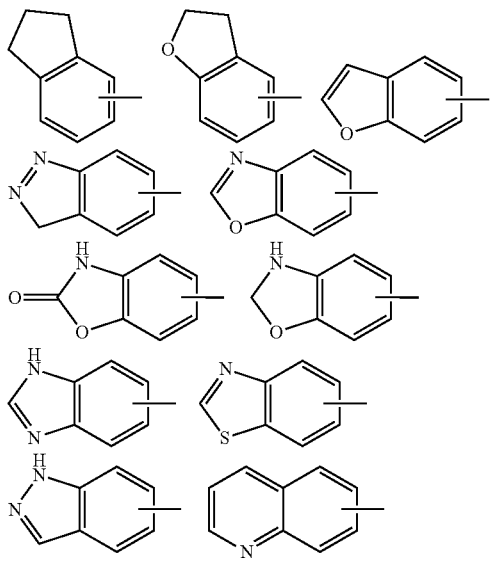

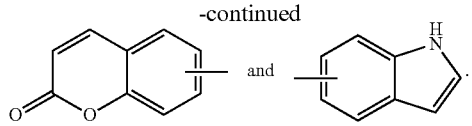

The aryl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy and carboxylate group.

The term "heteroaryl" refers to a 5 to 14 membered heteroaromatic system having 1 to 4 heteroatoms selected from the group consisting of O, S and N. The heteroaryl is preferably 5 to 10 membered heteroaryl, more preferably 5 or 6 membered heteroaryl, for example, imidazolyl, furyl, thienyl, thiazolyl, pyrazolyl, oxazolyl, pyrrolyl, triazolyl, tetrazolyl, pyridinyl, pyrimidinyl, thiadiazolyl, pyrazinyl and the like, preferably triazolyl, thienyl, imidazolyl, pyrazolyl or pyrimidinyl, thiazolyl; and more preferably triazolyl, pyrrolyl, thienyl, thiazolyl and pyrimidinyl. The ring of heteroaryl can be fused to the ring of aryl, heterocyclyl or cycloalkyl, wherein the ring bonded to the parent structure is heteroaryl ring. Non-limiting examples thereof include:

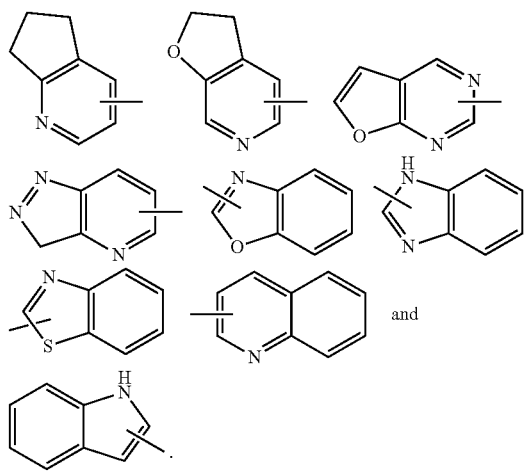

The heteroaryl group can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy and carboxylate group.

The term "alkoxy" refers to an —O-(alkyl) or an —O-(unsubstituted cycloalkyl) group, wherein the alkyl is as defined above. The alkoxy is preferably an alkoxy having 1 to 8 carbon atoms, more preferably an alkoxy having 1 to 6 carbon atoms, and most preferably an alkoxy having 1 to 3 carbon atoms. Non-limiting examples of alkoxy include methoxy, ethoxy, propoxy, butoxy, cyclopropyloxy, cyclobutyloxy, cyclopentyloxy, cyclohexyloxy. The alkoxy group can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy and carboxylate group.

"Haloalkyl" refers to an alkyl group substituted by one or more halogens, wherein the alkyl is as defined above.

"Haloalkoxy" refers to an alkoxy group substituted by one or more halogens, wherein the alkoxy is as defined above.

"Hydroxyalkyl" refers to an alkyl group substituted by hydroxy(s), wherein the alkyl is as defined above.

"Alkenyl" refers to chain alkenyl, also known as alkene group. The alkenyl is preferably an alkenyl having 2 to 8 carbon atoms, more preferably an alkenyl having 2 to 6 carbon atoms, and most preferably an alkenyl having 2 to 3 carbon atoms. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy or carboxylate group.

"Alkynyl" refers to (CH≡C—), preferably an alkynyl having 2 to 8 carbon atoms, more preferably an alkynyl having 2 to 6 carbon atoms, and most preferably an alkynyl having 2 to 3 carbon atoms. The alkynyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy or carboxylate group.

"Hydroxy" refers to an —OH group.
"Halogen" refers to fluorine, chlorine, bromine or iodine.
"Amino" refers to a —$NH_2$ group.
"Cyano" refers to a —CN group.
"Nitro" refers to a —$NO_2$ group.
"Carboxy" refers to a —C(O)OH group.
"THF" refers to tetrahydrofuran.
"EtOAc" refers to ethyl acetate.
"MeOH" refers to methanol.
"DMF" refers to N,N-dimethylformamide.
"DIPEA" refers to diisopropylethylamine.
"TFA" refers to trifluoroacetic acid.
"MeCN" refers to acetonitrile.
"DMA" refers to N,N-dimethylacetamide.
"$Et_2O$" refers to diethyl ether.
"DCE" refers to 1,2-dichloroethane.
"DIPEA" refers to N,N-diisopropylethylamine.
"NBS" refers to N-bromosuccinimide.
"NIS" refers to N-iodosuccinimide.
"Cbz-Cl" refers to benzyl chloroformate.
"$Pd_2(dba)_3$" refers to tris(dibenzylideneacetone)dipalladium.
"Dppf" refers to 1,1'-bisdiphenylphosphinoferrocene.
"HATU" refers to 2-(7-azabenzotriazol-1-yl)-N,N,N',N'-tetramethyluronium hexafluorophosphate.
"KHMDS" refers to potassium hexamethyldisilazide.
"LiHMDS" refers to lithium bis(trimethylsilyl)amide.
"MeLi" refers to methyl lithium.
"n-BuLi" refers to n-butyl lithium.
"$NaBH(OAc)_3$" refers to sodium triacetoxyborohydride.

Different expressions such as "X is selected from the group consisting of A, B or C", "X is selected from the group consisting of A, B and C", "X is A, B or C", "X is A, B and C" and the like, express the same meaning, that is, X can be any one or more of A, B and C.

The hydrogen atom of the present invention can be substituted by its isotope deuterium. Any of the hydrogen atoms in the compound of the examples of the present invention can also be substituted by deuterium.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical positions. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

PREFERRED EMBODIMENTS

The present invention is further described in combination with the following examples, which are not intended to limit the scope of the present invention.

EXAMPLES

The structures of the compounds of the present invention were identified by nuclear magnetic resonance (NMR) and/or liquid chromatography-mass spectrometry (LC-MS). NMR chemical shifts (δ) are given in parts per million (ppm). NMR was determined by a Bruker AVANCE-400 machine. The solvents for determination were deuterated-dimethyl sulfoxide (DMSO-$d_6$), deuterated-methanol ($CD_3OD$) and deuterated-chloroform ($CDCl_3$), and the internal standard was tetramethylsilane (TMS).

Liquid chromatography-mass spectrometry (LC-MS) was determined on an Agilent 1200 Infinity Series mass spectrometer. High performance liquid chromatography (HPLC) was determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for column chromatography.

The starting materials used in the examples of the present invention are known and commercially available, or can be synthesized by adopting or according to known methods in the art.

Unless otherwise stated, all reactions of the present invention were carried out under continuous magnetic stirring in a dry nitrogen or argon atmosphere, the solvent was dry, and the reaction temperature was in degrees Celsius.

Example 1

Preparation of 5-(4-cyclopropyl-1H-imidazol-1-yl)-N-(6-(6,7-dihydro-5H-pyrrolo[2,1-c][1,2,4]triazol-3-yl)pyridin-2-yl)-2-fluoro-4-methylbenzamide

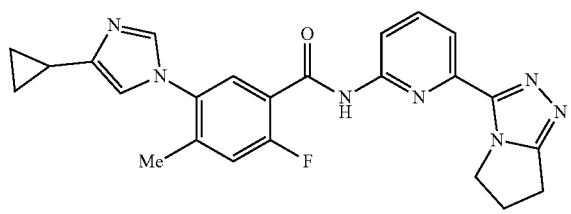 [SMILES: Cc1cc(F)c(C(=O)Nc2cccc(-c3nnc4n3CCC4)n2)cc1-n1cnc(C2CC2)c1]

Step 1: Preparation of 5-amino-2-fluoro-4-methylbenzonitrile

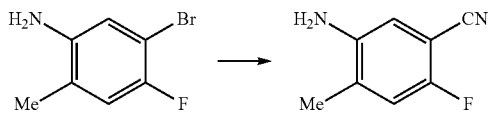 [SMILES: Cc1cc(F)c(Br)cc1N ; Cc1cc(F)c(C#N)cc1N]

5-Bromo-4-fluoro-2-methylaniline (10.0 g, 49.0 mmol) and cuprous cyanide (8.78 g, 98.0 mmol) were mixed in NMP (50 mL). The reaction solution was stirred under a nitrogen atmosphere at 180° C. for 1 hour, and then at 100° C. overnight. After cooling, the reaction solution was added with ammonia solution (28 wt %), stirred for 15 minutes, and extracted with EtOAc three times. The organic phases were combined, and washed with saturated brine three times. The organic phase was then dried over anhydrous sodium sulfate, and concentrated under reduced pressure. The residue was subjected to column chromatography to obtain the title compound 5-amino-2-fluoro-4-methylbenzonitrile (5.70 g, 78%).

MS m/z (ESI): 151.1 [M+H]⁺.

Step 2: Preparation of 5-((2-cyclopropyl-2-oxoethyl)amino)-2-fluoro-4-methylbenzonitrile

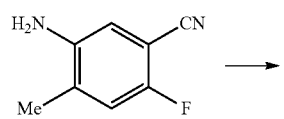

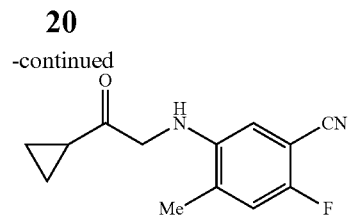

5-Amino-2-fluoro-4-methylbenzonitrile (5.70 g, 38.0 mmol), K₂CO₃ (6.30 g, 45.6 mmol), KI (0.630 g, 3.80 mmol) and 2-bromo-1-cyclopropylethan-1-one (7.43 g, 45.6 mmol) were mixed in DMF (50 mL). The reaction solution was stirred under a nitrogen atmosphere at 80° C. for 90 minutes. After cooling, the reaction solution was added with another 2-bromo-1-cyclopropylethan-1-one (3.00 g, 18.4 mmol) and K₂CO₃ (2.54 g, 18.4 mmol), and stirred at 75° C. for 1 hour. The reaction solution was cooled to room temperature, added with water, and filtrated after standing for 15 minutes. The filter cake was washed with water, and dried to obtain the crude title compound 5-((2-cyclopropyl-2-oxoethyl)amino)-2-fluoro-4-methylbenzonitrile (6.80 g, 77%).

MS m/z (ESI): 233.1 [M+H]⁺.

Step 3: Preparation of 5-(4-cyclopropyl-2-thiol-1H-imidazol-1-yl)-2-fluoro-4-methylbenzonitrile

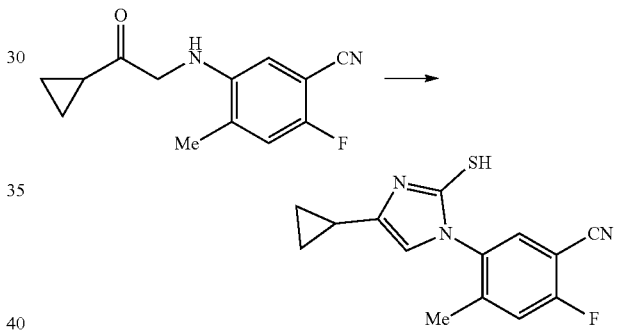

A solution of 5-((2-cyclopropyl-2-oxoethyl)amino)-2-fluoro-4-methylbenzonitrile (6.80 g, 29.3 mmol) and KSCN (5.69 g, 58.6 mmol) in acetic acid (100 mL) was stirred at 110° C. for 4 hours. After cooling, the reaction solution was concentrated, added with CH₂Cl₂ and water. The organic phase was separated, and the aqueous phase was extracted with CH₂Cl₂ once again. The organic phases were combined, dried over anhydrous sodium sulfate, and concentrated under reduced pressure to obtain the crude product 5-(4-cyclopropyl-2-thiol-1H-imidazol-1-yl)-2-fluoro-4-methylbenzonitrile (8.00 g), which was used directly in the next step.

MS m/z (ESI): 274.1 [M+H]⁺.

Step 4: Preparation of 5-(4-cyclopropyl-1H-imidazol-1-yl)-2-fluoro-4-methylbenzonitrile

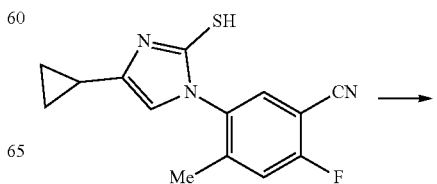

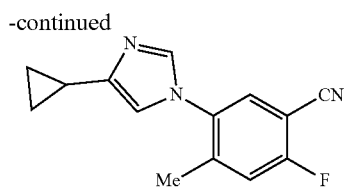

Hydrogen peroxide (30 wt %, 10.0 mL) was slowly added dropwise to a solution of the above crude product in acetic acid (160 mL) and water (32 mL) at 50° C. After completion of the addition, the reaction solution was stirred at this temperature for 1 hour. The reaction solution was cooled to room temperature, added slowly with aqueous $Na_2SO_3$ solution (20 wt %, 100 mL), and then stirred for 30 minutes. The reaction solution was concentrated to remove the organic solvent, and the aqueous phase was extracted with $CH_2Cl_2$ twice. The organic phases were combined, washed with saturated aqueous sodium bicarbonate solution and saturated brine successively, dried over anhydrous sodium sulfate, and concentrated under reduced pressure. The residue was subjected to column chromatography to obtain the title compound 5-(4-cyclopropyl-1H-imidazol-1-yl)-2-fluoro-4-methylbenzonitrile (3.3 g, yield of two steps: 47%).
MS m/z (ESI): 242.1 [M+H]$^+$.

Step 5: Preparation of 6-aminopicolinohydrazide

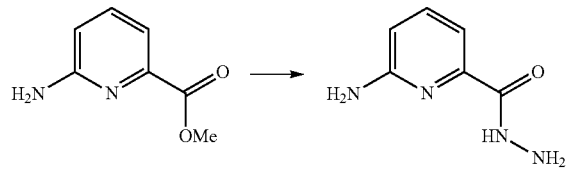 [SMILES: COC(=O)c1cccc(N)n1 ; NNC(=O)c1cccc(N)n1]

Methyl 6-aminopicolinate (2.0 g, 13 mmol) was dissolved in ethanol (60 mL) at room temperature, and then hydrazine hydrate (4.1 g, 66 mmol) was added. The reaction solution was heated to 80° C., and stirred at this temperature for 5 hours. After the reaction solution was cooled slowly to room temperature, the precipitated solid was filtrated. The filter cake was collected to obtain the title compound 6-aminopicolinohydrazide (1.6 g, 80%).
MS m/z (ESI): 153.2 [M+H]$^+$.

Step 6: Preparation of 6-(6,7-dihydro-5H-pyrrolo[2,1-c][1,2,4]triazol-3-yl)pyridin-2-amine

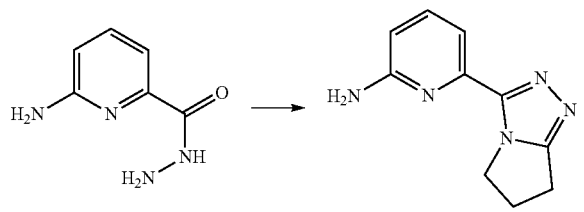 [SMILES: NNC(=O)c1cccc(N)n1 ; Nc1cccc(-c2nnc3n2CCC3)n1]

6-Aminopicolinohydrazide (300 mg, 1.97 mmol) was dissolved in 2-pentanol (5 mL) and acetic acid (1 mL) at room temperature, and then 5-methoxy-3,4-dihydro-2H-pyrrole (195 mg, 1.97 mmol) was added. The reaction solution was heated to 125° C., and stirred at this temperature for 12 hours. After cooling to room temperature, the reaction solution was concentrated under reduced pressure. The residue was added with saturated aqueous $NaHCO_3$ solution (5 mL), and extracted with dichloromethane (50 mL×2). The organic phase was washed with saturated brine, dried over anhydrous sodium sulfate, and concentrated. The residue was subjected to column chromatography to obtain the title compound 6-(6,7-dihydro-5H-pyrrolo[2,1-c][1,2,4]triazol-3-yl)pyridin-2-amine (360 mg, 91%).
MS m/z (ESI): 202.1 [M+H]$^+$.

Step 7: Preparation of 5-(4-cyclopropyl-1H-imidazol-1-yl)-2-fluoro-4-methylbenzoyl Chloride

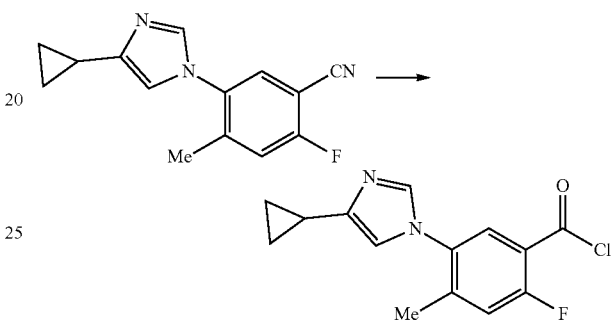

5-(4-Cyclopropyl-1H-imidazol-1-yl)-2-fluoro-4-methylbenzonitrile (1.8 g, 7.47 mmol) was dissolved in 30 mL of concentrated hydrochloric acid, and the reaction solution was stirred overnight under heating reflux. After cooling, the reaction solution was concentrated and dried to obtain 5-(4-cyclopropyl-1H-imidazol-1-yl)-2-fluoro-4-methylbenzoic acid hydrochloride (2 g, a crude product), which was used directly in the next step.

The above 5-(4-cyclopropyl-1H-imidazol-1-yl)-2-fluoro-4-methylbenzoic acid hydrochloride (100 mg, the above crude product) was dissolved in thionyl chloride (5 mL) at room temperature, and stirred for 2 hours under heating reflux. After cooling, the reaction solution was concentrated under reduced pressure to obtain a pale yellow solid product, which was used directly in the next step.

Step 8: Preparation of 5-(4-cyclopropyl-1H-imidazol-1-yl)-N-(6-(6,7-dihydro-5H-pyrrolo[2,1-c][1,2,4]triazol-3-yl)pyridin-2-yl)-2-fluoro-4-methylbenzamide

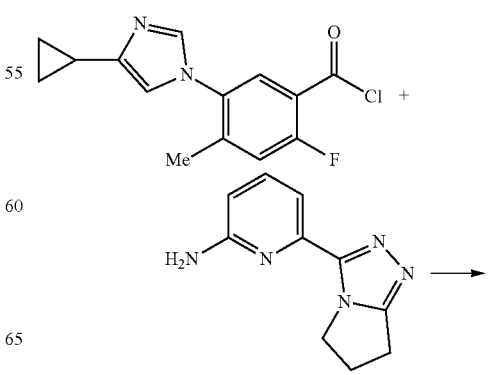

-continued

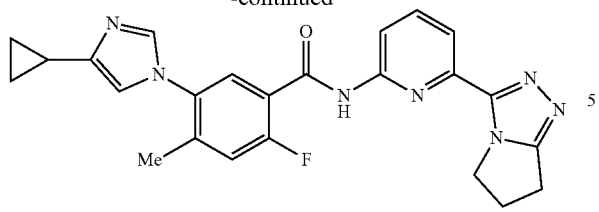

6-(6,7-Dihydro-5H-pyrrolo[2,1-c][1,2,4]triazol-3-yl)pyridin-2-amine (43 mg, 0.22 mmol) was added to a solution of 5-(4-cyclopropyl-1H-imidazol-1-yl)-2-fluoro-4-methylbenzoyl chloride (100 mg, the crude product of the above step) in THF (5 mL) and pyridine (5 mL) at room temperature, and then 4-dimethylaminopyridine (11 mg, 0.09 mmol) was added. The reaction solution was heated to 45° C., and stirred at this temperature for 2 hours. The reaction solution was added dropwise with water (5 mL), and extracted with dichloromethane (50 mL×2). The organic phase was washed with saturated brine, dried over anhydrous sodium sulfate, and concentrated. The residue was subjected to column chromatography to obtain the title compound 5-(4-cyclopropyl-1H-imidazol-1-yl)-N-(6-(6,7-dihydro-5H-pyrrolo[2,1-c][1,2,4]triazol-3-yl)pyridin-2-yl)-2-fluoro-4-methylbenzamide (60 mg, 63%).

$^1$H NMR (400 MHz, CDCl$_3$) δ 9.05 (d, J=15.1 Hz, 1H), 8.34 (d, J=8.2 Hz, 1H), 8.13-8.02 (m, 2H), 7.88 (t, J=8.0 Hz, 1H), 7.48 (m, 1H), 7.20 (d, J=12.4 Hz, 1H), 6.80 (m, 1H), 4.53-4.34 (m, 2H), 3.04 (t, J=7.7 Hz, 2H), 2.96-2.74 (m, 2H), 2.30 (s, 3H), 1.98-1.82 (m, 1H), 0.90 (m, 2H), 0.88-0.76 (m, 2H);

MS m/z (ESI): 444.1 [M+H]$^+$.

Example 2

5-(4-Cyclopropyl-1H-imidazol-1-yl)-2-fluoro-4-methy 1-N-(6-(6,7,8,9-tetrahydro-5H-[1,2,4]triazolo[4,3-a]azepin-3-yl)pyridin-2-yl)benzamide

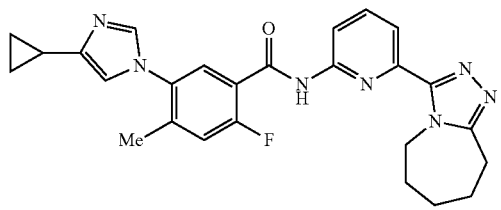 [SMILES: Cc1cc(F)c(C(=O)Nc2cccc(-c3nnc4n3CCCCC4)n2)cc1-n1cnc(C2CC2)c1]

5-(4-Cyclopropyl-1H-imidazol-1-yl)-2-fluoro-4-methy 1-N-(6-(6,7,8,9-tetrahydro-5H-[1,2,4]triazolo[4,3-a]azepin-3-yl)pyridin-2-yl)benzamide was prepared in accordance with the method of Example 1.

$^1$H NMR (400 MHz, CDCl$_3$) δ 9.00 (d, J=14.9 Hz, 1H), 8.29 (d, J=0.8 Hz, 1H), 7.99 (d, J=7.3 Hz, 1H), 7.92-7.90 (m, 1H), 7.83 (t, J=7.9 Hz, 1H), 7.43 (d, J=1.0 Hz, 1H), 7.12 (d, J=12.3 Hz, 1H), 6.73 (m, 1H), 4.57 (m, 2H), 3.03-3.01 (m, 2H), 2.22 (s, 3H), 1.85 (m, 3H), 1.81 (m, 2H), 1.74 (m, 2H), 0.85-0.82 (m, 2H), 0.79-0.76 (m, 2H);

MS m/z (ESI):472.2 [M+H]$^+$.

Example 3

5-(4-Cyclopropyl-1H-imidazol-1-yl)-2-fluoro-4-methyl-N-(6-(5,6,7,8-tetrahydro-[1,2,4]triazolo[4,3-a]pyridin-3-yl)pyridin-2-yl)benzamide

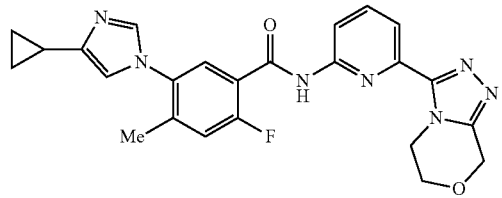 [SMILES: Cc1cc(F)c(C(=O)Nc2cccc(-c3nnc4n3CCOC4)n2)cc1-n1cnc(C2CC2)c1]

5-(4-Cyclopropyl-1H-imidazol-1-yl)-2-fluoro-4-methy 1-N-(6-(5,6,7,8-tetrahydro-[1,2,4]triazolo[4,3-a]pyridin-3-yl)pyridin-2-yl)benzamide was prepared in accordance with the method of Example 1.

$^1$H NMR (400 MHz, CDCl$_3$) δ 8.98 (d, J=14.6 Hz, 1H), 8.27 (d, J=8.2 Hz, 1H), 7.99 (t, J=7.5 Hz, 2H), 7.81 (t, J=8.0 Hz, 1H), 7.39 (s, 1H), 7.12 (d, J=12.3 Hz, 1H), 6.72 (s, 1H), 4.41 (t, J=6.0 Hz, 2H), 3.00 (t, J=6.4 Hz, 2H), 2.22 (s, 3H), 2.03-1.95 (m, 2H), 1.93-1.87 (m, 2H), 1.85-1.79 (m, 1H), 0.88-0.79 (m, 2H), 0.78-0.70 (m, 2H);

MS m/z (ESI):458.2 [M+H]$^+$.

Example 4

5-(4-Cyclopropyl-1H-imidazol-1-yl)-N-(6-(5,6-dihydro-8H-[1,2,4]triazolo[3,4-c][1,4]oxazin-3-yl)pyridin-2-yl)-2-fluoro-4-methylbenzamide 5-(4-Cyclopropyl-1H-imidazol-1-yl)-N-(6-(5,6-dihydro-8H-[1,2,4]triazolo[3,4-c][1,4]oxazin-3-yl)pyridin-2-yl)-2-fluoro-4-methylbenzamide was prepared in accordance with the method of Example 1.

$^1$H NMR (400 MHz, CDCl$_3$) δ 9.08 (d, J=14.7 Hz, 1H), 8.41-8.35 (m, 1H), 8.13-8.07 (m, 1H), 8.05 (d, J=7.3 Hz, 1H), 7.91 (t, J=8.0 Hz, 1H), 7.48 (d, J=1.2 Hz, 1H), 7.20 (d, J=12.3 Hz, 1H), 6.80 (d, J=1.2 Hz, 1H), 5.06 (s, 2H), 4.59 (t, J=5.2 Hz, 2H), 4.09 (t, J=5.3 Hz, 2H), 2.30 (s, 3H), 1.95-1.86 (m, 1H), 0.95-0.87 (m, 2H), 0.87-0.78 (m, 2H);

MS m/z (ESI):460.2 [M+H]$^+$.

Example 5

5-(4-Cyclopropyl-1H-imidazol-1-yl)-2-fluoro-4-methyl-N-(6-(5,6,7,8-tetrahydro-[1,2,4]triazolo[4,3-a]pyrazin-3-yl)pyridin-2-yl)benzamide

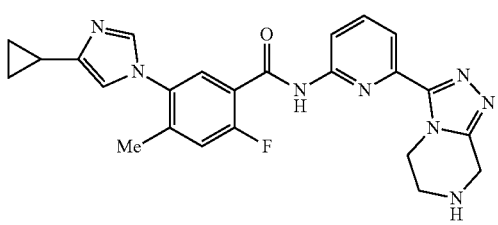 [SMILES: Cc1cc(F)c(C(=O)Nc2cccc(-c3nnc4n3CCNC4)n2)cc1-n1cnc(C2CC2)c1]

5-(4-Cyclopropyl-1H-imidazol-1-yl)-2-fluoro-4-methyl-N-(6-(5,6,7,8-tetrahydro-[1,2,4]triazolo[4,3-a]pyrazin-3-yl)pyridin-2-yl)benzamide was prepared in accordance with the method of Example 1.

$^1$H NMR (400 MHz, CDCl$_3$) δ 9.01 (d, J=14.5 Hz, 1H), 8.29 (d, J=8.3 Hz, 1H), 7.99 (t, J=8.3 Hz, 2H), 7.83 (d, J=8.0 Hz, 1H), 7.42 (s, 1H), 7.12 (d, J=12.3 Hz, 1H), 6.73 (s, 1H), 4.45 (t, J=5.5 Hz, 2H), 4.27 (s, 2H), 3.24 (t, J=5.5 Hz, 2H), 2.33 (s, 1H), 2.22 (s, 3H), 1.84-1.82 (m, 1H), 0.87-0.80 (m, 2H), 0.78-0.75 (m, 2H);

MS m/z (ESI): 459.2 [M+H]$^+$.

Example 6

5-(4-Cyclopropyl-1H-imidazol-1-yl)-2-fluoro-4-methyl-N-(6-(7-methyl-5,6,7,8-tetrahydro-[1,2,4]triazolo[4,3-a]pyrazin-3-yl)-pyridin-2-yl)benzamide

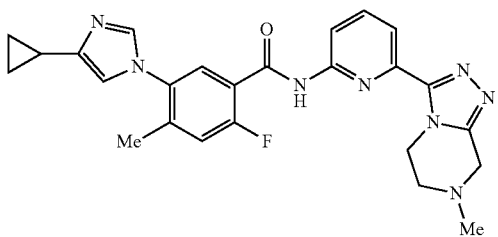 [SMILES: Cc1cc(F)c(C(=O)Nc2cccc(-c3nnc4n3CCN(C)C4)n2)cc1-n1cnc(C2CC2)c1]

5-(4-Cyclopropyl-1H-imidazol-1-yl)-2-fluoro-4-methyl-N-(6-(7-methyl-5,6,7,8-tetrahydro-[1,2,4]triazolo[4,3-a]pyrazin-3-yl)pyridin-2-yl)benzamide was prepared in accordance with the method of Example 1.

$^1$H NMR (400 MHz, CDCl$_3$) δ 8.98 (d, J=14.8 Hz, 1H), 8.29 (d, J=8.2 Hz, 1H), 8.01 (m, 2H), 7.82 (t, J=8.0 Hz, 1H), 7.44 (s, 1H), 7.12 (d, J=12.3 Hz, 1H), 6.73 (s, 1H), 4.49 (t, J=5.5 Hz, 2H), 3.80 (s, 2H), 2.83 (t, J=5.5 Hz, 2H), 2.48 (s, 3H), 2.22 (s, 3H), 1.85 (m, 1H), 0.85-0.82 (m, 2H), 0.79-077 (m, 2H);

MS (ESI):473.2 [M+H]$^+$.

Example 7

4-(4-Cyclopropyl-1H-imidazol-1-yl)-N-(3-(6,7-dihydro-5H-pyrrolo[2,1-c][1,2,4]triazol-3-yl)phenyl)picolinamide

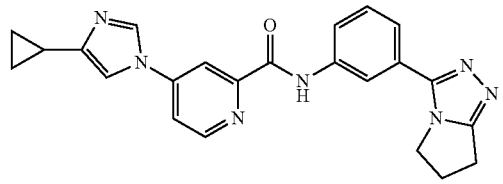 [SMILES: O=C(Nc1cccc(-c2nnc3n2CCC3)c1)c1cc(-n2cnc(C3CC3)c2)ccn1]

4-(4-Cyclopropyl-1H-imidazol-1-yl)-N-(3-(6,7-dihydro-5H-pyrrolo[2,1-c][1,2,4]triazol-3-yl)phenyl)picolinamide was prepared in accordance with the method of Example 1.

$^1$H NMR (400 MHz, CDCl$_3$) δ 10.16 (s, 1H), 8.68 (d, J=5.4 Hz, 1H), 8.49 (s, 1H), 8.27 (d, J=2.1 Hz, 1H), 8.01 (d, J=1.0 Hz, 1H), 7.92-7.64 (m, 2H), 7.63-7.41 (m, 2H), 7.22 (d, J=1.0 Hz, 1H), 4.35 (t, J=7.1 Hz, 2H), 3.08-3.04 (m, 2H), 2.89-2.84 (m, 2H), 1.94-1.90 (m, 1H), 0.95-0.91 (m, 2H), 0.87-0.84 (m, 2H);

MS m/z (ESI): 412.2 [M+H]$^+$.

Example 8

(R)-5-(4-Cyclopropyl-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide

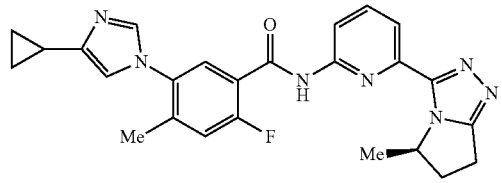 [SMILES: Cc1cc(F)c(C(=O)Nc2cccc(-c3nnc4n3[C@H](C)CC4)n2)cc1-n1cnc(C2CC2)c1]

Step 1: Preparation of (R)-5-methoxy-2-methyl-3,4-dihydro-2H-pyrrole

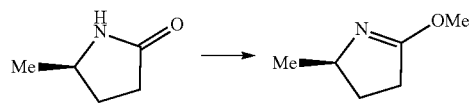 [SMILES: C[C@@H]1CCC(=O)N1 ; COC1=N[C@H](C)CC1]

Trimethyloxonium tetrafluoroborate (3.55 g, 24.0 mmol) was added to a solution of (R)-5-methylpyrrolidin-2-one (1.7 g, 17.2 mmol) in dichloromethane (40 mL) in batches in an ice bath. The reaction solution was warmed up to room temperature slowly, and stirred at this temperature for 5 hours. The reaction solution was added with saturated aqueous NaHCO$_3$ solution (5 mL), and extracted with dichloromethane (50 mL×2). The organic phase was washed with saturated brine, dried over anhydrous sodium sulfate, added with glacial acetic acid (5 mL), and concentrated under reduced pressure to obtain the crude product, which was used directly in the next step.

MS m/z (ESI): 114.1 [M+H]$^+$.

Step 2: Preparation of (R)-6-(5-methyl-6,7-dihydro-5H-pyrrolo[2,1-c][1,2,4]triazol-3-yl)pyridin-2-amine

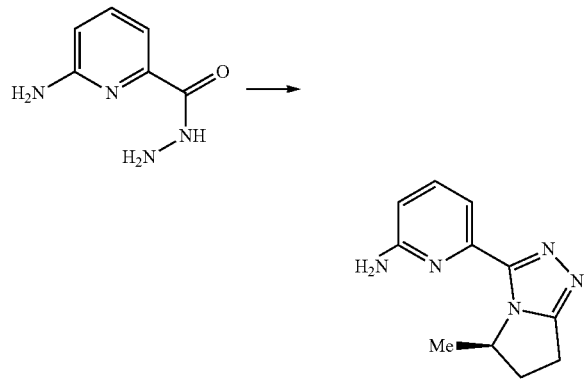

6-Aminopicolinohydrazide (2.35 g, 15.4 mmol) was dissolved in 2-pentanol (15 mL) and acetic acid (2 mL) at room temperature, and then (R)-5-methoxy-2-methyl-3,4-dihydro-2H-pyrrole (1.93 g, 17.1 mmol) was added. The reaction solution was heated to 125° C., and stirred at this temperature for 12 hours. After cooling to room temperature, the reaction solution was concentrated under reduced pressure. The residue was added with saturated aqueous NaHCO₃ solution (5 mL), and extracted with dichloromethane (50 mL×2). The organic phase was washed with saturated brine, dried over anhydrous sodium sulfate, and concentrated. The residue was subjected to column chromatography to obtain the title compound (R)-6-(5-methyl-6,7-dihydro-5H-pyrrolo[2,1-c][1,2,4]triazol-3-yl)pyridin-2-amine (1.62 g, yield of two steps: 49%).

$^1$H NMR (400 MHz, CDCl$_3$) δ 7.65 (m, 1H), 7.61-7.42 (m, 1H), 6.54 (m, 1H), 5.17-4.88 (m, 1H), 3.18-2.77 (m, 3H), 2.43-2.31 (m, 1H), 1.53-1.37 (m, 3H);

MS m/z (ESI): 216.1 [M+H]⁺.

Step 3: Preparation of (R)-5-(4-cyclopropyl-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide

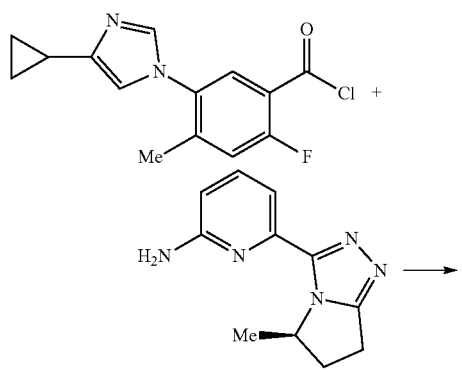

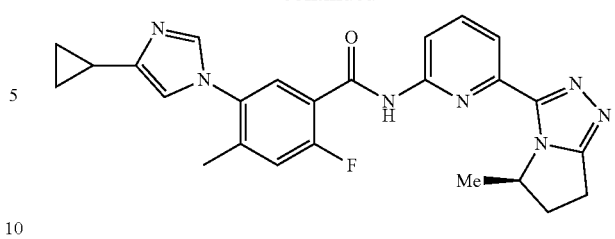

(R)-6-(5-Methyl-6,7-dihydro-5H-pyrrolo[2,1-c][1,2,4]triazol-3-yl)pyridin-2-amine (139 mg, 0.65 mmol) was added to a solution of 5-(4-cyclopropyl-1H-imidazol-1-yl)-2-fluoro-4-methylbenzoyl chloride (298 mg, 1.07 mmol) in THF (10 mL) and pyridine (10 mL) at room temperature, and then 4-dimethylaminopyridine (12 mg, 0.097 mmol) was added. The reaction solution was heated to 45° C., and stirred at this temperature for 2 hours. The reaction solution was added with water (5 mL), and extracted with dichloromethane (50 mL×2). The organic phase was washed with saturated brine, dried over anhydrous sodium sulfate, and concentrated. The residue was subjected to column chromatography to obtain the title compound (R)-5-(4-cyclopropyl-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide (151 mg, yield 51%).

$^1$H NMR (400 MHz, CDCl$_3$) δ 9.06 (d, J=15.6 Hz, 1H), 8.36-8.34 (m, 1H), 8.10 (t, J=7.2 Hz, 2H), 7.89 (t, J=8.0 Hz, 1H), 7.48 (s, 1H), 7.20 (d, J=12.6 Hz, 1H), 6.80 (s, 1H), 5.03 (s, 1H), 3.16-2.94 (m, 3H), 2.48-2.41 (m, 1H), 2.30 (s, 3H), 1.94-1.90 (m, 1H), 1.56 (d, J=6.4 Hz, 3H), 0.92-0.90 (m, 2H), 0.86-0.73 (m, 2H);

MS m/z (ESI): 458.1 [M+H]⁺.

Example 9

(S)-5-(4-Cyclopropyl-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide

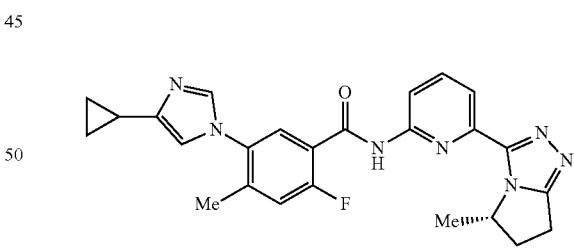

(S)-5-(4-Cyclopropyl-1H-imidazol-1-yl)-2-fluoro-4-methyl-N-(6-(5-methyl-6,7-di hydro-5H-pyrrolo[2,1-c][1,2,4]triazol-3-yl)pyridin-2-yl)benzamide was prepared in accordance with the method of Example 8.

$^1$H NMR (400 MHz, CDCl$_3$) δ 9.06 (d, J=15.6 Hz, 1H), 8.36-8.34 (m, 1H), 8.10 (t, J=7.2 Hz, 2H), 7.89 (t, J=8.0 Hz, 1H), 7.48 (s, 1H), 7.20 (d, J=12.6 Hz, 1H), 6.80 (s, 1H), 5.03 (s, 1H), 3.16-2.94 (m, 3H), 2.48-2.41 (m, 1H), 2.30 (s, 3H), 1.94-1.90 (m, 1H), 1.56 (d, J=6.4 Hz, 3H), 0.92-0.90 (m, 2H), 0.86-0.73 (m, 2H);

MS m/z (ESI): 458.1 [M+H]⁺.

Example 10

5-(4-Cyclopropyl-1H-imidazol-1-yl)-N-(6-(5,5-dimethyl-6,7-dihydro-5H-pyrrolo[2,1-c][1,2,4]triazol-3-yl)pyridin-2-yl)-2-fluoro-4-methylbenzamide

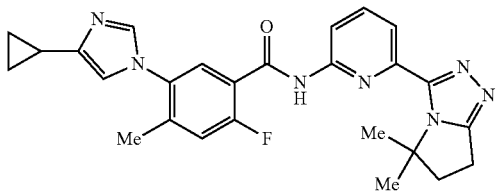 [SMILES: Cc1cc(F)c(C(=O)Nc2cccc(-c3nnc4n3C(C)(C)CC4)n2)cc1-n1cnc(C2CC2)c1]

Step 1: Preparation of 5-methoxy-2,2-dimethyl-3,4-dihydro-2H-pyrrole

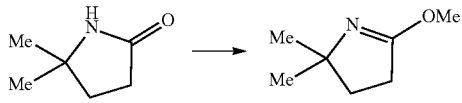 [SMILES: CC1(C)CCC(=O)N1 ; COC1=NC(C)(C)CC1]

Trimethyloxonium tetrafluoroborate (0.66 g, 4.45 mmol) was added to a solution of 5,5-dimethylpyrrolidin-2-one (0.36 g, 3.2 mmol) in dichloromethane (30 mL) in batches in an ice bath. The reaction solution was warmed up to room temperature slowly, and stirred at this temperature for 5 hours. The reaction solution was added with saturated aqueous NaHCO$_3$ solution (5 mL), and extracted with dichloromethane (50 mL×2). The organic phase was washed with saturated brine, dried over anhydrous sodium sulfate, added with glacial acetic acid (5 mL), and concentrated under reduced pressure to obtain the crude product, which was used directly in the next step.

MS m/z (ESI): 128.2 [M+H]$^+$.

Step 2: Preparation of 6-(5,5-dimethyl-6,7-dihydro-5H-pyrrolo[2,1-c][1,2,4]triazol-3-yl)pyridin-2-amine

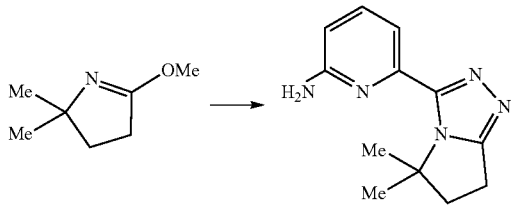 [SMILES: COC1=NC(C)(C)CC1 ; CC1(C)CCc2nnc(-c3cccc(N)n3)n21]

6-Aminopicolinohydrazide (435 mg, 2.86 mmol) was dissolved in 2-pentanol (15 mL) and acetic acid (2 mL) at room temperature, and then 5-methoxy-2,2-dimethyl-3,4-dihydro-2H-pyrrole (404 mg, 3.2 mmol) was added. The reaction solution was heated to 125° C., and stirred at this temperature for 12 hours. After cooling to room temperature, the reaction solution was concentrated under reduced pressure. The residue was added with saturated aqueous NaHCO$_3$ solution (5 mL), and extracted with dichloromethane (50 mL×2). The organic phase was washed with saturated brine, dried over anhydrous sodium sulfate, and concentrated. The residue was subjected to column chromatography to obtain the title compound 6-(5,5-dimethyl-6,7-dihydro-5H-pyrrolo[2,1-c][1,2,4]triazol-3-yl)pyridin-2-amine (380 mg, yield of two steps: 52%).

MS m/z (ESI): 230.1 [M+H]$^+$.

Step 3: Preparation of 5-(4-cyclopropyl-1H-imidazol-1-yl)-N-(6-(5,5-dimethyl-6,7-dihydro-5H-pyrrolo[2,1-c][1,2,4]triazol-3-yl)pyridin-2-yl)-2-fluoro-4-methylbenzamide

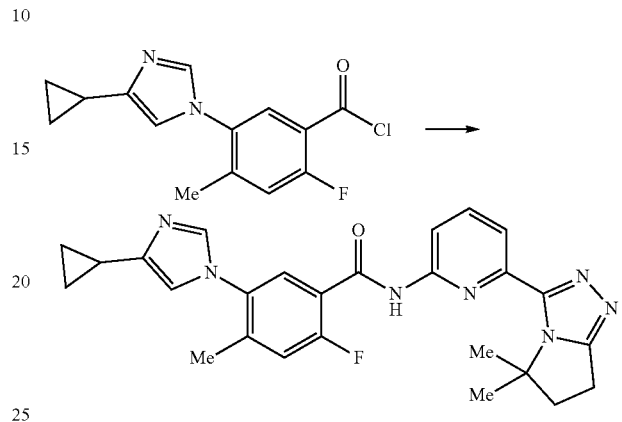

6-(5,5-Dimethyl-6,7-dihydro-5H-pyrrolo[2,1-c][1,2,4]triazol-3-yl)pyridin-2-amine (35 mg, 0.15 mmol) was added to a solution of 5-(4-cyclopropyl-1H-imidazol-1-yl)-2-fluoro-4-methylbenzoyl chloride (70 mg, 0.25 mmol) in THF (5 mL) and pyridine (5 mL) at room temperature, and then 4-dimethylaminopyridine (4.6 mg, 0.04 mmol) was added. The reaction solution was heated to 45° C., and stirred at this temperature for 2 hours. The reaction solution was added with water (5 mL) to quench the reaction, and extracted with dichloromethane (50 mL×2). The organic phase was washed with saturated brine, dried over anhydrous sodium sulfate, and concentrated. The residue was subjected to column chromatography to obtain the title compound 5-(4-cyclopropyl-1H-imidazol-1-yl)-N-(6-(5,5-dimethyl-6,7-dihydro-5H-pyrrolo[2,1-c][1,2,4]triazol-3-yl)pyridin-2-yl)-2-fluoro-4-methylbenzamide (39 mg, yield: 54%).

$^1$H NMR (400 MHz, CDCl$_3$) δ 9.05 (d, J=16.6 Hz, 1H), 8.29-8.27 (m, 1H), 8.09-7.94 (m, 2H), 7.82 (t, J=8.0 Hz, 1H), 7.44 (s, 1H), 7.12 (d, J=12.2 Hz, 1H), 6.73 (s, 1H), 3.10-2.86 (m, 2H), 2.60-2.45 (m, 2H), 2.22 (s, 3H), 1.88-1.82 (m, 1H), 1.72 (s, 6H), 0.87-0.82 (m, 2H), 0.78-0.75 (m, 2H);

MS m/z (ESI): 472.2 [M+H]$^+$.

Example 11

(S)-5-(4-Cyclopropyl-1H-imidazol-1-yl)-2-fluoro-N-(6-(5-(methoxymethyl)-6,7-dihydro-5H-pyrrolo[2,1-c][1,2,4]triazol-3-yl)pyridin-2-yl)-4-methylbenzamide

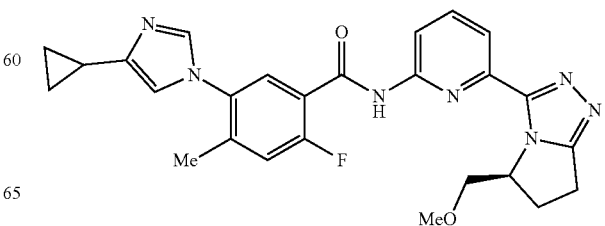

(S)-5-(4-Cyclopropyl-1H-imidazol-1-yl)-2-fluoro-N-(6-(5-(methoxymethyl)-6,7-di hydro-5H-pyrrolo[2,1-c][1,2,4]triazol-3-yl)pyridin-2-yl)-4-methylbenzamide was prepared in accordance with the method of Example 8.

$^1$H NMR (400 MHz, CDCl$_3$) δ 9.05 (d, J=15.6 Hz, 1H), 8.35 (m, 1H), 8.10 (m, 2H), 7.89 (t, J=8.0 Hz, 1H), 7.49 (s, 1H), 7.20 (d, J=12.4 Hz, 1H), 6.81 (m, 1H), 5.09-4.94 (m, 1H), 3.81 (m, 1H), 3.78-3.66 (m, 1H), 3.28 (s, 3H), 3.17-3.02 (m, 1H), 3.02-2.89 (m, 2H), 2.82-2.69 (m, 1H), 2.30 (s, 3H), 1.92 (m, 1H), 0.91 (m, 2H), 0.89-0.77 (m, 2H);

MS m/z (ESI): 488.2 [M+H]$^+$.

Example 12

(R)-5-(4-Cyclopropyl-1H-imidazol-1-yl)-2-fluoro-N-(6-(5-(methoxymethyl)-6,7-dihydro-5H-pyrrolo[2,1-c][1,2,4]triazol-3-yl)pyridin-2-yl)-4-methylbenzamide

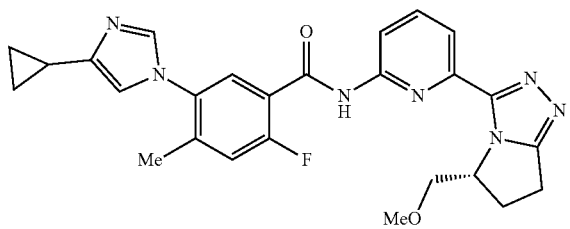 [SMILES: COC[C@H]1CCc2nnc(-c3cccc(NC(=O)c4cc(-n5cnc(C6CC6)c5)c(C)cc4F)n3)n21]

(R)-5-(4-Cyclopropyl-1H-imidazol-1-yl)-2-fluoro-N-(6-(5-(methoxy methyl)-6,7-di hydro-5H-pyrrolo[2,1-c][1,2,4]triazol-3-yl)pyridin-2-yl)-4-methylbenzamide was prepared in accordance with the method of Example 8.

$^1$H NMR (400 MHz, CDCl$_3$) δ 9.05 (d, J=15.6 Hz, 1H), 8.35 (m, 1H), 8.10 (m, 2H), 7.89 (t, J=8.0 Hz, 1H), 7.49 (s, 1H), 7.20 (d, J=12.4 Hz, 1H), 6.81 (m, 1H), 5.09-4.94 (m, 1H), 3.81 (m, 1H), 3.78-3.66 (m, 1H), 3.28 (s, 3H), 3.17-3.02 (m, 1H), 3.02-2.89 (m, 2H), 2.82-2.69 (m, 1H), 2.30 (s, 3H), 1.92 (m, 1H), 0.91 (m, 2H), 0.89-0.77 (m, 2H);

MS m/z (ESI): 488.2 [M+H]$^+$.

Example 13

(R)-2-Fluoro-5-(4-isopropyl-1H-imidazol-1-yl)-4-methyl-N-(6-(5-methyl-6,7-dihydro-5H-pyrrolo[2,1-c][1,2,4]triazol-3-yl)pyridin-2-yl)benzamide

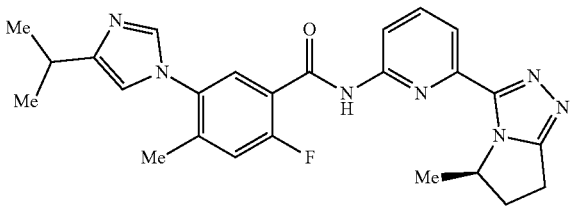 [SMILES: Cc1cc(F)c(C(=O)Nc2cccc(-c3nnc4n3[C@H](C)CC4)n2)cc1-n1cnc(C(C)C)c1]

(R)-2-Fluoro-5-(4-isopropyl-1H-imidazol-1-yl)-4-methyl-N-(6-(5-methyl-6,7-dihydro-5H-pyrrolo[2,1-c][1,2,4]triazol-3-yl)pyridin-2-yl)benzamide was prepared in accordance with the method of Example 8.

$^1$H NMR (400 MHz, CD$_3$OD) δ 9.22 (d, J=1.4 Hz, 1H), 8.45 (d, J=8.2 Hz, 1H), 8.10 (t, J=8.0 Hz, 1H), 8.05-7.97 (m, 2H), 7.66 (s, 1H), 7.50 (d, J=10.9 Hz, 1H), 5.57-5.45 (m, 1H), 3.47-3.36 (m, 1H), 3.28-3.16 (m, 3H), 2.65-2.57 (m, 1H), 2.36 (s, 3H), 1.59 (d, J=6.5 Hz, 3H), 1.43 (d, J=6.9 Hz, 6H);

MS m/z (ESI): 460.2 [M+H]$^+$.

Example 14

(S)-2-Fluoro-5-(4-isopropyl-1H-imidazol-1-yl)-4-methyl-N-(6-(5-methyl-6,7-dihydro-5H-pyrrolo[2,1-c][1,2,4]triazol-3-yl)pyridin-2-yl)benzamide

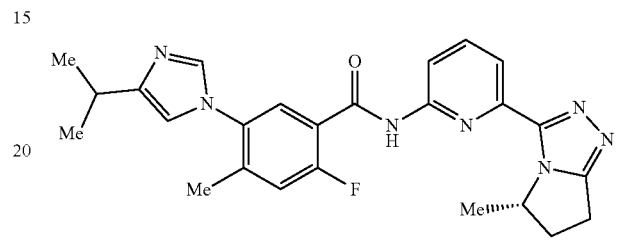

(S)-2-Fluoro-5-(4-isopropyl-1H-imidazol-1-yl)-4-methyl-N-(6-(5-methyl-6,7-dihydro-5H-pyrrolo[2,1-c][1,2,4]triazol-3-yl)pyridin-2-yl)benzamide was prepared in accordance with the method of Example 8.

$^1$H NMR (400 MHz, CD$_3$OD) δ 9.21 (s, 1H), 8.55-8.30 (m, 1H), 8.18-7.96 (m, 3H), 7.67 (s, 1H), 7.51 (d, J=9.8 Hz, 1H), 5.54-5.34 (m, 1H), 3.34 (s, 1H), 3.28-3.16 (m, 3H), 2.65-2.57 (m, 1H), 2.36 (s, 3H), 1.57 (d, J=5.8 Hz, 3H), 1.42 (d, J=6.9 Hz, 6H);

MS m/z (ESI): 460.2 [M+H]$^+$.

Example 15

(R)-5-(4-(tert-Butyl)-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide

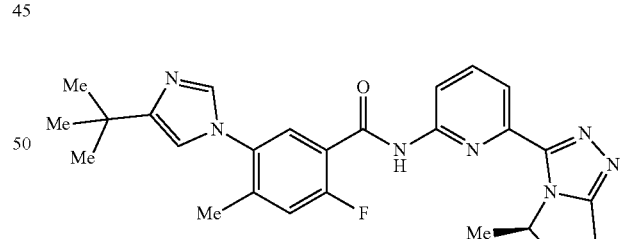

(R)-5-(4-(tert-Butyl)-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide was prepared in accordance with the method of Example 8.

$^1$H NMR (400 MHz, CD$_3$OD) δ 9.34 (s, 1H), 8.48 (d, J=8.3 Hz, 1H), 8.14 (t, J=7.9 Hz, 1H), 8.08-8.01 (m, 2H), 7.74 (s, 1H), 7.52 (d, J=10.8 Hz, 1H), 5.64 (s, 1H), 3.58-3.44 (m, 1H), 3.30-3.21 (m, 2H), 2.71-2.63 (m, 1H), 2.39 (s, 3H), 1.63 (d, J=5.5 Hz, 3H), 1.48 (s, 9H);

MS m/z (ESI): 474.2 [M+H]$^+$.

Example 16

(S)-5-(4-(tert-Butyl)-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide

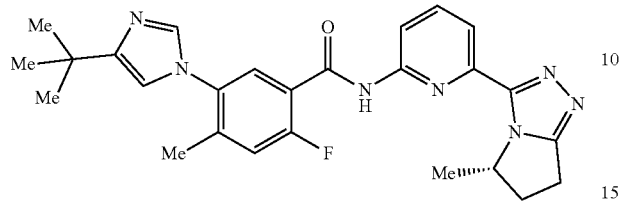

(S)-5-(4-(tert-Butyl)-1H-imidazol-1-yl)-2-fluoro-4-methyl-N-(6-(5-methyl-6,7-dihydro-5H-pyrrolo[2,1-c][1,2,4]triazol-3-yl)pyridin-2-yl)benzamide was prepared in accordance with the method of Example 8.
$^1$H NMR (400 MHz, CD$_3$OD) δ 9.34 (s, 1H), 8.48 (d, J=8.3 Hz, 1H), 8.14 (t, J=7.9 Hz, 1H), 8.08-8.01 (m, 2H), 7.74 (s, 1H), 7.52 (d, J=10.8 Hz, 1H), 5.64 (s, 1H), 3.58-3.44 (m, 1H), 3.30-3.21 (m, 2H), 2.71-2.63 (m, 1H), 2.39 (s, 3H), 1.63 (d, J=5.5 Hz, 3H), 1.48 (s, 9H);
MS m/z (ESI): 474.2 [M+H]$^+$.

Example 17

(S)-2-Fluoro-5-(4-isopropyl-1H-imidazol-1-yl)-N-(6-(5-(methoxymethyl)-6,7-dihydro-5H-pyrrolo[2,1-c][1,2,4]triazol-3-yl)pyridin-2-yl)-4-methylbenzamide

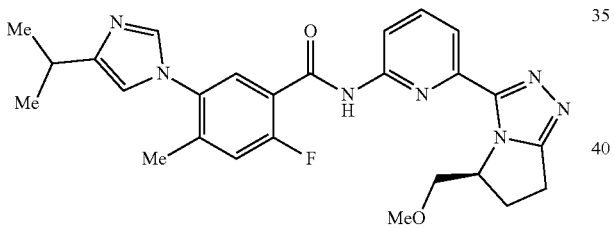

(S)-2-Fluoro-5-(4-isopropyl-1H-imidazol-1-yl)-N-(6-(5-(methoxymethyl)-6,7-dihydro-5H-pyrrolo[2,1-c][1,2,4]triazol-3-yl)pyridin-2-yl)-4-methylbenzamide was prepared in accordance with the method of Example 8.
MS m/z (ESI): 490.2 [M+H]$^+$.

Example 18

(R)-2-Fluoro-5-(4-isopropyl-1H-imidazol-1-yl)-N-(6-(5-(methoxymethyl)-6,7-dihydro-5H-pyrrolo[2,1-c][1,2,4]triazol-3-yl)pyridin-2-yl)-4-methylbenzamide

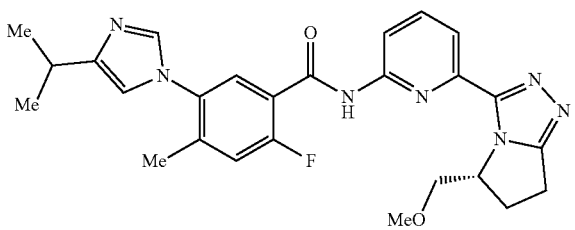 [SMILES: COC[C@H]1CCc2nnc(-c3cccc(NC(=O)c4cc(-n5cnc(C(C)C)c5)c(C)cc4F)n3)n21]

(R)-2-Fluoro-5-(4-isopropyl-1H-imidazol-1-yl)-N-(6-(5-(methoxymethyl)-6,7-dihydro-5H-pyrrolo[2,1-c][1,2,4]triazol-3-yl)pyridin-2-yl)-4-methylbenzamide was prepared in accordance with the method of Example 8.
MS m/z (ESI): 490.2 [M+H]$^+$.

Example 19

(S)-5-(4-(tert-Butyl)-1H-imidazol-1-yl)-2-fluoro-N-(6-(5-(methoxymethyl)-6,7-dihydro-5H-pyrrolo[2,1-c][1,2,4]triazol-3-yl)pyridin-2-yl)-4-methylbenzamide

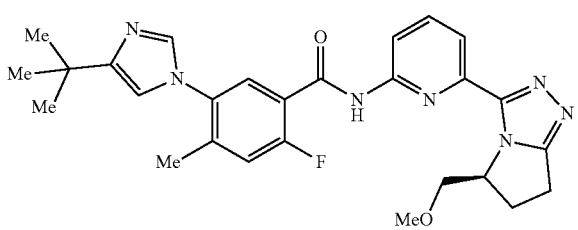 [SMILES: COC[C@@H]1CCc2nnc(-c3cccc(NC(=O)c4cc(-n5cnc(C(C)(C)C)c5)c(C)cc4F)n3)n21]

(S)-5-(4-(tert-Butyl)-1H-imidazol-1-yl)-2-fluoro-N-(6-(5-(methoxymethyl)-6,7-dihydro-5H-pyrrolo[2,1-c][1,2,4]triazol-3-yl)pyridin-2-yl)-4-methylbenzamide was prepared in accordance with the method of Example 8.
MS m/z (ESI): 504.2 [M+H]$^+$.

Example 20

(R)-5-(4-(tert-Butyl)-1H-imidazol-1-yl)-2-fluoro-N-(6-(5-(methoxymethyl)-6,7-dihydro-5H-pyrrolo[2,1-c][1,2,4]triazol-3-yl)pyridin-2-yl)-4-methylbenzamide

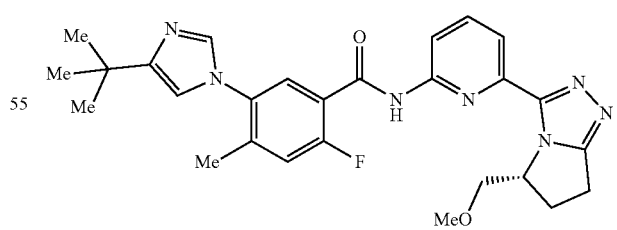

(R)-5-(4-(tert-Butyl)-1H-imidazol-1-yl)-2-fluoro-N-(6-(5-(methoxymethyl)-6,7-dihydro-5H-pyrrolo[2,1-c][1,2,4]triazol-3-yl)pyridin-2-yl)-4-methylbenzamide was prepared in accordance with the method of Example 8.
MS m/z (ESI): 504.2 [M+H]$^+$.

Example 21

(R)-2-Fluoro-4-methyl-N-(6-(5-methyl-6,7-dihydro-5H-pyrrolo[2,1-c][1,2,4]triazol-3-yl)pyridin-2-yl)-5-(4-(trifluoromethyl)-1H-imidazol-1-yl)benzamide

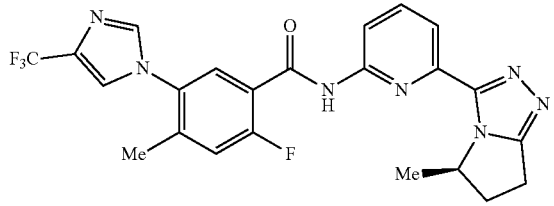 [SMILES: Cc1cc(F)c(C(=O)Nc2cccc(-c3nnc4n3[C@H](C)CC4)n2)cc1-n1cnc(C(F)(F)F)c1]

(R)-2-Fluoro-4-methyl-N-(6-(5-methyl-6,7-dihydro-5H-pyrrolo[2,1-c][1,2,4]triazol-3-yl)pyridin-2-yl)-5-(4-(trifluoromethyl)-1H-imidazol-1-yl)benzamide was prepared in accordance with the method of Example 8.
MS m/z (ESI): 486.2 [M+H]$^+$.

Example 22

(S)-2-Fluoro-4-methyl-N-(6-(5-methyl-6,7-dihydro-5H-pyrrolo[2,1-c][1,2,4]triazol-3-yl)pyridin-2-yl)-5-(4-(trifluoromethyl)-1H-imidazol-1-yl)benzamide

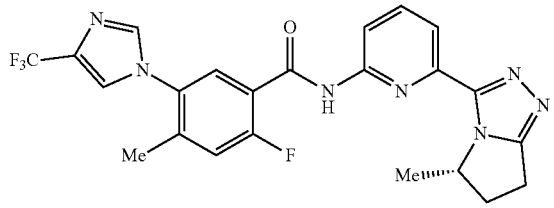 [SMILES: Cc1cc(F)c(C(=O)Nc2cccc(-c3nnc4n3[C@@H](C)CC4)n2)cc1-n1cnc(C(F)(F)F)c1]

(S)-2-Fluoro-4-methyl-N-(6-(5-methyl-6,7-dihydro-5H-pyrrolo[2,1-c][1,2,4]triazol-3-yl)pyridin-2-yl)-5-(4-(trifluoromethyl)-1H-imidazol-1-yl)benzamide was prepared in accordance with the method of Example 8.
MS m/z (ESI): 486.2 [M+H]$^+$.

Example 23

(R)-2-Fluoro-4-methyl-N-(6-(5-methyl-6,7-dihydro-5H-pyrrolo[2,1-c][1,2,4]triazol-3-yl)pyridin-2-yl)-5-(4-(oxetan-3-yl)-1H-imidazol-1-yl)benzamide

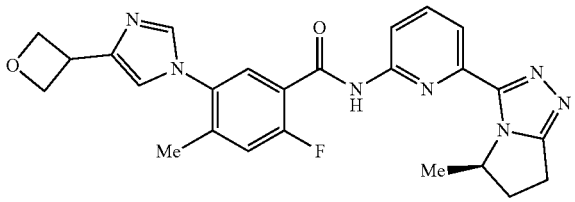 [SMILES: Cc1cc(F)c(C(=O)Nc2cccc(-c3nnc4n3[C@H](C)CC4)n2)cc1-n1cnc(C2COC2)c1]

(R)-2-Fluoro-4-methyl-N-(6-(5-methyl-6,7-dihydro-5H-pyrrolo[2,1-c][1,2,4]triazol-3-yl)pyridin-2-yl)-5-(4-(oxetan-3-yl)-1H-imidazol-1-yl)benzamide was prepared in accordance with the method of Example 8.
MS m/z (ESI): 474.2 [M+H]$^+$.

Example 24

(S)-2-Fluoro-4-methyl-N-(6-(5-methyl-6,7-dihydro-5H-pyrrolo[2,1-c][1,2,4]triazol-3-yl)pyridin-2-yl)-5-(4-(oxetan-3-yl)-1H-imidazol-1-yl)benzamide

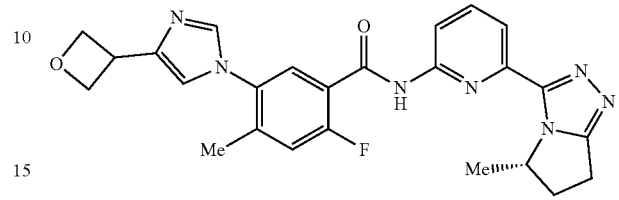

(S)-2-Fluoro-4-methyl-N-(6-(5-methyl-6,7-dihydro-5H-pyrrolo[2,1-c][1,2,4]triazol-3-yl)pyridin-2-yl)-5-(4-(oxetan-3-yl)-1H-imidazol-1-yl)benzamide was prepared in accordance with the method of Example 8.
MS m/z (ESI): 474.2 [M+H]$^+$.

Example 25

(R)-2-Fluoro-5-(4-(2-hydroxypropan-2-yl)-1H-imidazol-1-yl)-4-methyl-N-(6-(5-methyl-6,7-dihydro-5H-pyrrolo[2,1-c][1,2,4]triazol-3-yl)pyridin-2-yl)benzamide

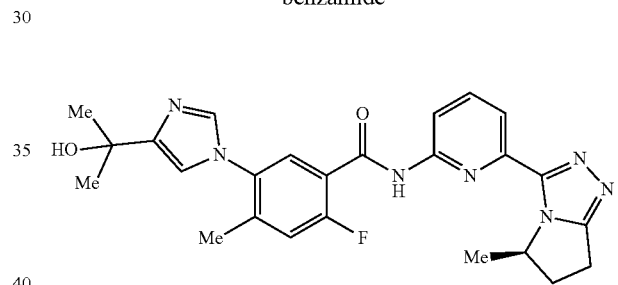

(R)-2-Fluoro-5-(4-(2-hydroxypropan-2-yl)-1H-imidazol-1-yl)-4-methyl-N-(6-(5-m ethyl-6,7-dihydro-5H-pyrrolo[2,1-c][1,2,4]triazol-3-yl)pyridin-2-yl)benzamide was prepared in accordance with the method of Example 8.
MS m/z (ESI): 476.2 [M+H]$^+$.

Example 26

(S)-2-Fluoro-5-(4-(2-hydroxypropan-2-yl)-1H-imidazol-1-yl)-4-methyl-N-(6-(5-methyl-6,7-dihydro-5H-pyrrolo[2,1-c][1,2,4]triazol-3-yl)pyridin-2-yl)benzamide

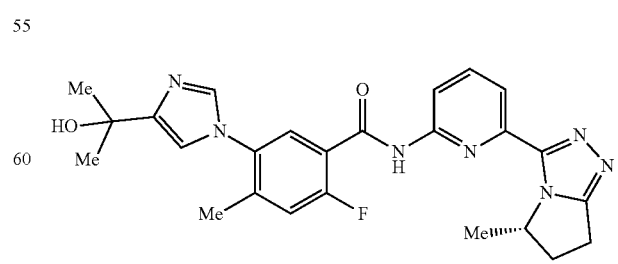

(S)-2-Fluoro-5-(4-(2-hydroxy propan-2-yl)-1H-imidazol-1-yl)-4-methyl-N-(6-(5-m ethyl-6,7-dihydro-5H-pyrrolo[2, 1-c][1,2,4]triazol-3-yl)pyridin-2-yl)benzamide was prepared in accordance with the method of Example 8.

MS m/z (ESI): 476.2 [M+H]+.

Example 27

N-(6-(7-acetyl-5,6,7,8-tetrahydro-[1,2,4]triazolo[4,3-a]pyrazin-3-yl)pyridine-2-yl)-5-(4-cyclopropyl-1H-imidazol-1-yl)-2-fluoro-4-methylbenzamide

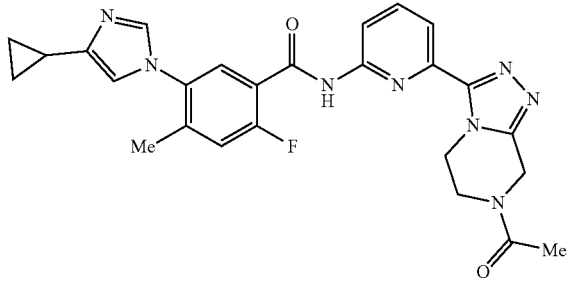 [SMILES: CC(=O)N1CCn2c(nnc2-c2cccc(NC(=O)c3cc(-n4cnc(C5CC5)c4)c(C)cc3F)n2)C1]

N-(6-(7-acetyl-5,6,7,8-tetrahydro-[1,2,4]triazolo[4,3-a]pyrazin-3-yl)pyridine-2-yl)-5-(4-cyclopropyl-1H-imidazol-1-yl)-2-fluoro-4-methylbenzamide was prepared in accordance with the method of Example 1.

$^1$H NMR (400 MHz, CDCl$_3$) δ 9.00 (d, J=15.0 Hz, 1H), 8.31 (m, 1H), 8.15-7.94 (m, 2H), 7.84 (t, J=8.0 Hz, 1H), 7.47-7.37 (m, 1H), 7.14 (m, 1H), 6.74 (s, 1H), 4.95 (m, 2H), 4.62-4.44 (m, 2H), 3.93 (m, 2H), 2.22 (s, 3H), 2.19 (s, 3H), 1.85 (m, 1H), 0.88-0.81 (m, 2H), 0.78-0.75 (m, 2H);

MS m/z (ESI): 501.2 [M+H]+.

Example 28

5-(4-Cyclopropyl-1H-imidazol-1-yl)-2-fluoro-4-methyl-N-(6-(7-methyl-6,7-dihydro-5H-pyrrolo[2,1-c][1,2,4]triazol-3-yl)pyridin-2-yl)benzamide

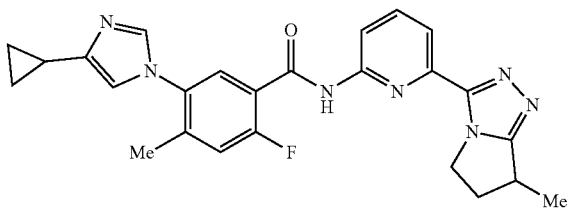 [SMILES: Cc1cc(F)c(C(=O)Nc2cccc(-c3nnc4n3CCC4C)n2)cc1-n1cnc(C2CC2)c1]

5-(4-Cyclopropyl-1H-imidazol-1-yl)-2-fluoro-4-methyl-N-(6-(7-methyl-6,7-dihydro-5H-pyrrolo[2,1-c][1,2,4]triazol-3-yl)pyridin-2-yl)benzamide was prepared in accordance with the method of Example 8.

$^1$H NMR (400 MHz, CD$_3$OD) δ 8.20 (d, J=8.1 Hz, 1H), 7.87 (t, J=7.9 Hz, 1H), 7.83-7.78 (m, 1H), 7.68-7.62 (m, 2H), 7.25 (d, J=11.2 Hz, 1H), 6.96 (s, 1H), 4.58-4.50 (m, 1H), 4.34-4.23 (m, 1H), 3.35-3.26 (m, 1H), 2.94-2.86 (m, 1H), 2.38-2.28 (m, 1H), 2.17 (s, 3H), 1.84-1.77 (m, 1H), 1.35 (d, J=7.0 Hz, 3H), 0.81-0.77 (m, 2H), 0.68-0.62 (m, 2H);

MS m/z (ESI): 458.2 [M+H]+.

Example 29

5-(4-Cyclopropyl-1H-imidazol-1-yl)-2-fluoro-N-(6-(6-methoxy-6,7-dihydro-5H-pyrrolo[2,1-c][1,2,4]triazol-3-yl)pyridin-2-yl)-4-methylbenzamide

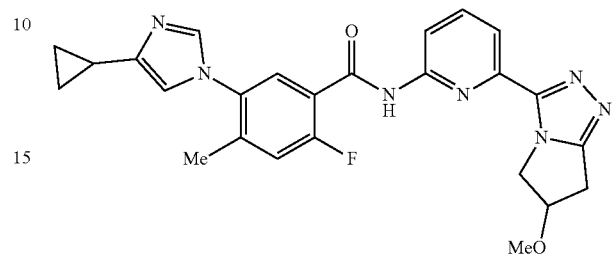

5-(4-Cyclopropyl-1H-imidazol-1-yl)-2-fluoro-N-(6-(6-methoxy-6,7-dihydro-5H-pyrrolo[2,1-c][1,2,4]triazol-3-yl)pyridin-2-yl)-4-methylbenzamide was prepared in accordance with the method of Example 8.

$^1$H NMR (400 MHz, CD$_3$OD) δ 9.11 (s, 1H), 8.35 (s, 1H), 8.11-7.90 (m, 3H), 7.60 (s, 1H), 7.50 (d, J=10.3 Hz, 1H), 4.71-4.62 (m, 2H), 3.46 (s, 3H), 3.39-3.35 (m, 2H), 3.15-3.03 (m, 1H), 2.35 (s, 3H), 2.13-2.06 (m, 1H), 1.19-1.13 (m, 2H), 0.97-0.88 (m, 2H);

MS m/z (ESI): 474.2 [M+H]+.

Example 30

5-(4-Cyclopropyl-1H-imidazol-1-yl)-N-(6-(6-cyclopropyl-6,7-dihydro-5H-pyrrolo[2,1-c][1,2,4]triazol-3-yl)pyridin-2-yl)-2-fluoro-4-methylbenzamide

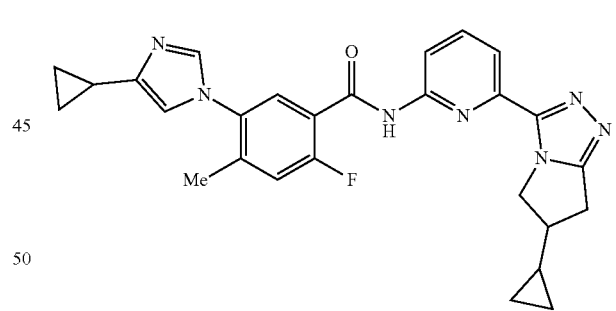

5-(4-Cyclopropyl-1H-imidazol-1-yl)-N-(6-(6-cyclopropyl-6,7-dihydro-5H-pyrrolo[2,1-c][1,2,4]triazol-3-yl)pyridin-2-yl)-2-fluoro-4-methylbenzamide was prepared in accordance with the method of Example 8.

$^1$H NMR (400 MHz, CD$_3$OD) δ 8.22 (d, J=8.1 Hz, 1H), 7.88 (t, J=7.9 Hz, 1H), 7.84-7.79 (m, 1H), 7.64 (d, J=6.6 Hz, 1H), 7.58 (d, J=1.2 Hz, 1H), 7.27 (d, J=11.1 Hz, 1H), 6.94 (d, J=1.1 Hz, 1H), 4.70-4.63 (m, 1H), 4.18-4.14 (m, 1H), 3.13-3.07 (m, 1H), 2.79-2.72 (m, 1H), 2.55-2.43 (m, 1H), 2.17 (s, 3H), 1.82-1.77 (m, 1H), 1.01-0.91 (m, 1H), 0.81-0.74 (m, 2H), 0.67-0.62 (m, 2H), 0.53-0.47 (m, 2H), 0.28-0.16 (m, 2H);

MS m/z (ESI): 484.2 [M+H]+.

Example 31

N-(6-(5'H,7'H-Spiro[cyclopropane-1,6'-pyrrolo[2,1-c][1,2,4]triazol]-3'-yl)pyridin-2-yl)-5-(4-cyclopropyl-1H-imidazol-1-yl)-2-fluoro-4-methylbenzamide

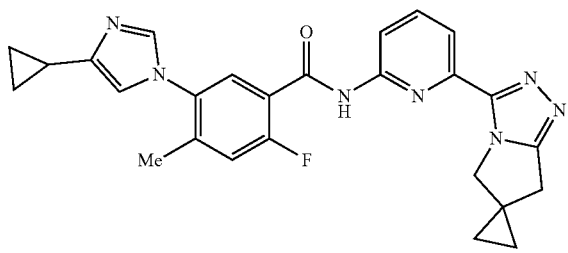 [SMILES: Cc1cc(F)c(C(=O)Nc2cccc(-c3nnc4n3CC3(CC3)C4)n2)cc1-n1cnc(C2CC2)c1]

N-(6-(5'H,7'H-Spiro[cyclopropane-1,6'-pyrrolo[2,1-c][1,2,4]triazol]-3'-yl)pyridin-2-yl)-5-(4-cyclopropyl-1H-imidazol-1-yl)-2-fluoro-4-methylbenzamide was prepared in accordance with the method of Example 8.
MS m/z (ESI): 470.2 [M+H]+.

Example 32

5-(4-Cyclopropyl-1H-imidazol-1-yl)-N-(6-(6,6-dimethyl-6,7-dihydro-5H-pyrrolo[2,1-c][1,2,4]triazol-3-yl)pyridin-2-yl)-2-fluoro-4-methylbenzamide

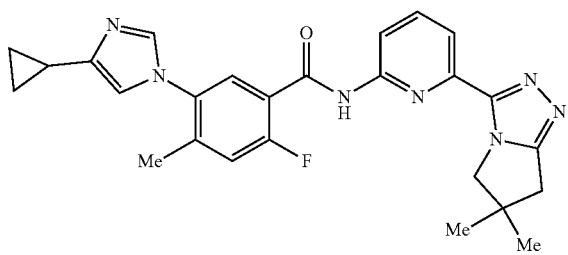 [SMILES: Cc1cc(F)c(C(=O)Nc2cccc(-c3nnc4n3CC(C)(C)C4)n2)cc1-n1cnc(C2CC2)c1]

5-(4-Cyclopropyl-1H-imidazol-1-yl)-N-(6-(6,6-dimethyl-6,7-dihydro-5H-pyrrolo[2,1-c][1,2,4]triazol-3-yl)pyridin-2-yl)-2-fluoro-4-methylbenzamide was prepared in accordance with the method of Example 8.
$^1$H NMR (400 MHz, CD$_3$OD) δ 8.36-8.28 (m, 2H), 8.00-7.86 (m, 2H), 7.77 (d, J=5.9 Hz, 1H), 7.37 (d, J=10.8 Hz, 1H), 7.12 (s, 1H), 4.31 (s, 2H), 2.87 (s, 2H), 2.29 (s, 3H), 1.97-1.88 (m, 1H), 1.35 (s, 6H), 0.96-0.89 (m, 2H), 0.80-0.74 (m, 2H); MS m/z (ESI): 472.2 [M+H]+.

Example 33

5-(4-Cyclopropyl-1H-imidazol-1-yl)-2-fluoro-4-methyl-N-(6-(6-methyl-6,7-dihydro-5H-pyrrolo[2,1-c][1,2,4]triazol-3-yl)pyridin-2-yl)benzamide

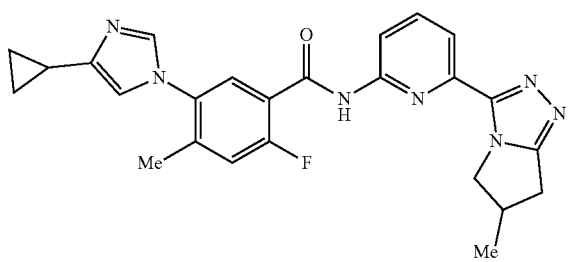 [SMILES: Cc1cc(F)c(C(=O)Nc2cccc(-c3nnc4n3CC(C)C4)n2)cc1-n1cnc(C2CC2)c1]

5-(4-Cyclopropyl-1H-imidazol-1-yl)-2-fluoro-4-methyl-N-(6-(6-methyl-6,7-dihydro-5H-pyrrolo[2,1-c][1,2,4]triazol-3-yl)pyridin-2-yl)benzamide was prepared in accordance with the method of Example 8.
$^1$H NMR (400 MHz, CD$_3$OD) δ 9.21 (s, 1H), 8.48 (d, J=8.3 Hz, 1H), 8.13 (t, J=8.0 Hz, 1H), 8.05-7.98 (m, 2H), 7.66 (s, 1H), 7.50 (d, J=10.7 Hz, 1H), 5.11-5.07 (m, 1H), 4.40-3.35 (m, 1H), 3.59-3.47 (m, 2H), 3.07-2.94 (m, 1H), 2.37 (s, 3H), 2.13-2.06 (m, 1H), 1.43 (d, J=5.5 Hz, 3H), 1.21-1.14 (m, 2H), 1.00-0.88 (m, 2H);
MS m/z (ESI): 458.2 [M+H]+.

Example 34

(R)-5-(4-Cyclopropyl-1H-imidazol-1-yl)-2-fluoro-4-methyl-N-(6-(6-methyl-6,7-dihydro-5H-pyrrolo[2,1-c][1,2,4]triazol-3-yl)pyridin-2-yl)benzamide

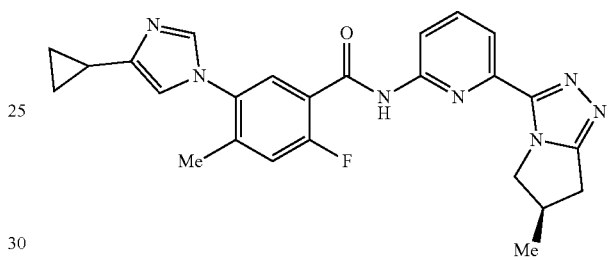

(R)-5-(4-Cyclopropyl-1H-imidazol-1-yl)-2-fluoro-4-methyl-N-(6-(6-methyl-6,7-di hydro-5H-pyrrolo[2,1-c][1,2,4]triazol-3-yl)pyridin-2-yl)benzamide was prepared in accordance with the method of Example 8.
$^1$H NMR (400 MHz, CD$_3$OD) δ 9.21 (s, 1H), 8.48 (d, J=8.3 Hz, 1H), 8.13 (t, J=8.0 Hz, 1H), 8.05-7.98 (m, 2H), 7.66 (s, 1H), 7.50 (d, J=10.7 Hz, 1H), 5.11-5.07 (m, 1H), 4.40-3.35 (m, 1H), 3.59-3.47 (m, 2H), 3.07-2.94 (m, 1H), 2.37 (s, 3H), 2.13-2.06 (m, 1H), 1.43 (d, J=5.5 Hz, 3H), 1.21-1.14 (m, 2H), 1.00-0.88 (m, 2H);
MS m/z (ESI): 458.2 [M+H]+.

Example 35

(R)-5-(4-Cyclopropyl-1H-imidazol-1-yl)-2-fluoro-4-methyl-N-(6-(6-methyl-6,7-dihydro-5H-pyrrolo[2,1-c][1,2,4]triazol-3-yl)pyridin-2-yl)benzamide

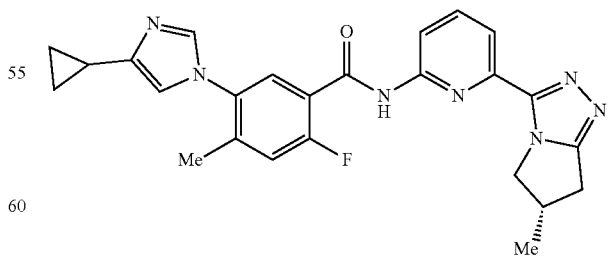

(S)-5-(4-Cyclopropyl-1H-imidazol-1-yl)-2-fluoro-4-methyl-N-(6-(6-methyl-6,7-di hydro-5H-pyrrolo[2,1-c][1,2,4]triazol-3-yl)pyridin-2-yl)benzamide was prepared in accordance with the method of Example 8.

¹H NMR (400 MHz, CD₃OD) δ 9.21 (s, 1H), 8.48 (d, J=8.3 Hz, 1H), 8.13 (t, J=8.0 Hz, 1H), 8.05-7.98 (m, 2H), 7.66 (s, 1H), 7.50 (d, J=10.7 Hz, 1H), 5.11-5.07 (m, 1H), 4.40-3.35 (m, 1H), 3.59-3.47 (m, 2H), 3.07-2.94 (m, 1H), 2.37 (s, 3H), 2.13-2.06 (m, 1H), 1.43 (d, J=5.5 Hz, 3H), 1.21-1.14 (m, 2H), 1.00-0.88 (m, 2H);

MS m/z (ESI): 458.2 [M+H]⁺.

Example 36

5-(4-Cyclopropyl-1H-imidazol-1-yl)-2-fluoro-N-(6-((R)-5-((R)-1-methoxyethyl)-6,7-di hydro-5H-pyrrolo[2,1-c][1,2,4]triazol-3-yl)pyridin-2-yl)-4-methylbenzamide

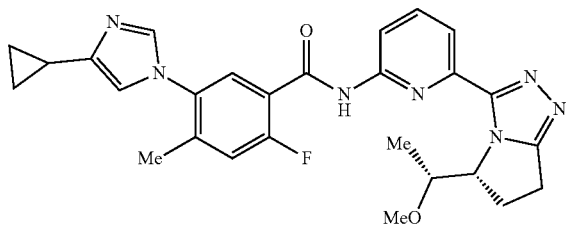 [SMILES: CO[C@H](C)[C@H]1CCc2nnc(-c3cccc(NC(=O)c4cc(-n5cnc(C6CC6)c5)c(C)cc4F)n3)n21]

5-(4-Cyclopropyl-1H-imidazol-1-yl)-2-fluoro-N-(6-((R)-5-((R)-1-methoxyethyl)-6,7-dihydro-5H-pyrrolo[2,1-c][1,2,4]triazol-3-yl)pyridin-2-yl)-4-methylbenzamide was prepared in accordance with the method of Example 8.

¹H NMR (400 MHz, CDCl₃) δ 8.96 (d, J=15.6 Hz, 1H), 8.31 (m, 1H), 8.01 (m, 2H), 7.83 (t, J=8.0 Hz, 1H), 7.41 (s, 1H), 7.12 (d, J=12.6 Hz, 1H), 6.73 (s, 1H), 5.08 (m, 1H), 4.03-3.92 (m, 1H), 3.36 (s, 3H), 2.96-2.87 (m, 2H), 2.87-2.64 (m, 3H), 2.21 (s, 3H), 0.85-0.79 (m, 7H);

MS m/z (ESI): 502.2 [M+H]⁺.

Example 37

(S)-5-(4-Cyclopropyl-1H-imidazol-1-yl)-2-fluoro-4-methyl-N-(6-(5-vinyl-6,7-dihydro-5H-pyrrolo[2,1-c][1,2,4]triazol-3-yl)pyridin-2-yl)benzamide

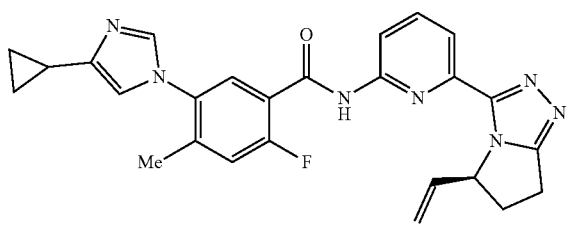 [SMILES: C=C[C@@H]1CCc2nnc(-c3cccc(NC(=O)c4cc(-n5cnc(C6CC6)c5)c(C)cc4F)n3)n21]

(S)-5-Vinylpyrrolidin-2-one was prepared according to *J. Org. Chem.*, 2017, 82, 532-540.

MS m/z (ESI): 112.2 [M+H]⁺.

Step 1: Preparation of (S)-5-methoxy-2-vinyl-3,4-dihydro-2H-pyrrole

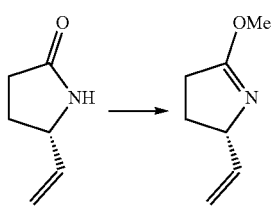

(S)-5-Vinylpyrrolidin-2-one (0.26 g, 2.34 mmol) was dissolved in dichloromethane (60 mL) in an ice bath, and then trimethyloxonium tetrafluoroborate (0.48 g, 3.28 mmol) was added in batches. The reaction solution was warmed up to room temperature slowly, and stirred at this temperature for 5 hours. The reaction solution was added with saturated aqueous NaHCO₃ solution (5 mL), and extracted with dichloromethane (50 mL×2). The organic phase was washed with saturated brine, dried over anhydrous sodium sulfate, added with glacial acetic acid (5 mL), concentrated under reduced pressure to remove the organic solvent and obtain the crude product, which was used directly in the next step.

MS m/z (ESI): 126.1 [M+H]⁺.

Step 2: Preparation of (S)-6-(5-vinyl-6,7-dihydro-5H-pyrrolo[2,1-c][1,2,4]triazol-3-yl)pyridin-2-amine

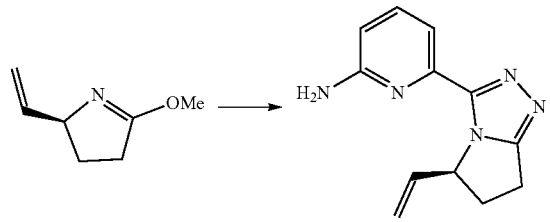

6-Aminopicolinohydrazide (321 mg, 2.11 mmol) was dissolved in a mixed solvent of 2-pentanol (10 mL) and acetic acid (1 mL) at room temperature, and then (S)-5-methoxy-2-vinyl-3,4-dihydro-2H-pyrrole (293 mg, 2.34 mmol) was added. The reaction solution was heated to 125° C., and stirred at this temperature for 12 hours. After cooling to room temperature, the reaction solution was concentrated under reduced pressure to remove the organic solvent. The residue was added with saturated aqueous NaHCO₃ solution (5 mL), and extracted with dichloromethane (50 mL×2). The organic phase was washed with saturated brine, dried over anhydrous sodium sulfate, and concentrated to remove the organic solvent. The residue was subjected to column chromatography to obtain the title compound (S)-6-(5-vinyl-6,7-dihydro-5H-pyrrolo[2,1-c][1,2,4]triazol-3-yl)pyridin-2-amine (240 mg, yield of two steps: 50%).

MS m/z (ESI): 228.1 [M+H]⁺.

Step 3: Preparation of (S)-5-(4-cyclopropyl-1H-imidazol-1-yl)-2-fluoro-4-methyl-N-(6-(5-vinyl-6,7-dihydro-5H-pyrrolo[2,1-c][1,2,4]triazol-3-yl)pyridin-2-yl)benzamide

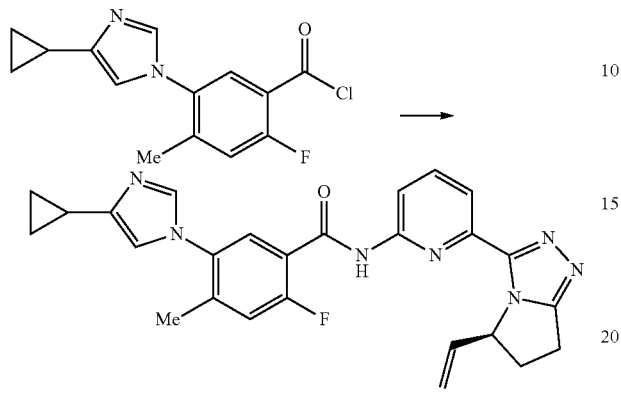

(S)-6-(5-Vinyl-6,7-dihydro-5H-pyrrolo[2,1-c][1,2,4]triazol-3-yl)pyridin-2-amine (44 mg, 0.19 mmol) was added to a solution of 5-(4-cyclopropyl-1H-imidazol-1-yl)-2-fluoro-4-methylbenzoyl chloride (90 mg, 0.33 mmol) in THF (5 mL) and pyridine (5 mL) at room temperature, and then 4-dimethylaminopyridine (5.9 mg, 0.048 mmol) was added. The reaction solution was heated to 45° C., and stirred at this temperature for 2 hours. The reaction solution was added dropwise with water (5 mL), and extracted with dichloromethane (50 mL×2). The organic phase was washed with saturated brine, dried over anhydrous sodium sulfate, and concentrated to remove the organic solvent. The residue was subjected to column chromatography to obtain the title compound (S)-5-(4-cyclopropyl-1H-imidazol-1-yl)-2-fluoro-4-methyl-N-(6-(5-vinyl-6,7-dihydro-5H-pyrrolo[2,1-c][1,2,4]triazol-3-yl)pyridin-2-yl)benzamide (53 mg, yield 58%).

$^1$H NMR (400 MHz, CD$_3$OD) δ 9.08 (s, 1H), 8.36 (d, J=8.4 Hz, 1H), 8.02-7.97 (m, 1H), 7.90-7.85 (m, 2H), 7.50 (s, 1H), 7.40-7.38 (m, 1H), 6.00-5.95 (m, 2H), 5.26-5.22 (m, 1H), 5.16-5.13 (m, 1H), 3.39-3.31 (m, 1H), 3.24-3.20 (m, 2H), 2.68-2.60 (m, 1H), 2.22 (s, 3H), 2.03-1.95 (m, 1H), 1.07-1.02 (m, 2H), 0.87-0.82 (m, 2H);

MS m/z (ESI): 470.1 [M+H]$^+$.

Example 38

(S)-5-(4-Cyclopropyl-1H-imidazol-1-yl)-2-fluoro-4-methyl-N-(6-(5-vinyl-6,7-dihydro-5H-pyrrolo[2,1-c][1,2,4]triazol-3-yl)pyridin-2-yl)benzamide

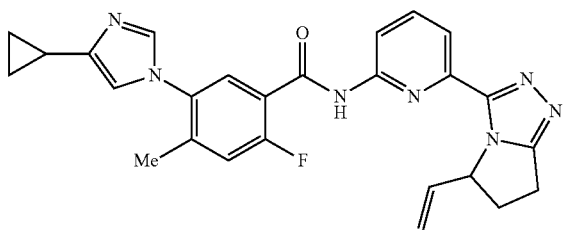 [SMILES: C=CC1CCc2nnc(-c3cccc(NC(=O)c4cc(-n5cnc(C6CC6)c5)c(C)cc4F)n3)n21]

5-(4-Cyclopropyl-1H-imidazol-1-yl)-2-fluoro-4-methyl-N-(6-(5-vinyl-6,7-dihydro-5H-pyrrolo[2,1-c][1,2,4]triazol-3-yl)pyridin-2-yl)benzamide was prepared in accordance with Example 37.

$^1$H NMR (400 MHz, CD$_3$OD) δ 9.08 (s, 1H), 8.36 (d, J=8.4 Hz, 1H), 8.02-7.97 (m, 1H), 7.90-7.85 (m, 2H), 7.50 (s, 1H), 7.40-7.38 (m, 1H), 6.00-5.95 (m, 2H), 5.26-5.22 (m, 1H), 5.16-5.13 (m, 1H), 3.39-3.31 (m, 1H), 3.24-3.20 (m, 2H), 2.68-2.60 (m, 1H), 2.22 (s, 3H), 2.03-1.95 (m, 1H), 1.07-1.02 (m, 2H), 0.87-0.82 (m, 2H);

MS m/z (ESI): 470.1 [M+H]$^+$.

Example 39

(R)-5-(4-Cyclopropyl-1H-imidazol-1-yl)-2-fluoro-4-methyl-N-(6-(5-vinyl-6,7-dihydro-5H-pyrrolo[2,1-c][1,2,4]triazol-3-yl)pyridin-2-yl)benzamide

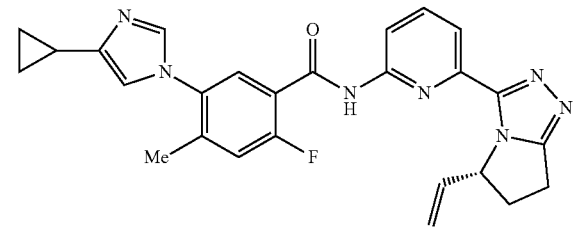 [SMILES: C=C[C@H]1CCc2nnc(-c3cccc(NC(=O)c4cc(-n5cnc(C6CC6)c5)c(C)cc4F)n3)n21]

(R)-5-(4-Cyclopropyl-1H-imidazol-1-yl)-2-fluoro-4-methyl-N-(6-(5-vinyl-6,7-dihydro-5H-pyrrolo[2,1-c][1,2,4]triazol-3-yl)pyridin-2-yl)benzamide was prepared in accordance with Example 37.

$^1$H NMR (400 MHz, CD$_3$OD) δ 9.08 (s, 1H), 8.36 (d, J=8.4 Hz, 1H), 8.02-7.97 (m, 1H), 7.90-7.85 (m, 2H), 7.50 (s, 1H), 7.40-7.38 (m, 1H), 6.00-5.95 (m, 2H), 5.26-5.22 (m, 1H), 5.16-5.13 (m, 1H), 3.39-3.31 (m, 1H), 3.24-3.20 (m, 2H), 2.68-2.60 (m, 1H), 2.22 (s, 3H), 2.03-1.95 (m, 1H), 1.07-1.02 (m, 2H), 0.87-0.82 (m, 2H);

MS m/z (ESI): 470.1 [M+H]$^+$.

Example 40

(S)-5-(4-Cyclopropyl-1H-imidazol-1-yl)-2-fluoro-4-methyl-N-(6-(5-(trifluoromethyl)-6,7-dihydro-5H-pyrrolo[2,1-c][1,2,4]triazol-3-yl)pyridin-2-yl)benzamide

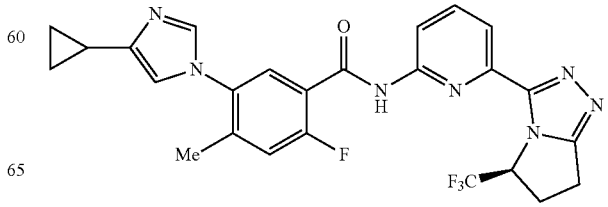

Step 1: Preparation of (S)-5-methoxy-2-(trifluoromethyl)-3,4-dihydro-2H-pyrrole

(S)-5-(Trifluoromethyl)pyrrolidin-2-one (0.6 g, 3.92 mmol) was dissolved in dichloromethane (40 mL) in an ice bath, and then trimethyloxonium tetrafluoroborate (0.81 g, 5.5 mmol) was added in batches. The reaction solution was warmed up to room temperature slowly, and stirred at this temperature for 5 hours. The reaction solution was added with saturated aqueous NaHCO$_3$ solution (5 mL), and extracted with dichloromethane (50 mL×2). The organic phase was washed with saturated brine, dried over anhydrous sodium sulfate, added with glacial acetic acid (5 mL), and concentrated under reduced pressure to remove the organic solvent and obtain the crude product, which was used directly in the next step.

MS m/z (ESI): 168.2 [M+H]$^{-1}$.

Step 2: Preparation of (S)-6-(5-(trifluoromethyl)-6,7-dihydro-5H-pyrrolo[2,1-c][1,2,4]triazol-3-yl)pyridin-2-amine

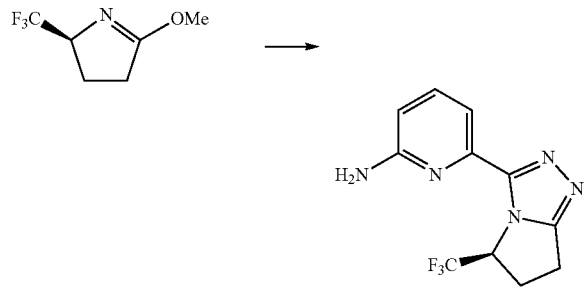

6-Aminopicolinohydrazide (620 mg, 3.71 mmol) was dissolved in 2-pentanol (15 mL) and acetic acid (1 mL) at room temperature, and then (S)-5-methoxy-2-(trifluoromethyl)-3,4-dihydro-2H-pyrrole (650 mg, 3.89 mmol) was added. The reaction solution was heated to 125° C., and stirred at this temperature for 12 hours. After cooling to room temperature, the reaction solution was concentrated under reduced pressure. The residue was added with saturated aqueous NaHCO$_3$ solution (5 mL), and extracted with dichloromethane (50 mL×2). The organic phase was washed with saturated brine, dried over anhydrous sodium sulfate, and concentrated to remove the organic solvent. The residue was subjected to column chromatography to obtain the title compound (S)-6-(5-(trifluoromethyl)-6,7-dihydro-5H-pyrrolo[2,1-c][1,2,4]triazol-3-yl)pyridin-2-amine (560 mg, yield of two steps: 56%).

MS m/z (ESI): 270.2 [M+H]$^+$.

Step 3: Preparation of (S)-5-(4-cyclopropyl-1H-imidazol-1-yl)-2-fluoro-4-methyl-N-(6-(5-(trifluoromethyl)-6,7-dihydro-5H-pyrrolo[2,1-c][1,2,4]triazol-3-yl)pyridin-2-yl)benzamide

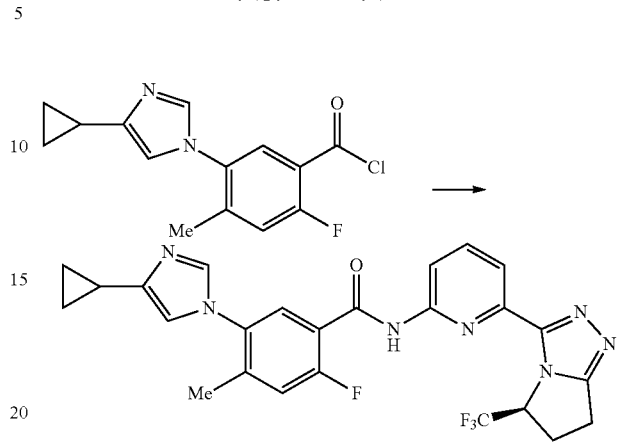

(S)-6-(5-(Trifluoromethyl)-6,7-dihydro-5H-pyrrolo[2,1-c][1,2,4]triazol-3-yl)pyridin-2-amine (43 mg, 0.22 mmol) was added to a solution of 5-(4-cyclopropyl-1H-imidazol-1-yl)-2-fluoro-4-methylbenzoyl chloride (100 mg, 0.36 mmol) in THF (5 mL) and pyridine (5 mL) at room temperature, and then 4-dimethylaminopyridine (11 mg, 0.09 mmol) was added. The reaction solution was heated to 45° C., and stirred at this temperature for 2 hours. The reaction solution was added with water (5 mL) to quench the reaction, and extracted with dichloromethane (50 mL×2). The organic phase was washed with saturated brine, dried over anhydrous sodium sulfate, and concentrated to remove the organic solvent. The residue was subjected to column chromatography to obtain the title compound (S)-5-(4-cyclopropyl-1H-imidazol-1-yl)-2-fluoro-4-methyl-N-(6-(5-(trifluoromethyl)-6,7-dihydro-5H-pyrrolo[2,1-c][1,2,4]triazol-3-yl)pyridin-2-yl)benzamide (51 mg, yield 62%).

$^1$H NMR (400 MHz, CDCl$_3$) δ 8.99 (d, J=15.6 Hz, 1H), 8.32-8.30 (m, 1H), 8.01-7.98 (m, 2H), 7.83 (t, J=8.0 Hz, 1H), 7.53 (s, 1H), 7.12 (d, J=13.6 Hz, 1H), 6.74 (s, 1H), 5.56-5.51 (m, 1H), 3.21-3.01 (m, 3H), 2.92-2.85 (m, 1H), 2.21 (s, 3H), 1.89-1.82 (m, 1H), 0.89-0.81 (m, 4H);

MS m/z (ESI): 512.2 [M+H]$^+$.

Example 41

5-(4-Cyclopropyl-1H-imidazol-1-yl)-2-fluoro-4-methyl-N-(6-(5-(trifluoromethyl)-6,7-di hydro-5H-pyrrolo[2,1-c][1,2,4]triazol-3-yl)pyridin-2-yl)benzamide

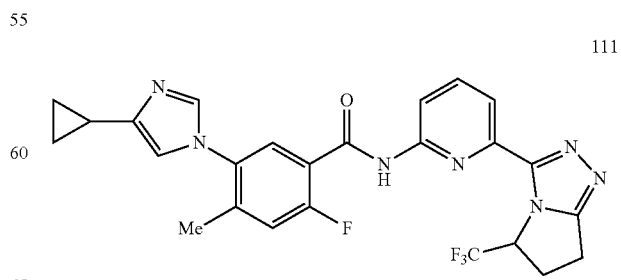

5-(4-Cyclopropyl-1H-imidazol-1-yl)-2-fluoro-4-methyl-N-(6-(5-(trifluoromethyl)-6,7-dihydro-5H-pyrrolo[2,1-c][1, 2,4]triazol-3-yl)pyridin-2-yl)benzamide was prepared in accordance with Example 40.

$^1$H NMR (400 MHz, CDCl$_3$) δ 8.99 (d, J=15.6 Hz, 1H), 8.32-8.30 (m, 1H), 8.01-7.98 (m, 2H), 7.83 (t, J=8.0 Hz, 1H), 7.53 (s, 1H), 7.12 (d, J=13.6 Hz, 1H), 6.74 (s, 1H), 5.56-5.51 (m, 1H), 3.21-3.01 (m, 3H), 2.92-2.85 (m, 1H), 2.21 (s, 3H), 1.89-1.82 (m, 1H), 0.89-0.81 (m, 4H);

MS m/z (ESI): 512.2 [M+H]$^+$.

Example 42

(R)-5-(4-Cyclopropyl-1H-imidazol-1-yl)-2-fluoro-4-methyl-N-(6-(5-(trifluoromethyl)-6,7-dihydro-5H-pyrrolo[2,1-c][1,2,4]triazol-3-yl)pyridin-2-yl)benzamide

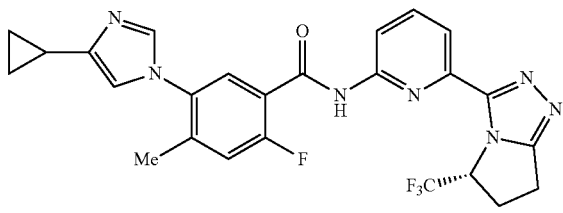 [SMILES: Cc1cc(F)c(C(=O)Nc2cccc(-c3nnc4n3[C@@H](C(F)(F)F)CC4)n2)cc1-n1cnc(C2CC2)c1]

(R)-5-(4-Cyclopropyl-1H-imidazol-1-yl)-2-fluoro-4-methyl-N-(6-(5-(trifluoromethyl)-6,7-dihydro-5H-pyrrolo[2,1-c][1,2,4]triazol-3-yl)pyridin-2-yl)benzamide was prepared in accordance with Example 40.

$^1$H NMR (400 MHz, CDCl$_3$) δ 8.99 (d, J=15.6 Hz, 1H), 8.32-8.30 (m, 1H), 8.01-7.98 (m, 2H), 7.83 (t, J=8.0 Hz, 1H), 7.53 (s, 1H), 7.12 (d, J=13.6 Hz, 1H), 6.74 (s, 1H), 5.56-5.51 (m, 1H), 3.21-3.01 (m, 3H), 2.92-2.85 (m, 1H), 2.21 (s, 3H), 1.89-1.82 (m, 1H), 0.89-0.81 (m, 4H);

MS m/z (ESI): 512.2 [M+H]$^+$.

Example 43

(S)-5-(4-Cyclopropyl-1H-imidazol-1-yl)-N-(6-(5-ethynyl-6,7-dihydro-5H-pyrrolo[2,1-c][1,2,4]triazol-3-yl)pyridin-2-yl)-2-fluoro-4-methylbenzamide

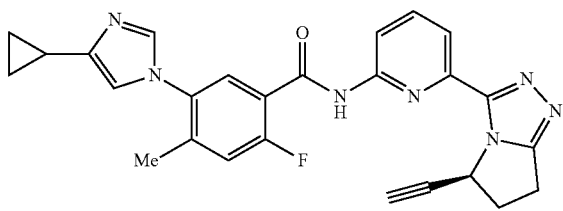 [SMILES: C#C[C@@H]1CCc2nnc(-c3cccc(NC(=O)c4cc(-n5cnc(C6CC6)c5)c(C)cc4F)n3)n21]

tert-Butyl (S)-2-formyl-5-oxopyrrolidin-1-carboxylate was prepared in accordance with *Org. Lett.* 2011, 13, 2634-2637.

Step 1: Preparation of S-ethyl (S)-5-oxopyrrolidine-2-carbothioate

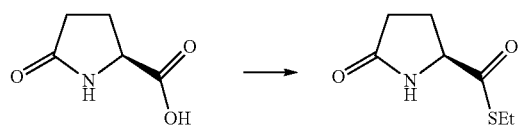

(S)-5-Oxopyrrolidine-2-carboxylic acid (20 g, 150 mmol) was dissolved in CH$_2$Cl$_2$ (300 mL) and DMF (160 mL) in an ice bath, and then DMAP (1.85 g, 15.0 mmol), ethanethiol (13.8 mL, 180 mmol) and DCC (40.5 g, 180 mmol) were added successively. The reaction solution was warmed up to room temperature slowly, and stirred at this temperature for 16 hours. The reaction solution was added with saturated aqueous NaHCO$_3$ solution (20 mL), and extracted with dichloromethane (100 mL×2). The organic phase was washed with saturated brine, dried over anhydrous sodium sulfate, and concentrated under reduced pressure. The residue was subjected to column chromatography to obtain the title compound S-ethyl (S)-5-oxopyrrolidine-2-carbothioate (18.5 g, 69%).

MS m/z (ESI): 174.1 [M+H]$^+$.

Step 2: Preparation of tert-butyl (S)-2-((ethylthio)carbonyl)-5-oxopyrrolidine-1-carboxylate

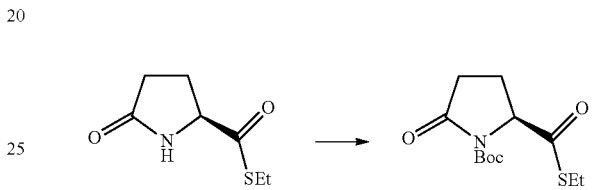

S-Ethyl (S)-5-oxopyrrolidine-2-carbothioate (6 g, 34.6 mmol) was dissolved in MeCN (35 mL) in an ice bath, and then Boc$_2$O (8.28 mL, 35.0 mmol) and DMAP (470 mg, 3.46 mmol) were added successively. The reaction solution was warmed up to room temperature slowly, and stirred at this temperature for 2 hours. The reaction solution was added with saturated aqueous NaHCO$_3$ solution (20 mL), and extracted with ethyl acetate (100 mL×2). The organic phase was washed with saturated brine, dried over anhydrous sodium sulfate, and concentrated under reduced pressure. The residue was subjected to column chromatography to obtain the title compound S-ethyl (S)-5-oxopyrrolidine-2-carbothioate (7.3 g, 77%).

MS m/z (ESI): 296.1 [M+Na]$^+$.

Step 3: Preparation of tert-butyl (S)-2-formyl-5-oxopyrrolidine-1-carboxylate

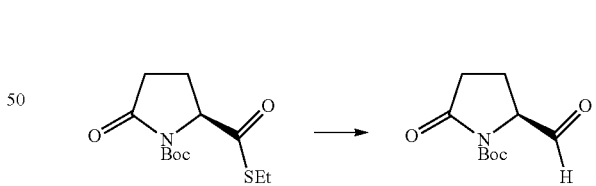

S-Ethyl (S)-5-oxopyrrolidine-2-carbothioate (1.0 g, 3.66 mmol) was dissolved in acetone (15 mL) in an ice bath, and then Pd/C (160 mg) and EtSiH (1.28 g, 10.98 mmol) were added successively. The reaction solution was warmed up to room temperature slowly, stirred at this temperature for 1 hour, and filtrated through celite. The filtrate was concentrated under reduced pressure to obtain an oily product (0.72 g), which was used directly in the next step.

$^1$H NMR (400 MHz, CDCl$_3$) δ 9.58 (s, 1H), 4.63-4.41 (m, 1H), 2.54-2.48 (m, 2H), 2.28-2.15 (m, 1H), 2.07-2.01 (m, 1H), 1.46 (s, 9H);

MS m/z (ESI): 214.1 [M+H]$^+$.

Step 4: Preparation of (S)-5-oxopyrrolidine-2-carbaldehyde

tert-Butyl (S)-2-formyl-5-oxopyrrolidine-1-carboxylate (0.72 g, 3.38 mmol) was dissolved in $CH_2Cl_2$ (10 mL) in an ice bath, and then TFA (2.5 mL) was added. The reaction solution was warmed up to room temperature slowly, and stirred at this temperature for 2 hours. The reaction solution was concentrated under reduced pressure to obtain an oily crude product (400 mg), which was used directly in the next step.

MS m/z (ESI):114.1 $[M+H]^+$.

Step 5: Preparation of (S)-5-ethynylpyrrolidin-2-one

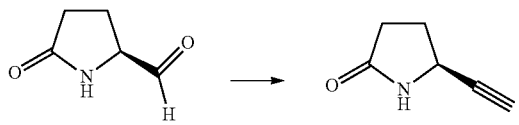

(S)-5-Oxopyrrolidine-2-carbaldehyde (400 mg, the crude product of the above step) was dissolved in MeOH (15 mL) in an ice bath, and then $K_2CO_3$ (931 mg, 6.74 mmol) and dimethyl (1-diazo-2-oxopropyl)phosphonate (1.01 g, 4.04 mmol) were added successively. The reaction solution was warmed up to room temperature slowly, and stirred at this temperature for 12 hours. The reaction solution was added with saturated brine (20 mL), and extracted with $CH_2Cl_2$ (100 mL×2). The organic phase was washed with saturated brine, dried over anhydrous sodium sulfate, and concentrated under reduced pressure. The residue was subjected to column chromatography to obtain the title compound (S)-5-ethynylpyrrolidin-2-one (260 mg, 71%).

$^1$H NMR (400 MHz, $CDCl_3$) δ 6.68 (s, 1H), 4.38-4.35 (m, 1H), 2.50-2.40 (m, 2H), 2.37 (d, J=2.2 Hz, 1H), 2.33-2.26 (m, 1H), 2.22-2.15 (m, 1H);

MS m/z (ESI):110.1 $[M+H]^+$.

Step 6: Preparation of (S)-2-ethynyl-5-methoxy-3,4-dihydro-2H-pyrrole

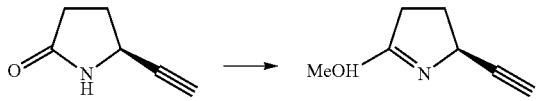

(S)-5-Ethynylpyrrolidin-2-one (0.26 g, 2.38 mmol) was dissolved in $CH_2Cl_2$ (10 mL) in an ice bath, and trimethyloxonium tetrafluoroborate (0.67 g, 4.53 mmol) was added in batches. The reaction solution was warmed up to room temperature slowly, and stirred at this temperature for 5 hours. The reaction solution was added with saturated aqueous $NaHCO_3$ solution (5 mL), and extracted with $CH_2Cl_2$ (50 mL×2). The organic phase was washed with saturated brine, dried over anhydrous sodium sulfate, added with glacial acetic acid (5 mL), and concentrated under reduced pressure to remove the organic solvent and obtain the crude product (315 mg), which was used directly in the next step.

MS m/z (ESI): 124.2 $[M+H]^+$.

Step 7: Preparation of (S)-6-(5-ethynyl-6,7-dihydro-5H-pyrrolo[2,1-c][1,2,4]triazol-3-yl)pyridin-2-amine

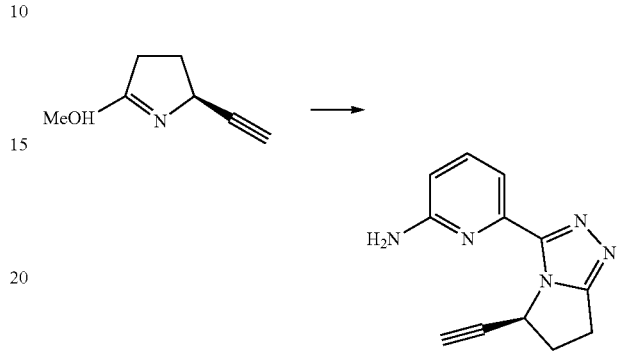

6-Aminopicolinohydrazide (320 mg, 2.1 mmol) was dissolved in 2-pentanol (15 mL) and acetic acid (1 mL) at room temperature, and then (S)-2-ethynyl-5-methoxy-3,4-dihydro-2H-pyrrole (315 mg, the crude product of the above step) was added. The reaction solution was heated to 125° C., and stirred at this temperature for 12 hours. After cooling to room temperature, the reaction solution was concentrated under reduced pressure. The residue was added with saturated aqueous $NaHCO_3$ solution (5 mL), and extracted with dichloromethane (50 mL×2). The organic phase was washed with saturated brine, dried over anhydrous sodium sulfate, and concentrated to remove the organic solvent. The residue was subjected to column chromatography to obtain the title compound (S)-6-(5-ethynyl-6,7-dihydro-5H-pyrrolo[2,1-c][1,2,4]triazol-3-yl)pyridin-2-amine (362 mg, yield of two steps: 46%).

MS m/z (ESI): 226.2 $[M+H]^{-1}$.

Step 8: Preparation of (S)-5-(4-cyclopropyl-1H-imidazol-1-yl)-N-(6-(5-ethynyl-6,7-dihydro-5H-pyrrolo[2,1-c][1,2,4]triazol-3-yl)pyridin-2-yl)-2-fluoro-4-methylbenzamide

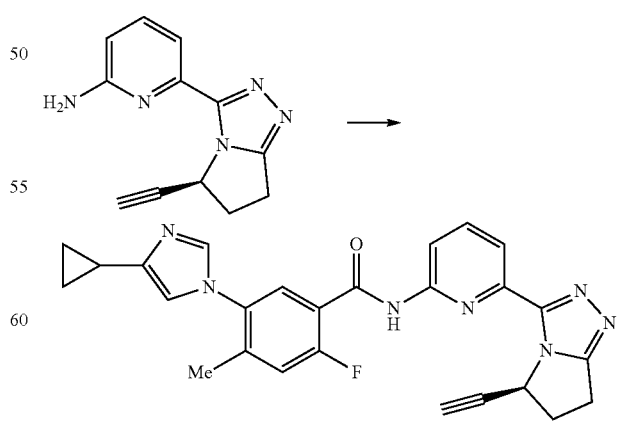

(S)-6-(5-Ethynyl-6,7-dihydro-5H-pyrrolo[2,1-c][1,2,4]triazol-3-yl)pyridin-2-amine (80 mg, 0.36 mmol) was added to a solution of 5-(4-cyclopropyl-1H-imidazol-1-yl)-2- fluoro-4-methylbenzoyl chloride (220 mg, 0.79 mmol) in THF (25 mL) and pyridine (35 mL) at room temperature, and then 4-dimethylaminopyridine (15 mg, 0.12 mmol) was added. The reaction solution was heated to 45° C., and stirred at this temperature for 2 hours. The reaction solution was added with water (5 mL) to quench the reaction, and extracted with dichloromethane (50 mL×2). The organic phase was washed with saturated brine, dried over anhydrous sodium sulfate, and concentrated to remove the organic solvent. The residue was subjected to column chromatography to obtain the title compound (S)-5-(4-cyclopropyl-1H-imidazol-1-yl)-N-(6-(5-ethynyl-6,7-dihydro-5H-pyrrolo[2,1-c][1,2,4]triazol-3-yl)pyridin-2-yl)-2-fluoro-4-methylbenzamide (122 mg, yield: 73%).

$^1$H NMR (400 MHz, CDCl$_3$) δ 9.09 (d, J=15.0 Hz, 1H), 8.42-8.28 (m, 1H), 8.08-7.94 (m, 2H), 7.81 (t, J=7.0 Hz, 1H), 7.49 (s, 1H), 7.14 (d, J=12.6 Hz, 1H), 6.74 (s, 1H), 5.49-5.47 (m, 1H), 3.16-3.10 (m, 2H), 3.0-2.95 (m, 1H), 2.93-2.80 (m, 1H), 2.34 (d, J=2.4 Hz, 1H), 2.22 (s, 3H), 1.91-1.77 (m, 1H), 0.87-0.83 (m, 2H), 0.79-0.77 (m, 2H);

MS m/z (ESI): 468.2 [M+H]$^{-1}$.

Example 44

5-(4-Cyclopropyl-1H-imidazol-1-yl)-N-(6-(5-ethynyl-6,7-dihydro-5H-pyrrolo[2,1-c][1,2,4]triazol-3-yl)pyridin-2-yl)-2-fluoro-4-methylbenzamide

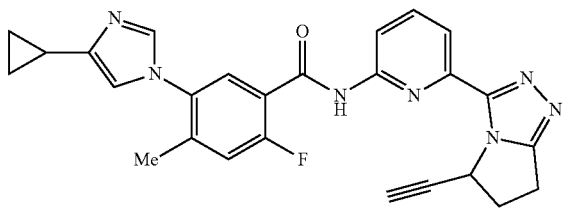 [SMILES: C#C[C@H]1CCc2nnc(-c3cccc(NC(=O)c4cc(-n5cnc(C6CC6)c5)c(C)cc4F)n3)n21]

5-(4-Cyclopropyl-1H-imidazol-1-yl)-N-(6-(5-ethynyl-6,7-dihydro-5H-pyrrolo[2,1-c][1,2,4]triazol-3-yl)pyridin-2-yl)-2-fluoro-4-methylbenzamide was prepared in accordance with Example 43.

$^1$H NMR (400 MHz, CDCl$_3$) δ 9.09 (d, J=15.0 Hz, 1H), 8.42-8.28 (m, 1H), 8.08-7.94 (m, 2H), 7.81 (t, J=7.0 Hz, 1H), 7.49 (s, 1H), 7.14 (d, J=12.6 Hz, 1H), 6.74 (s, 1H), 5.49-5.47 (m, 1H), 3.16-3.10 (m, 2H), 3.0-2.95 (m, 1H), 2.93-2.80 (m, 1H), 2.34 (d, J=2.4 Hz, 1H), 2.22 (s, 3H), 1.91-1.77 (m, 1H), 0.87-0.83 (m, 2H), 0.79-0.77 (m, 2H);

MS m/z (ESI): 468.2 [M+H]$^+$.

Example 45

(R)-5-(4-Cyclopropyl-1H-imidazol-1-yl)-N-(6-(5-ethynyl-6,7-dihydro-5H-pyrrolo[2,1-c][1,2,4]triazol-3-yl)pyridin-2-yl)-2-fluoro-4-methylbenzamide

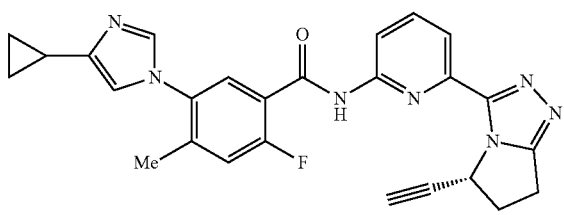

(R)-5-(4-Cyclopropyl-1H-imidazol-1-yl)-N-(6-(5-ethynyl-6,7-dihydro-5H-pyrrolo[2,1-c][1,2,4]triazol-3-yl)pyridin-2-yl)-2-fluoro-4-methylbenzamide was prepared in accordance with Example 43.

$^1$H NMR (400 MHz, CDCl$_3$) δ 9.09 (d, J=15.0 Hz, 1H), 8.42-8.28 (m, 1H), 8.08-7.94 (m, 2H), 7.81 (t, J=7.0 Hz, 1H), 7.49 (s, 1H), 7.14 (d, J=12.6 Hz, 1H), 6.74 (s, 1H), 5.49-5.47 (m, 1H), 3.16-3.10 (m, 2H), 3.0-2.95 (m, 1H), 2.93-2.80 (m, 1H), 2.34 (d, J=2.4 Hz, 1H), 2.22 (s, 3H), 1.91-1.77 (m, 1H), 0.87-0.83 (m, 2H), 0.79-0.77 (m, 2H);

MS m/z (ESI): 468.2 [M+H]$^+$.

Example 46

(S)—N-(6-(5-Cyano-6,7-dihydro-5H-pyrrolo[2,1-c][1,2,4]triazol-3-yl)pyridin-2-yl)-5-(4-cyclopropyl-1H-imidazol-1-yl)-2-fluoro-4-methylbenzamide

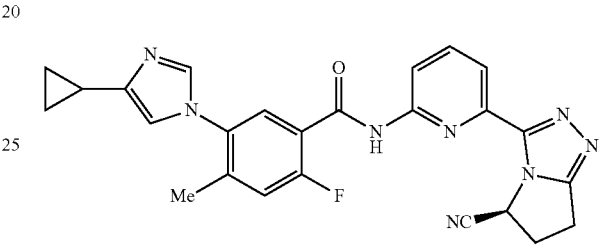

(S)—N-(6-(5-Cyano-6,7-dihydro-5H-pyrrolo[2,1-c][1,2,4]triazol-3-yl)pyridin-2-yl)-5-(4-cyclopropyl-1H-imidazol-1-yl)-2-fluoro-4-methylbenzamide was prepared in accordance with the method of Example 8.

$^1$H NMR (400 MHz, CD$_3$OD) δ 9.06 (s, 1H), 8.30 (d, J=8.2 Hz, 1H), 7.99 (t, J=7.9 Hz, 1H), 7.95-7.89 (m, 2H), 7.52 (s, 1H), 7.39 (d, J=10.8 Hz, 1H), 6.17-6.06 (m, 1H), 3.43-3.34 (m, 2H), 3.17-3.08 (m, 2H), 2.25 (s, 3H), 2.00-1.95 (m, 1H), 1.08-1.02 (m, 2H), 0.85-0.79 (m, 2H);

MS m/z (ESI): 469.1 [M+H]$^+$.

Example 47

(R)—N-(6-(5-Cyano-6,7-dihydro-5H-pyrrolo[2,1-c][1,2,4]triazol-3-yl)pyridin-2-yl)-5-(4-cyclopropyl-1H-imidazol-1-yl)-2-fluoro-4-methylbenzamide

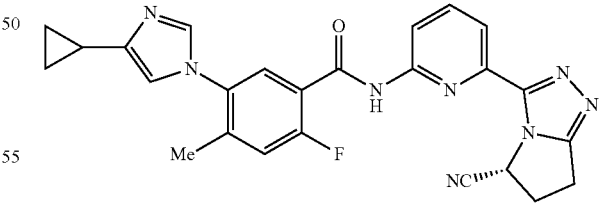

(R)—N-(6-(5-Cyano-6,7-dihydro-5H-pyrrolo[2,1-c][1,2,4]triazol-3-yl)pyridin-2-yl)-5-(4-cyclopropyl-1H-imidazol-1-yl)-2-fluoro-4-methylbenzamide was prepared in accordance with the method of Example 8.

$^1$H NMR (400 MHz, CD$_3$OD) δ 9.06 (s, 1H), 8.30 (d, J=8.2 Hz, 1H), 7.99 (t, J=7.9 Hz, 1H), 7.95-7.89 (m, 2H), 7.52 (s, 1H), 7.39 (d, J=10.8 Hz, 1H), 6.17-6.06 (m, 1H), 3.43-3.34 (m, 2H), 3.17-3.08 (m, 2H), 2.25 (s, 3H), 2.00-1.95 (m, 1H), 1.08-1.02 (m, 2H), 0.85-0.79 (m, 2H);

MS m/z (ESI): 469.1 [M+H]$^+$.

Example 48

(S)—N-(6-(5-(Cyanomethyl)-6,7-dihydro-5H-pyrrolo[2,1-c][1,2,4]triazol-3-yl)pyridin-2-yl)-5-(4-cyclopropyl-1H-imidazol-1-yl)-2-fluoro-4-methylbenzamide

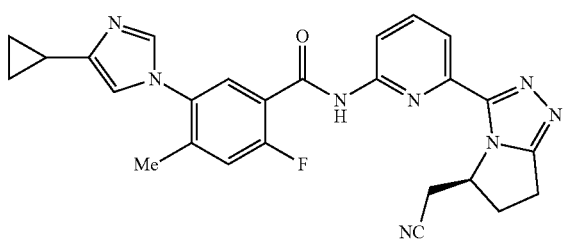 [SMILES: Cc1cc(F)c(C(=O)Nc2cccc(-c3nnc4n3[C@H](CC#N)CC4)n2)cc1-n1cnc(C2CC2)c1]

(S)—N-(6-(5-(Cyanomethyl)-6,7-dihydro-5H-pyrrolo[2,1-c][1,2,4]triazol-3-yl)pyrid in-2-yl)-5-(4-cyclopropyl-1H-imidazol-1-yl)-2-fluoro-4-methylbenzamide was prepared in accordance with the method of Example 8.

$^1$H NMR (400 MHz, CD$_3$OD) δ 9.19 (s, 1H), 8.39 (d, J=8.1 Hz, 1H), 8.15 (t, J=7.8 Hz, 1H), 8.11-8.07 (m, 1H), 8.06-7.99 (m, 1H), 7.64 (s, 1H), 7.50 (d, J=10.6 Hz, 1H), 5.80 (s, 1H), 3.65-3.53 (m, 1H), 3.49-3.38 (m, 4H), 3.03-2.92 (m, 1H), 2.36 (s, 3H), 2.15-2.07 (m, 1H), 1.22-1.11 (m, 2H), 0.98-0.91 (m, 2H);

MS m/z (ESI): 483.2 [M+H]$^+$.

Example 49

(S)—N-(6-(5-(Cyanomethyl)-6,7-dihydro-5H-pyrrolo[2,1-c][1,2,4]triazol-3-yl)pyridin-2-yl)-5-(4-cyclopropyl-1H-imidazol-1-yl)-2-fluoro-4-methylbenzamide

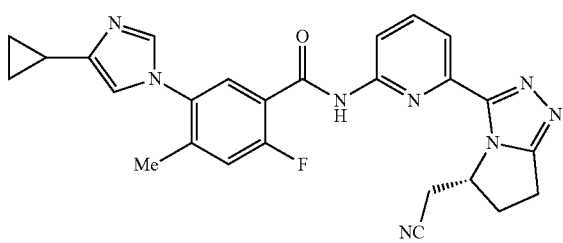 [SMILES: Cc1cc(F)c(C(=O)Nc2cccc(-c3nnc4n3[C@@H](CC#N)CC4)n2)cc1-n1cnc(C2CC2)c1]

(R)—N-(6-(5-(Cyanomethyl)-6,7-dihydro-5H-pyrrolo[2,1-c][1,2,4]triazol-3-yl)pyrid in-2-yl)-5-(4-cyclopropyl-1H-imidazol-1-yl)-2-fluoro-4-methylbenzamide was prepared in accordance with the method of Example 8.

$^1$H NMR (400 MHz, CD$_3$OD) δ 9.19 (s, 1H), 8.39 (d, J=8.1 Hz, 1H), 8.15 (t, J=7.8 Hz, 1H), 8.11-8.07 (m, 1H), 8.06-7.99 (m, 1H), 7.64 (s, 1H), 7.50 (d, J=10.6 Hz, 1H), 5.80 (s, 1H), 3.65-3.53 (m, 1H), 3.49-3.38 (m, 4H), 3.03-2.92 (m, 1H), 2.36 (s, 3H), 2.15-2.07 (m, 1H), 1.22-1.11 (m, 2H), 0.98-0.91 (m, 2H);

MS m/z (ESI): 483.2 [M+H]$^+$.

Example 50

(S)-5-(4-Cyclopropyl-1H-imidazol-1-yl)-2-fluoro-N-(6-(5-(hydroxymethyl)-6,7-dihydro-5H-pyrrolo[2,1-c][1,2,4]triazol-3-yl)pyridin-2-yl)-4-methylbenzamide

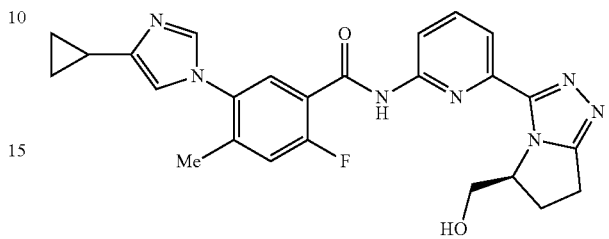

(S)-5-(4-Cyclopropyl-1H-imidazol-1-yl)-2-fluoro-N-(6-(5-(hydroxymethyl)-6,7-di hydro-5H-pyrrolo[2,1-c][1,2,4]triazol-3-yl)pyridin-2-yl)-4-methylbenzamide was prepared in accordance with Example 8.

$^1$H NMR (400 MHz, CDCl$_3$) δ 9.06 (d, J=15.6 Hz, 1H), 8.28-8.16 (m, 1H), 8.04 (d, J=7.2 Hz, 1H), 7.79-7.65 (m, 2H), 7.42 (t, J=4.0 Hz, 1H), 7.19 (d, J=12.2 Hz, 1H), 6.79 (s, 1H), 4.97-4.83 (m, 1H), 4.47 (m, 1H), 4.05-3.87 (m, 1H), 3.30-3.15 (m, 1H), 3.00-2.75 (m, 3H), 2.29 (s, 3H), 1.94-1.75 (m, 2H), 0.94-0.86 (m, 2H), 0.86-0.70 (m, 2H);

MS m/z (ESI): 474.1 [M+H]$^+$.

Example 51

(S)-5-(4-Cyclopropyl-1H-imidazol-1-yl)-2-fluoro-N-(6-(5-(fluoromethyl)-6,7-dihydro-5H-pyrrolo[2,1-c][1,2,4]triazol-3-yl)pyridin-2-yl)-4-methylbenzamide

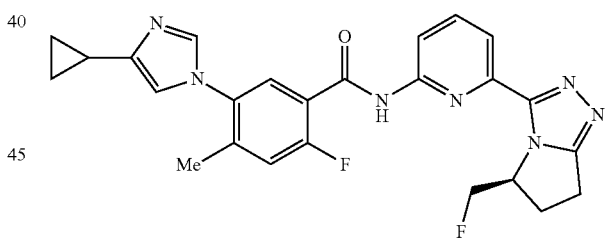

Step 1: Preparation of (S)-2-(fluoromethyl)-5-methoxy-3,4-dihydro-2H-pyrrole

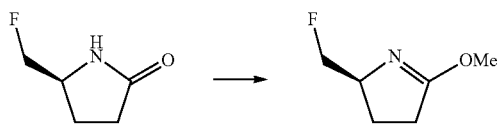 [SMILES: O=C1CC[C@@H](CF)N1 ; COC1=N[C@H](CF)CC1]

(S)-5-(Fluoromethyl)pyrrolidin-2-one (0.7 g, 6.0 mmol) was dissolved in dichloromethane (60 mL) in an ice bath, and then trimethyloxonium tetrafluoroborate (1.24 g, 8.4 mmol) was added in batches. The reaction solution was warmed up to room temperature slowly, and stirred at this temperature for 5 hours. The reaction solution was added with saturated aqueous NaHCO₃ solution (5 mL), and extracted with dichloromethane (50 mL×2). The organic phase was washed with saturated brine, dried over anhydrous sodium sulfate, added with glacial acetic acid (5 mL), and concentrated under reduced pressure to remove the organic solvent and obtain the crude product, which was used directly in the next step.

MS m/z (ESI): 132.2 [M+H]⁻¹.

Step 2: Preparation of (S)-6-(5-(fluoromethyl)-6,7-dihydro-5H-pyrrolo[2,1-c][1,2,4]triazol-3-yl)pyridin-2-amine

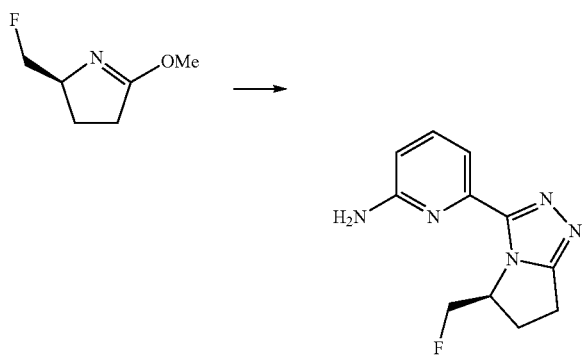

6-Aminopicolinohydrazide (900 mg, 6.0 mmol) was dissolved in 2-pentanol (15 mL) and acetic acid (1 mL) at room temperature, and then (S)-2-(fluoromethyl)-5-methoxy-3,4-dihydro-2H-pyrrole (783 mg, 6.0 mmol) was added. The reaction solution was heated to 125° C., and stirred at this temperature for 12 hours. After cooling to room temperature, the reaction solution was concentrated under reduced pressure. The residue was added with saturated aqueous NaHCO₃ solution (5 mL), and extracted with dichloromethane (50 mL×2). The organic phase was washed with saturated brine, dried over anhydrous sodium sulfate, and concentrated to remove the organic solvent. The residue was subjected to column chromatography to obtain the title compound (S)-6-(5-(fluoromethyl)-6,7-dihydro-5H-pyrrolo[2,1-c][1,2,4]triazol-3-yl)pyridin-2-amine (430 mg, yield of two steps: 55%).

¹H NMR (400 MHz, CDCl₃) δ 7.69 (m, 1H), 7.66-7.51 (m, 1H), 6.60-6.47 (m, 1H), 5.21-5.04 (m, 1H), 4.94 (m, 0.5H), 4.82 (m, 1H), 4.70 (m, 0.5H), 3.20-2.92 (m, 3H), 2.85-2.70 (m, 1H);

MS m/z (ESI): 234.2 [M+H]⁻¹.

Step 3: Preparation of (S)-5-(4-cyclopropyl-1H-imidazol-1-yl)-2-fluoro-N-(6-(5-(fluoromethyl)-6,7-dihydro-5H-pyrrolo[2,1-c][1,2,4]triazol-3-yl)pyridin-2-yl)-4-methylbenzamide

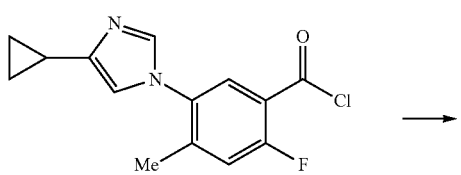

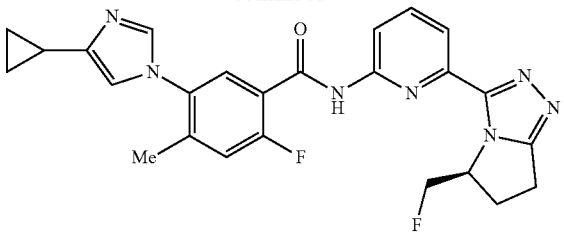

(S)-6-(5-(fluoromethyl)-6,7-dihydro-5H-pyrrolo[2,1-c][1,2,4]triazol-3-yl)pyridin-2-amine (195 mg, 0.84 mmol) was added to a solution of 5-(4-cyclopropyl-1H-imidazol-1-yl)-2-fluoro-4-methylbenzoyl chloride (390 mg, 1.4 mmol) in THF (15 mL) and pyridine (15 mL) at room temperature, and then 4-dimethylaminopyridine (26 mg, 0.21 mmol) was added. The reaction solution was heated to 45° C., and stirred at this temperature for 2 hours. The reaction solution was added with water (5 mL) to quench the reaction, and extracted with dichloromethane (50 mL×2). The organic phase was washed with saturated brine, dried over anhydrous sodium sulfate, and concentrated under reduced pressure to remove the organic solvent. The residue was subjected to column chromatography to obtain the title compound (S)-5-(4-cyclopropyl-1H-imidazol-1-yl)-2-fluoro-N-(6-(5-(fluoromethyl)-6,7-dihydro-5H-pyrrolo[2,1-c][1,2,4]triazol-3-yl)pyridin-2-yl)-4-methylbenzamide (179 mg, yield 45%).

¹H NMR (400 MHz, CDCl₃) δ 9.06 (d, J=15.6 Hz, 1H), 8.30-8.28 (m, 1H), 8.16-7.96 (m, 2H), 7.87 (t, J=8.0 Hz, 1H), 7.45-7.43 (m, 1H), 7.16 (d, J=12.6 Hz, 1H), 6.77 (s, 1H), 5.17-5.00 (m, 1H), 4.96-4.93 (m, 0.5H), 4.84-4.79 (m, 1H), 4.71-4.68 (m, 0.5H), 3.19-2.87 (m, 3H), 2.87-2.68 (m, 1H), 2.26 (s, 3H), 1.93-1.81 (m, 1H), 0.92-0.74 (m, 4H);

MS m/z (ESI): 476.2 [M+H]⁺.

Example 52

(R)-5-(4-Cyclopropyl-1H-imidazol-1-yl)-2-fluoro-N-(6-(5-(fluoromethyl)-6,7-dihydro-5H-pyrrolo[2,1-c][1,2,4]triazol-3-yl)pyridin-2-yl)-4-methylbenzamide

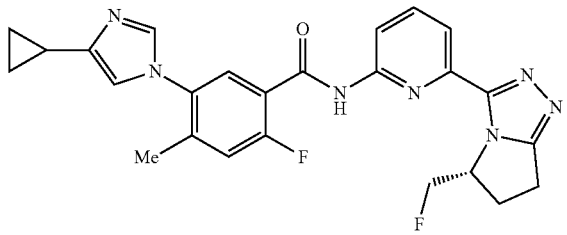 [SMILES: Cc1cc(F)c(C(=O)Nc2cccc(-c3nnc4n3[C@@H](CF)CC4)n2)cc1-n1cnc(C2CC2)c1]

(R)-5-(4-Cyclopropyl-1H-imidazol-1-yl)-2-fluoro-N-(6-(5-(fluoromethyl)-6,7-dihydro-5H-pyrrolo[2,1-c][1,2,4]triazol-3-yl)pyridin-2-yl)-4-methylbenzamide was prepared in accordance with Example 51.

¹H NMR (400 MHz, CDCl₃) δ 9.06 (d, J=15.6 Hz, 1H), 8.30-8.28 (m, 1H), 8.16-7.96 (m, 2H), 7.87 (t, J=8.0 Hz, 1H), 7.45-7.43 (m, 1H), 7.16 (d, J=12.6 Hz, 1H), 6.77 (s, 1H), 5.17-5.00 (m, 1H), 4.96-4.93 (m, 0.5H), 4.84-4.79 (m, 1H), 4.71-4.68 (m, 0.5H), 3.19-2.87 (m, 3H), 2.87-2.68 (m, 1H), 2.26 (s, 3H), 1.93-1.81 (m, 1H), 0.92-0.74 (m, 4H);

MS m/z (ESI): 476.2 [M+H]⁺.

Example 53

(R)-2-Chloro-5-(4-cyclopropyl-1H-imidazol-1-yl)-4-methyl-N-(6-(5-methyl-6,7-dihydro-5H-pyrrolo[2,1-c][1,2,4]triazol-3-yl)pyridin-2-yl)benzamide

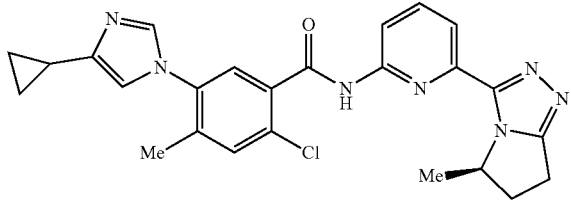 [SMILES: Cc1cc(Cl)c(C(=O)Nc2cccc(-c3nnc4n3[C@H](C)CC4)n2)cc1-n1cnc(C2CC2)c1]

(R)-2-Chloro-5-(4-cyclopropyl-1H-imidazol-1-yl)-4-methy 1-N-(6-(5-methyl-6,7-di hydro-5H-pyrrolo[2,1-c][1,2,4]triazol-3-yl)pyridin-2-yl)benzamide was prepared in accordance with Example 8.

$^1$H NMR (400 MHz, CD$_3$OD) δ 8.19 (d, J=8.1 Hz, 1H), 7.89 (t, J=7.9 Hz, 1H), 7.84-7.79 (m, 1H), 7.68 (s, 1H), 7.56-7.49 (m, 2H), 7.12 (s, 1H), 6.27-6.22 (m, 2H), 5.19-5.09 (m, 1H), 3.08-2.80 (m, 3H), 2.39-2.31 (m, 1H), 2.18 (s, 3H), 1.78-1.73 (m, 3H), 1.36-1.31 (m, 3H);

MS m/z (ESI): 474.1 [M+H]$^+$.

Example 54

(S)-2-Chloro-5-(4-cyclopropyl-1H-imidazol-1-yl)-4-methyl-N-(6-(5-methyl-6,7-dihydro-5H-pyrrolo[2,1-c][1,2,4]triazol-3-yl)pyridin-2-yl)benzamide

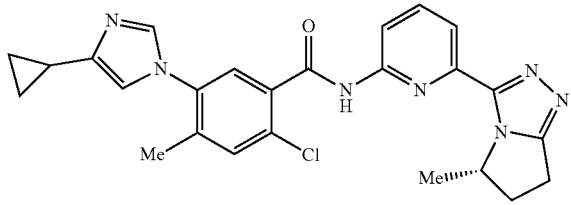 [SMILES: Cc1cc(Cl)c(C(=O)Nc2cccc(-c3nnc4n3[C@@H](C)CC4)n2)cc1-n1cnc(C2CC2)c1]

(S)-2-Chloro-5-(4-cyclopropyl-1H-imidazol-1-yl)-4-methyl-N-(6-(5-methyl-6,7-di hydro-5H-pyrrolo[2,1-c][1,2,4]triazol-3-yl)pyridin-2-yl)benzamide was prepared in accordance with the method of Example 8.

$^1$H NMR (400 MHz, CD$_3$OD) δ 8.19 (d, J=8.1 Hz, 1H), 7.89 (t, J=7.9 Hz, 1H), 7.84-7.79 (m, 1H), 7.68 (s, 1H), 7.56-7.49 (m, 2H), 7.12 (s, 1H), 6.27-6.22 (m, 2H), 5.19-5.09 (m, 1H), 3.08-2.80 (m, 3H), 2.39-2.31 (m, 1H), 2.18 (s, 3H), 1.78-1.73 (m, 3H), 1.36-1.31 (m, 3H);

MS m/z (ESI): 474.1 [M+H]$^+$.

Example 55

(R)-5-(4-Cyclopropyl-1H-imidazol-1-yl)-N-(6-(5-ethyl-6,7-dihydro-5H-pyrrolo[2,1-c][1,2,4]triazol-3-yl)pyridin-2-yl)-2-fluoro-4-methylbenzamide

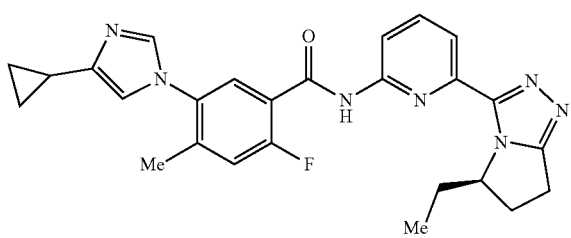 [SMILES: CC[C@@H]1CCc2nnc(-c3cccc(NC(=O)c4cc(-n5cnc(C6CC6)c5)c(C)cc4F)n3)n21]

Step 1: Preparation of (S)-(5-oxopyrrolidin-2-yl) methyl 4-methylbenzenesulfonate

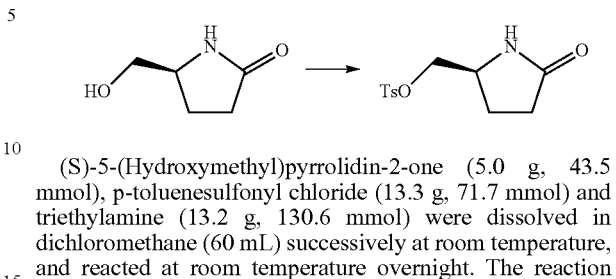

(S)-5-(Hydroxymethyl)pyrrolidin-2-one (5.0 g, 43.5 mmol), p-toluenesulfonyl chloride (13.3 g, 71.7 mmol) and triethylamine (13.2 g, 130.6 mmol) were dissolved in dichloromethane (60 mL) successively at room temperature, and reacted at room temperature overnight. The reaction solution was diluted by adding dichloromethane (80 mL), and washed with 1N HCl. The organic phase was dried over anhydrous sodium sulfate, filtrated, and concentrated under reduced pressure to remove the organic solvent. The crude product was purified by column chromatography to obtain (S)-(5-oxopyrrolidin-2-yl) methyl 4-methylbenzenesulfonate (8.3 g, yield: 71%).

$^1$H NMR (400 MHz, CDCl$_3$) δ 7.79 (d, J=8.3 Hz, 2H), 7.37 (d, J=8.2 Hz, 2H), 6.26 (s, 1H), 4.06-4.03 (m, 1H), 3.97-3.84 (m, 2H), 2.46 (s, 3H), 2.36-2.19 (m, 3H), 1.83-1.72 (m, 1H);

MS m/z (ESI): 270.1 [M+H]$^+$.

Step 2: Preparation of (R)-5-ethylpyrrolidin-2-one

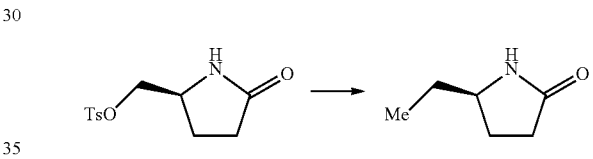

Cuprous iodide (1.06 g, 5.6 mmol) was dissolved in tetrahydrofuran (6 mL) in an ice bath, and the reaction system was purged with nitrogen three times. The reaction solution was added dropwise with methyl lithium (7.4 mL, 11.1 mmol), and stirred at 0° C. for 45 min. The reaction solution was cooled to −20° C., and added dropwise with a solution of (S)-(5-oxopyrrolidin-2-yl) methyl 4-methylbenzenesulfonate (500 mg, 1.9 mmol) in tetrahydrofuran (6 mL). The reaction solution was stirred at −20° C. for 45 min, and then gradually warmed up to room temperature to react overnight. The reaction solution was added with saturated ammonium chloride, and extracted with ethyl acetate. The organic phase was dried over anhydrous sodium sulfate, filtrated, and concentrated under reduced pressure to remove the organic solvent. The crude product was purified by column chromatography to obtain (R)-5-ethylpyrrolidin-2-one (185 mg, yield: 86%).

$^1$H NMR (400 MHz, CD$_3$OD) δ 3.54-3.45 (m, 1H), 2.24-2.19 (m, 2H), 2.18-2.09 (m, 1H), 1.66-1.57 (m, 1H), 1.53-1.43 (m, 1H), 1.42-1.32 (m, 1H), 0.84 (t, J=7.5 Hz, 3H);

MS m/z (ESI): 114.2 [M+H]$^+$.

Step 3: Preparation of (R)-2-ethyl-5-methoxy-3,4-dihydro-2H-pyrrole

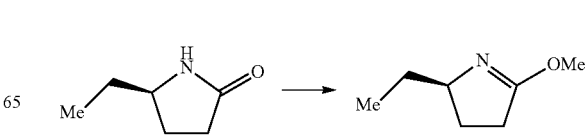

Trimethyloxonium tetrafluoroborate (226 mg, 1.59 mmol) was added to a solution of (R)-5-ethylpyrrolidin-2-one (180 mg, 1.59 mmol) in dichloromethane (10 mL) in batches in an ice bath. The reaction solution was warmed up to room temperature slowly, and stirred at this temperature for 5 hours. The reaction solution was added with saturated aqueous NaHCO₃ solution (5 mL), and extracted with dichloromethane (50 mL×2). The organic phase was washed with saturated brine, dried over anhydrous sodium sulfate, added with glacial acetic acid (5 mL), and concentrated under reduced pressure to obtain the crude product, which was used directly in the next step.

MS m/z (ESI): 128.2 [M+H]⁺.

Step 4: Preparation of 6-aminopicolinohydrazide

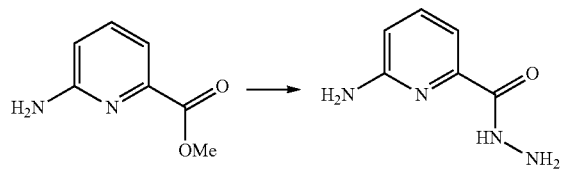 [SMILES: COC(=O)c1cccc(N)n1 ; NNC(=O)c1cccc(N)n1]

Methyl 6-aminopicolinate (2.0 g, 13 mmol) was dissolved in ethanol (60 mL) at room temperature, and then hydrazine hydrate (4.1 g, 66 mmol) was added. The reaction solution was heated to 80° C., and stirred at this temperature for 5 hours. After the reaction solution was cooled slowly to room temperature, the precipitated solid was filtrated. The filter cake was collected to obtain the title compound 6-aminopicolinohydrazide (1.6 g, 80%).

MS m/z (ESI): 153.2 [M+H]⁺.

Step 5: Preparation of (R)-6-(5-ethyl-6,7-dihydro-5H-pyrrolo[2,1-c][1,2,4]triazol-3-yl)pyridin-2-amine

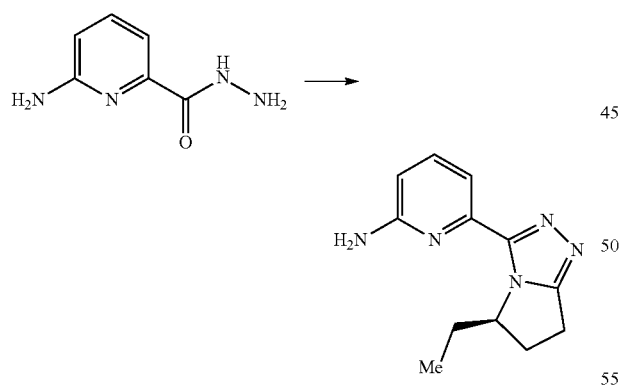

6-Aminopicolinohydrazide (243 mg, 1.59 mmol) was dissolved in 2-pentanol (5 mL) and acetic acid (2 mL) at room temperature, and then (R)-2-ethyl-5-methoxy-3,4-dihydro-2H-pyrrole (202 mg, 1.59 mmol) was added. The reaction solution was heated to 125° C., and stirred at this temperature for 12 hours. After cooling to room temperature, the reaction solution was concentrated under reduced pressure. The residue was added with saturated aqueous NaHCO₃ solution (5 mL), and extracted with dichloromethane (50 mL×2). The organic phase was washed with saturated brine, dried over anhydrous sodium sulfate, and concentrated. The residue was subjected to column chromatography to obtain the title compound (R)-6-(5-ethyl-6,7-dihydro-5H-pyrrolo[2,1-c][1,2,4]triazol-3-yl)pyridin-2-amine (70 mg, yield of two steps: 19%).

MS m/z (ESI): 230.2 [M+H]⁺.

Step 6: Preparation of 5-(4-cyclopropyl-1H-imidazol-1-yl)-2-fluoro-4-methylbenzoyl Chloride

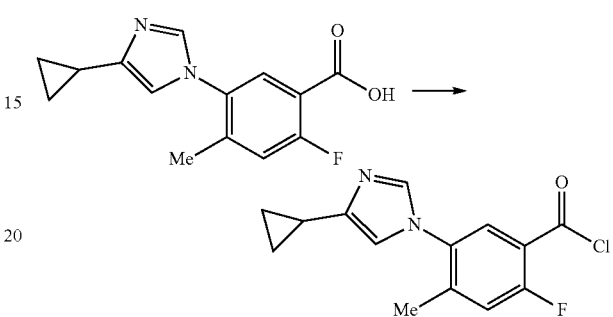

The above 5-(4-cyclopropyl-1H-imidazol-1-yl)-2-fluoro-4-methylbenzoic acid hydrochloride (154 mg, 0.594 mmol) was dissolved in thionyl chloride (5 mL) at room temperature, and stirred for 2 hours under heating reflux. After cooling, the reaction solution was concentrated under reduced pressure to obtain a pale yellow solid product, which was used directly in the next step.

Step 7: Preparation of (R)-5-(4-cyclopropyl-1H-imidazol-1-yl)-N-(6-(5-ethyl-6,7-dihydro-5H-pyrrolo[2,1-c][1,2,4]triazol-3-yl)pyridin-2-yl)-2-fluoro-4-methylbenzamide

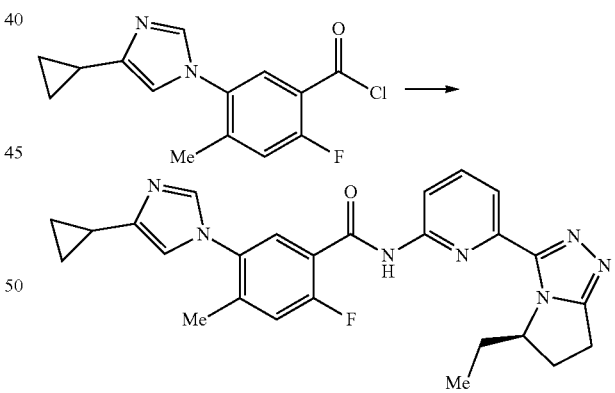

(R)-6-(5-ethyl-6,7-dihydro-5H-pyrrolo[2,1-c][1,2,4]triazol-3-yl)pyridin-2-amine (68 mg, 0.297 mmol) was added to a solution of 5-(4-cyclopropyl-1H-imidazol-1-yl)-2-fluoro-4-methylbenzoyl chloride (165 mg, 0.594 mmol) in THF (6 mL) and pyridine (4 mL) at room temperature, and then 4-dimethylaminopyridine (15 mg, 0.119 mmol) was added. The reaction solution was heated to 45° C., and stirred at this temperature for 2 hours. The reaction solution was added with water (5 mL), and extracted with dichloromethane (50 mL×2). The organic phase was washed with saturated brine, dried over anhydrous sodium sulfate, and concentrated. The residue was subjected to column chromatography to obtain the title compound (R)-5-(4-cyclopropyl-1H-imidazol-1-yl)-N-(6-(5-ethyl-6,7-dihydro-5H-pyrrolo[2,1-c][1,2,4]triazol-3-yl)pyridin-2-yl)-2-fluoro-4-methylbenzamide (26 mg, yield: 19%).

¹H NMR (400 MHz, CDCl₃) δ 9.04 (d, J=15.8 Hz, 1H), 8.40-8.33 (m, 1H), 8.14-8.07 (m, 2H), 7.89 (t, J=8.0 Hz, 1H), 7.52 (s, 1H), 7.21 (d, J=12.6 Hz, 1H), 6.82-6.79 (m, 1H), 4.87-4.81 (m, 1H), 3.08-2.89 (m, 3H), 2.61-2.50 (m, 1H), 2.30 (s, 3H), 2.15-2.05 (m, 1H), 1.96-1.90 (m, 1H), 1.79-1.71 (m, 1H), 1.00 (t, J=7.5 Hz, 3H), 0.95-0.89 (m, 2H), 0.88-0.79 (m, 2H);

MS m/z (ESI): 472.2 [M+H]⁺.

Example 56

(S)-5-(4-Cyclopropyl-1H-imidazol-1-yl)-N-(6-(5-ethyl-6,7-dihydro-5H-pyrrolo[2,1-c][1,2,4]triazol-3-yl)pyridin-2-yl)-2-fluoro-4-methylbenzamide

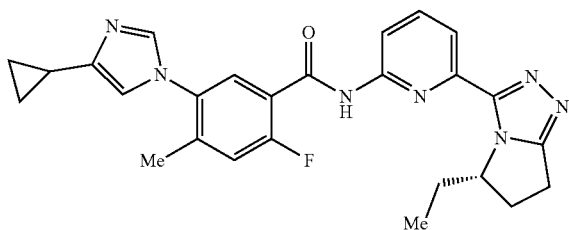 [SMILES: CC[C@H]1CCc2nnc(-c3cccc(NC(=O)c4cc(-n5cnc(C6CC6)c5)c(C)cc4F)n3)n21]

(S)-5-(4-Cyclopropyl-1H-imidazol-1-yl)-N-(6-(5-ethyl-6,7-dihydro-5H-pyrrolo[2,1-c][1,2,4]triazol-3-yl)pyridin-2-yl)-2-fluoro-4-methylbenzamide was prepared in accordance with the method of Example 55.

¹H NMR (400 MHz, CDCl₃) δ 9.04 (d, J=15.8 Hz, 1H), 8.40-8.33 (m, 1H), 8.14-8.07 (m, 2H), 7.89 (t, J=8.0 Hz, 1H), 7.52 (s, 1H), 7.21 (d, J=12.6 Hz, 1H), 6.82-6.79 (m, 1H), 4.87-4.81 (m, 1H), 3.08-2.89 (m, 3H), 2.61-2.50 (m, 1H), 2.30 (s, 3H), 2.15-2.05 (m, 1H), 1.96-1.90 (m, 1H), 1.79-1.71 (m, 1H), 1.00 (t, J=7.5 Hz, 3H), 0.95-0.89 (m, 2H), 0.88-0.79 (m, 2H);

MS m/z (ESI): 472.2 [M+H]⁺.

Example 57

(S)-5-(4-Cyclopropyl-1H-imidazol-1-yl)-2-fluoro-N-(6-(5-isopropyl-6,7-dihydro-5H-pyrrolo[2,1-c][1,2,4]triazol-3-yl)pyridin-2-yl)-4-methylbenzamide

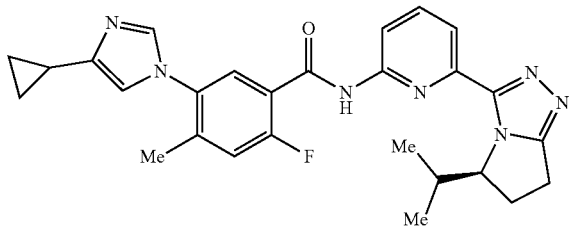 [SMILES: Cc1cc(F)c(C(=O)Nc2cccc(-c3nnc4n3[C@H](C(C)C)CC4)n2)cc1-n1cnc(C2CC2)c1]

(S)-5-(4-Cyclopropyl-1H-imidazol-1-yl)-2-fluoro-N-(6-(5-isopropyl-6,7-dihydro-5H-pyrrolo[2,1-c][1,2,4]triazol-3-yl)pyridin-2-yl)-4-methylbenzamide was prepared in accordance with Example 8.

¹H NMR (400 MHz, CDCl₃) δ 9.00 (d, J=15.6 Hz, 1H), 8.46-8.26 (m, 1H), 8.10-7.99 (m, 2H), 7.80 (m, 1H), 7.43 (t, J=8.8 Hz, 1H), 7.14 (d, J=12.6 Hz, 1H), 6.73 (s, 1H), 4.86-4.61 (m, 1H), 3.00-2.81 (m, 2H), 2.76 (m, 1H), 2.60-2.47 (m, 2H), 2.22 (s, 3H), 1.85 (m, 1H), 1.01 (d, J=7.0 Hz, 3H), 0.84 (m, 2H), 0.80-0.74 (m, 2H), 0.60 (m, 3H);

MS m/z (ESI): 486.2 [M+H]⁺.

Example 58

(R)-5-(4-Cyclopropyl-1H-imidazol-1-yl)-2-fluoro-N-(6-(5-isopropyl-6,7-dihydro-5H-pyrrolo[2,1-c][1,2,4]triazol-3-yl)pyridin-2-yl)-4-methylbenzamide

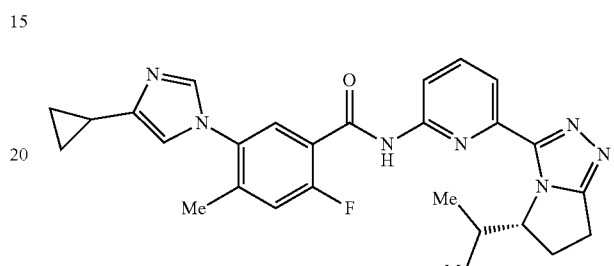

(R)-5-(4-Cyclopropyl-1H-imidazol-1-yl)-2-fluoro-N-(6-(5-isopropyl-6,7-dihydro-5H-pyrrolo[2,1-c][1,2,4]triazol-3-yl)pyridin-2-yl)-4-methylbenzamide was prepared in accordance with Example 8.

¹H NMR (400 MHz, CDCl₃) δ 9.00 (d, J=15.6 Hz, 1H), 8.46-8.26 (m, 1H), 8.10-7.99 (m, 2H), 7.80 (m, 1H), 7.43 (t, J=8.8 Hz, 1H), 7.14 (d, J=12.6 Hz, 1H), 6.73 (s, 1H), 4.86-4.61 (m, 1H), 3.00-2.81 (m, 2H), 2.76 (m, 1H), 2.60-2.47 (m, 2H), 2.22 (s, 3H), 1.85 (m, 1H), 1.01 (d, J=7.0 Hz, 3H), 0.84 (m, 2H), 0.80-0.74 (m, 2H), 0.60 (m, 3H);

MS m/z (ESI): 486.2 [M+H]⁺.

Example 59

(R)-5-(4-Cyclopropyl-1H-imidazol-1-yl)-2-fluoro-4-methyl-N-(6-(5-propyl-6,7-dihydro-5H-pyrrolo[2,1-c][1,2,4]triazol-3-yl)pyridin-2-yl)benzamide

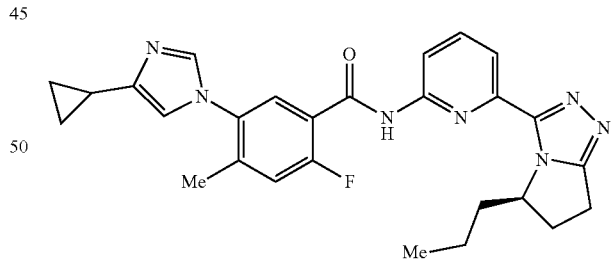

(R)-5-(4-Cyclopropyl-1H-imidazol-1-yl)-2-fluoro-4-methyl-N-(6-(5-propyl-6,7-dihydro-5H-pyrrolo[2,1-c][1,2,4]triazol-3-yl)pyridin-2-yl)benzamide was prepared in accordance with the method of Example 55.

¹H NMR (400 MHz, CDCl₃) δ 9.03 (d, J=15.3 Hz, 1H), 8.37 (d, J=8.0 Hz, 1H), 8.15-8.06 (m, 2H), 7.89 (t, J=8.0 Hz, 1H), 7.51 (s, 1H), 7.21 (d, J=12.5 Hz, 1H), 6.84-6.78 (m, 1H), 4.95-4.86 (m, 1H), 3.09-2.89 (m, 3H), 2.60-2.50 (m, 1H), 2.30 (s, 3H), 2.04-1.99 (m, 1H), 1.95-1.89 (m, 1H), 1.71-1.63 (m, 1H), 1.49-1.36 (m, 2H), 0.97 (t, J=7.3 Hz, 3H), 0.93-0.88 (m, 2H), 0.87-0.82 (m, 2H);

MS m/z (ESI): 486.2 [M+H]⁺.

Example 60

(S)-5-(4-Cyclopropyl-1H-imidazol-1-yl)-2-fluoro-4-methyl-N-(6-(5-propyl-6,7-dihydro-5H-pyrrolo[2,1-c][1,2,4]triazol-3-yl)pyridin-2-yl)benzamide

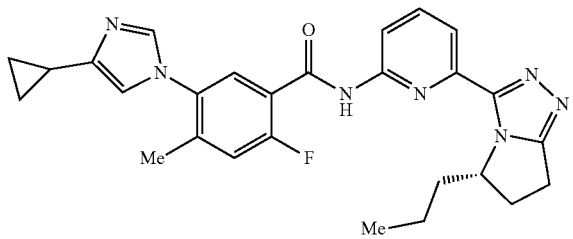 [SMILES: CCC[C@H]1CCc2nnc(-c3cccc(NC(=O)c4cc(-n5cnc(C6CC6)c5)c(C)cc4F)n3)n21]

(S)-5-(4-Cyclopropyl-1H-imidazol-1-yl)-2-fluoro-4-methyl-N-(6-(5-propyl-6,7-dihydro-5H-pyrrolo[2,1-c][1,2,4]triazol-3-yl)pyridin-2-yl)benzamide was prepared in accordance with the method of Example 55.

$^1$H NMR (400 MHz, CDCl$_3$) δ 9.03 (d, J=15.3 Hz, 1H), 8.37 (d, J=8.0 Hz, 1H), 8.15-8.06 (m, 2H), 7.89 (t, J=8.0 Hz, 1H), 7.51 (s, 1H), 7.21 (d, J=12.5 Hz, 1H), 6.84-6.78 (m, 1H), 4.95-4.86 (m, 1H), 3.09-2.89 (m, 3H), 2.60-2.50 (m, 1H), 2.30 (s, 3H), 2.04-1.99 (m, 1H), 1.95-1.89 (m, 1H), 1.71-1.63 (m, 1H), 1.49-1.36 (m, 2H), 0.97 (t, J=7.3 Hz, 3H), 0.93-0.88 (m, 2H), 0.87-0.82 (m, 2H);

MS m/z (ESI): 486.2 [M+H]$^+$.

Example 61

5-(4-Cyclopropyl-1H-imidazol-1-yl)-N-(6-(6',7'-dihydrospiro[cyclopropane-1,5'-pyrrolo[2,1-c][1,2,4]triazol]-3'-yl)pyridin-2-yl)-2-fluoro-4-methylbenzamide

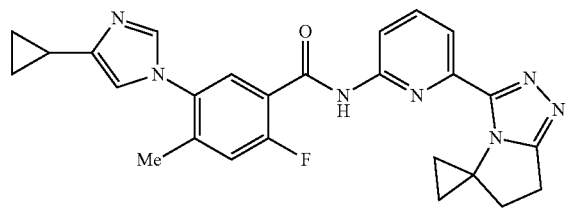 [SMILES: Cc1cc(F)c(C(=O)Nc2cccc(-c3nnc4n3C3(CC4)CC3)n2)cc1-n1cnc(C2CC2)c1]

Step 1: Preparation of 5-methoxy-4-azaspiro[2.4]hept-4-ene

Trimethyloxonium tetrafluoroborate (3.55 g, 24.0 mmol) was added to a solution of 4-azaspiro[2.4]heptan-5-one (1.7 g, 17.2 mmol) in dichloromethane (60 mL) in batches in an ice bath. The reaction solution was warmed up to room temperature slowly, and stirred at this temperature for 5 hours. The reaction solution was added with saturated aqueous NaHCO$_3$ solution (5 mL), and extracted with dichloromethane (50 mL×2). The organic phase was washed with saturated brine, dried over anhydrous sodium sulfate, added with glacial acetic acid (5 mL), and concentrated under reduced pressure to obtain the crude product, which was used directly in the next step.

MS m/z (ESI): 126.2 [M+H]$^{-1}$.

Step 2: Preparation of 6-(6',7'-dihydrospiro[cyclopropane-1,5'-pyrrolo[2,1-c][1,2,4]triazol]-3'-yl)pyridin-2-amine

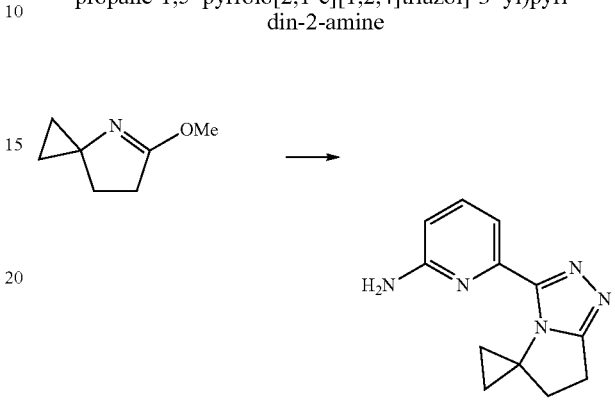

6-Aminopicolinohydrazide (500 mg, 4.5 mmol) was dissolved in 2-pentanol (15 mL) and acetic acid (1 mL) at room temperature, and then 5-methoxy-4-azaspiro[2.4]hept-4-ene (930 mg, 6.3 mmol) was added. The reaction solution was heated to 125° C., and stirred at this temperature for 12 hours. After cooling to room temperature, the reaction solution was concentrated under reduced pressure. The residue was added with saturated aqueous NaHCO$_3$ solution (5 mL), and extracted with dichloromethane (50 mL×2). The organic phase was washed with saturated brine, dried over anhydrous sodium sulfate, concentrated to remove the organic solvent. The residue was subjected to column chromatography to obtain the title compound 6-(6',7'-dihydrospiro[cyclopropane-1,5'-pyrrolo[2,1-c][1,2,4]triazol]-3'-yl)pyridin-2-amine (515 mg, yield of two steps: 50%).

$^1$H NMR (400 MHz, CDCl$_3$) δ 7.60-7.44 (m, 2H), 6.57-6.47 (m, 1H), 4.31 (s, 2H), 3.21-3.05 (m, 2H), 2.79-2.67 (m, 2H), 2.13-2.05 (m, 2H), 0.86-0.79 (m, 2H);

MS m/z (ESI): 228.2 [M+H]$^{-1}$.

Step 3: Preparation of 5-(4-cyclopropyl-1H-imidazol-1-yl)-N-(6-(6',7'-dihydrospiro[cyclopropane-1,5'-pyrrolo[2,1-c][1,2,4]triazol]-3'-yl)pyridin-2-yl)-2-fluoro-4-methylbenzamide

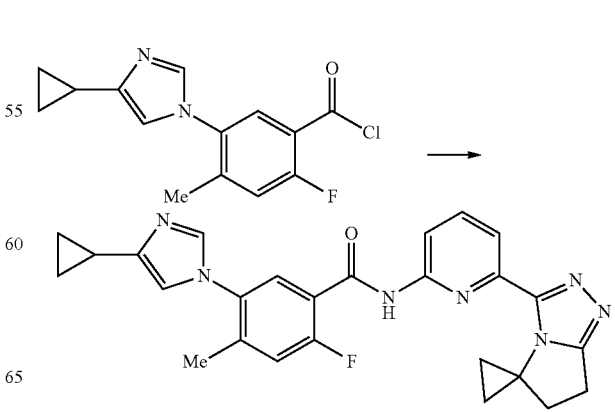

6-(6',7'-Dihydrospiro[cyclopropane-1,5'-pyrrolo[2,1-c][1,2,4]triazol]-3'-yl)pyridin-2-amine (39 mg, 0.17 mmol) was added to a solution of 5-(4-cyclopropyl-1H-imidazol-1-yl)-2-fluoro-4-methylbenzoyl chloride (80 mg, 0.29 mmol) in THF (5 mL) and pyridine (5 mL) at room temperature, and then 4-dimethylaminopyridine (5.3 mg, 0.043 mmol) was added. The reaction solution was heated to 45° C., and stirred at this temperature for 2 hours. The reaction solution was added with water (5 mL), and extracted with dichloromethane (50 mL×2). The organic phase was washed with saturated brine, dried over anhydrous sodium sulfate, and concentrated to remove the organic solvent. The residue was subjected to column chromatography to obtain the title compound 5-(4-cyclopropyl-1H-imidazol-1-yl)-N-(6-(6',7'-dihydrospiro[cyclopropane-1,5'-pyrrolo[2,1-c][1,2,4]triazol]-3'-yl)pyridin-2-yl)-2-fluoro-4-methylbenzamide (51 mg, yield: 63%).

$^{1}$H NMR (400 MHz, CDCl$_{3}$) δ 9.05 (d, J=16.6 Hz, 1H), 8.33-8.31 (m, 1H), 8.09 (d, J=7.4 Hz, 1H), 8.06-7.99 (m, 1H), 7.86 (t, J=8.0 Hz, 1H), 7.46 (s, 1H), 7.21 (d, J=12.6 Hz, 1H), 6.80 (s, 1H), 3.17 (t, J=7.6 Hz, 2H), 2.80 (t, J=7.8 Hz, 2H), 2.30 (s, 3H), 2.19-2.05 (m, 2H), 1.98-1.84 (m, 1H), 1.00-0.87 (m, 4H), 0.87-0.78 (m, 2H);

MS m/z (ESI): 470.2 [M+H]$^{+}$.

Example 62

N-(6-(6',7'-Dihydrospiro[cyclopropane-1,5'-pyrrolo[2,1-c][1,2,4]triazol]-3'-yl)pyridin-2-yl)-2-fluoro-5-(4-isopropyl-1H-imidazol-1-yl)-4-methylbenzamide

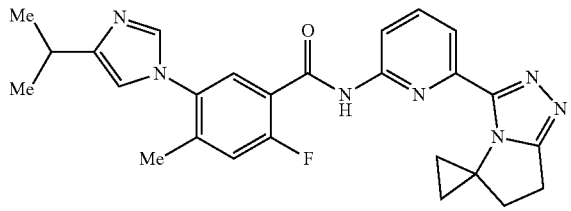 [SMILES: Cc1cc(F)c(C(=O)Nc2cccc(-c3nnc4n3C3(CC4)CC3)n2)cc1-n1cnc(C(C)C)c1]

N-(6-(6',7'-Dihydrospiro[cyclopropane-1,5'-pyrrolo[2,1-c][1,2,4]triazol]-3'-yl)pyridin-2-yl)-2-fluoro-5-(4-isopropyl-1H-imidazol-1-yl)-4-methylbenzamide was prepared in accordance with Example 61.

$^{1}$H NMR (400 MHz, CDCl$_{3}$) δ 9.06 (d, J=16.6 Hz, 1H), 8.31 (m, 1H), 8.05 (m, 2H), 7.86 (t, J=8.0 Hz, 1H), 7.57 (s, 1H), 7.22 (d, J=12.4 Hz, 1H), 6.77 (s, 1H), 3.17 (t, J=7.6 Hz, 2H), 2.99 (m, 1H), 2.80 (t, J=7.8 Hz, 2H), 2.31 (s, 3H), 2.19-2.12 (m, 2H), 1.33 (d, J=6.8 Hz, 6H), 0.98 (m, 2H);

MS m/z (ESI): 472.2 [M+H]$^{+}$.

Example 63

6-(4-Cyclopropyl-1H-imidazol-1-yl)-2-(6-(6,7-dihydro-5H-pyrrolo[2,1-c][1,2,4]triazol-3-yl)pyridin-2-yl)-5-methylisoindolin-1-one

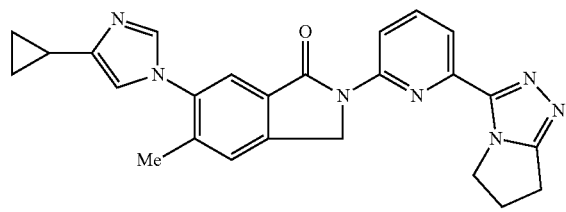 [SMILES: Cc1cc2c(cc1-n1cnc(C3CC3)c1)C(=O)N(c1cccc(-c3nnc4n3CCC4)n1)C2]

Step 1: Preparation of methyl 5-amino-2-cyano-4-methylbenzoate

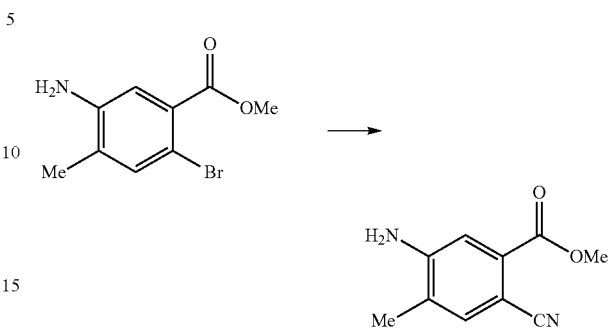

Methyl 5-amino-2-bromo-4-methylbenzoate (900 mg, 3.69 mmol) and CuCN (657 mg, 7.38 mmol) were mixed in NMP (10 mL), and stirred at 180° C. for 2 hours. After cooling, the reaction solution was added with water and filtrated. The filter cake was dried to obtain the crude title compound methyl 5-amino-2-cyano-4-methylbenzoate (1.5 g), which was used directly in the next step.

MS m/z (ESI): 191.1 [M+H]$^{+}$.

Step 2: Preparation of 6-amino-5-methylisoindolin-1-one

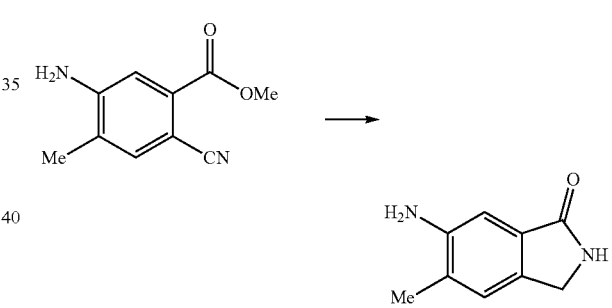

The above crude product was dissolved in methanol (20 mL). The reaction solution was added with Raney Ni (approximately 100 mg), and stirred in a H2 atmosphere (2~3 atm) at room temperature overnight. The reaction solution was filtered through celite to remove the catalyst. The filtrate was concentrated, and the residue was subjected to column chromatography to obtain the title compound 6-amino-5-methylisoindolin-1-one (800 mg, a crude product).

MS m/z (ESI): 163.1 [M+H]$^{+}$.

Step 3: Preparation of 6-((2-cyclopropyl-2-oxoethyl)amino)-5-methylisoindolin-1-one

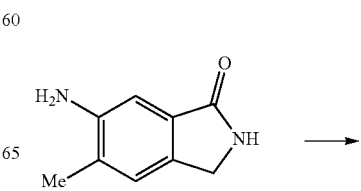

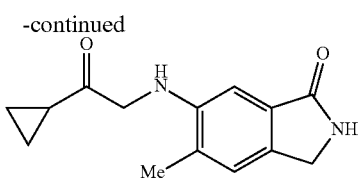

6-Amino-5-methylisoindolin-1-one (370 mg, 2.28 mmol), 2-bromo-1-cyclopropylethan-1-one (409 mg, 2.51 mmol), KI (38.0 mg, 0.228 mmol) and K₂CO₃ (378 mg, 2.74 mmol) were mixed in DMF (5 mL), and stirred at 55° C. for 2 hours. The reaction solution was cooled, added with water, and extracted with dichloromethane twice. The organic phases were combined, washed with saturated brine three times, dried and concentrated under reduced pressure to remove the organic solvent and obtain the crude product, which was used directly in the next step.

MS m/z (ESI): 245.1 [M+H]$^+$.

Step 4: Preparation of 6-(4-cyclopropyl-2-thiol-1H-imidazol-1-yl)-5-methylisoindolin-1-one

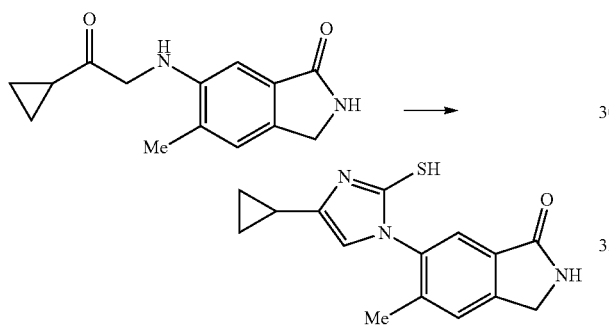

The crude product in Step 3 was dissolved in AcOH (10 mL). The reaction solution was added with KSCN (442 mg, 4.56 mmol), and stirred at 120° C. for 2 hours. After cooling, the reaction solution was concentrated to obtain the crude product, which was used directly in the next step.

MS m/z (ESI): 286.1 [M+H]$^+$.

Step 5: Preparation of 6-(4-cyclopropyl-1H-imidazol-1-yl)-5-methylisoindolin-1-one

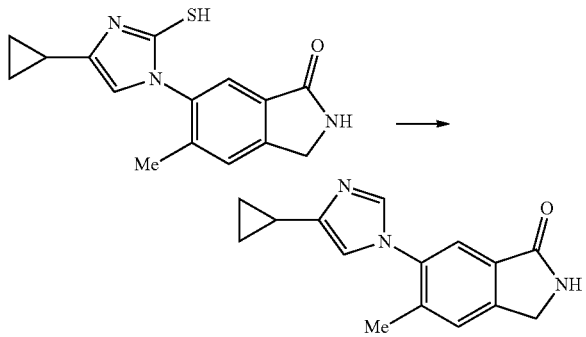

The crude product in Step 4 was dissolved in a mixed solvent of AcOH (10 mL) and water (2 mL), and stirred. The reaction solution was slowly added dropwise with hydrogen peroxide (30 wt %, 10.0 g, 87.8 mmol) at 50° C. After completion of the addition, the reaction solution was stirred at this temperature for 1 hour. The reaction solution was cooled, slowly added with 20 wt % aqueous Na₂SO₃ solution (30 mL), and stirred at room temperature for 30 minutes. The reaction solution was concentrated under reduced pressure to remove the organic solvent, and the aqueous phase was extracted with dichloromethane twice. The organic phases were combined, washed with saturated aqueous sodium bicarbonate solution and saturated brine successively, dried over anhydrous sodium sulfate, and concentrated under reduced pressure. The residue was subjected to column chromatography to obtain the title compound 6-(4-cyclopropyl-1H-imidazol-1-yl)-5-methylisoindolin-1-one (180 mg, yield of five steps: 42%).

MS m/z (ESI): 254.1 [M+H]$^+$.

Step 6: Preparation of 3-(6-chloropyridin-2-yl)-6,7-dihydro-5H-pyrrolo[2,1-c][1,2,4]triazole

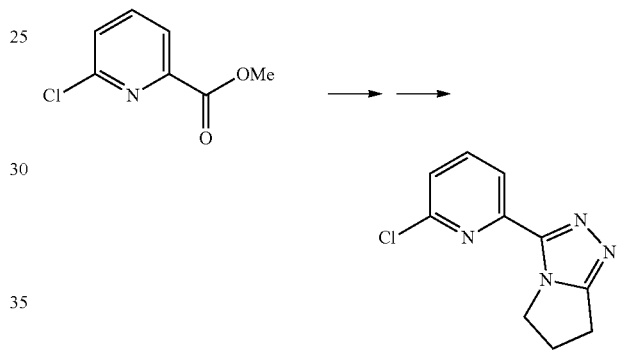

3-(6-Chloropyridin-2-yl)-6,7-dihydro-5H-pyrrolo[2,1-c][1,2,4]triazole was prepared in accordance with Steps 5 and 6 of Example 1.

MS m/z (ESI): 221.1 [M+H]$^+$.

Step 7: Preparation of 6-(4-cyclopropyl-1H-imidazol-1-yl)-2-(6-(6,7-dihydro-5H-pyrrolo[2,1-c][1,2,4]triazol-3-yl)pyridin-2-yl)-5-methylisoindolin-1-one

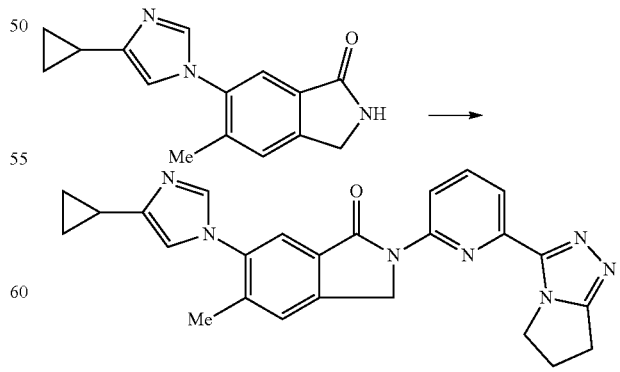

6-(4-Cyclopropyl-1H-imidazol-1-yl)-5-methylisoindolin-1-one (50 mg, 0.197 mmol), 2-chloro-6-(4-isopropyl-4H-1,2,4-triazol-3-yl)pyridine (48 mg, 0.22 mmol) and cesium carbonate (86 mg, 0.30 mm) were mixed in 1,4-dioxane (4 mL). The reaction system was purged with nitrogen for 5 minutes, and then Pd$_2$(dba)$_3$ (18 mg, 0.02 mmol) was added. The reaction system was purged with nitrogen for another five minutes, and then Xantphos (23 mg, 0.04 mmol) was added. The reaction system was purged with nitrogen for five minutes, and then stirred at 120° C. for two days. The reaction solution was cooled, concentrated, and added with dichloromethane and water, and two phases were separated. The organic phase was collected, washed with saturated brine, dried over anhydrous sodium sulfate, and concentrated to remove the organic solvent. The residue was purified by preparative thin layer chromatography to obtain the title compound 6-(4-cyclopropyl-1H-imidazol-1-yl)-2-(6-(6,7-dihydro-5H-pyrrolo[2,1-c][1,2,4]triazol-3-yl)pyridin-2-yl)-5-methylisoindolin-1-one (43 mg, yield: 50%).

$^1$H NMR (400 MHz, CDCl$_3$) δ 8.63 (d, J=8.0 Hz, 1H), 8.04 (d, J=8.0 Hz, 1H), 7.84 (t, J=8.0 Hz, 1H), 7.76 (s, 1H), 7.48 (s, 1H), 6.84 (s, 1H), 5.08 (s, 2H), 4.48 (t, J=7.2 Hz, 2H), 2.88 (m, 2H), 2.35 (s, 3H), 1.93 (m, 1H), 0.91 (m, 2H), 0.85 (m, 2H);

MS m/z (ESI): 438.2 [M+H]$^+$.

Example 64

6-(4-Cyclopropyl-1H-imidazol-1-yl)-2-(6-(6',7'-dihydrospiro[cyclopropane-1,5'-pyrrolo[2,1-c][1,2,4]triazol]-3'-yl)pyridin-2-yl)-5-methylisoindolin-1-one

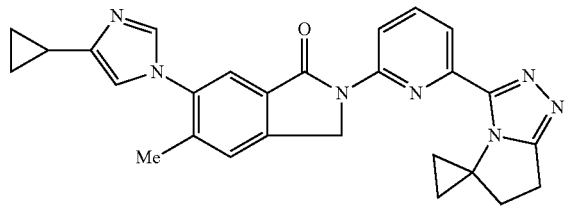 [SMILES: Cc1cc2c(cc1-n1cnc(C3CC3)c1)C(=O)N(c1cccc(-c3nnc4n3C3(CC4)CC3)n1)C2]

6-(4-Cyclopropyl-1H-imidazol-1-yl)-2-(6-(6',7'-dihydrospiro[cyclopropane-1,5'-pyrrolo[2,1-c][1,2,4]triazol]-3'-yl)pyridin-2-yl)-5-methylisoindolin-1-one was prepared in accordance with Example 63.

$^1$H NMR (400 MHz, CDCl$_3$) δ 8.70 (d, J=8.0 Hz, 1H), 7.95 (d, J=7.2 Hz, 1H), 7.87 (t, J=8.0 Hz, 1H), 7.78 (s, 1H), 7.56 (s, 1H), 7.49 (s, 1H), 6.63 (s, 1H), 5.13 (s, 2H), 3.19 (t, J=7.6 Hz, 2H), 2.80 (t, J=7.6 Hz, 2H), 2.35 (s, 3H), 1.93 (m, 3H), 1.01 (m, 2H), 0.88 (m, 4H);

MS m/z (ESI): 464.2 [M+H]$^+$.

Example 65

(S)-6-(4-Cyclopropyl-1H-imidazol-1-yl)-5-methyl-2-(6-(5-(trifluoromethyl)-6,7-dihydro-5H-pyrrolo[2,1-c][1,2,4]triazol-3-yl)pyridin-2-yl)isoindolin-1-one

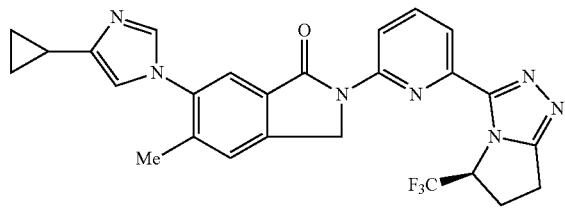 [SMILES: Cc1cc2c(cc1-n1cnc(C3CC3)c1)C(=O)N(c1cccc(-c3nnc4n3[C@H](C(F)(F)F)CC4)n1)C2]

(S)-6-(4-Cyclopropyl-1H-imidazol-1-yl)-5-methyl-2-(6-(5-(trifluoromethyl)-6,7-dihydro-5H-pyrrolo[2,1-c][1,2,4]triazol-3-yl)pyridin-2-yl)isoindolin-1-one was prepared in accordance with Example 63.

$^1$H NMR (400 MHz, CDCl$_3$) δ 8.67 (d, J=8.0 Hz, 1H), 8.04 (d, J=7.6 Hz, 1H), 7.85 (t, J=8.0 Hz, 1H), 7.77 (s, 1H), 7.56 (s, 1H), 7.50 (s, 1H), 6.84 (s, 1H), 5.58 (m, 1H), 5.10 (d, J=13.2 Hz, 1H), 4.91 (d, J=13.2 Hz, 1H), 3.19 (m, 2H), 3.00 (m, 2H), 2.35 (s, 3H), 1.94 (m, 1H), 0.90 (m, 4H);

MS m/z (ESI): 506.2 [M+F1]$^+$.

Biological Assay and Evaluation

The present invention is further described below in combination with the following test examples, which are not intended to limit the scope of the present invention.

1. ASK1 Enzymatic Test

In this test, the fluorescence-resonance energy transfer (TR-FRET) method was used to determine the inhibition effect of the test compounds on ASK1 kinase activity, and the half maximal inhibitory concentration IC$_{50}$ of the compounds on ASK1 kinase activity was obtained.

1) 1~5 μL of ASK1 enzyme solution was added to a 384-well plate, and the final concentration of the enzyme was 0.220 nM.

2) 1~5 μL of gradient-diluted compound solution was added.

3) 1~5 μL of a substrate mixture containing substrate polypeptides (final concentration: 100~5000 nM) and ATP (final concentration: 100~1000 uM) were added.

4) The mixture was incubated at room temperature for 0.5 to 5 hours.

5) 10 μL of EDTA and test solution containing labeled antibody were added, and the plate was incubated at room temperature for 2 to 24 hours.

6) The fluorescence signal value of each well was determined by a microplate reader at about 615 nm and 665 nm.

7) The inhibition rate was calculated by the fluorescence signal value.

8) The IC$_{50}$ of the compound was obtained by curve fitting according to the inhibition rate at different concentrations.

The enzymatic activities of the compounds of the examples in the present invention are shown in Table 1.

TABLE 1

| Enzymatic activities of the compounds of the examples in the present invention | |
|---|---|
| Compound No. | ASK1 IC$_{50}$ (nM) |
| Example 1 | 6.0 |
| Example 2 | 9.3 |
| Example 3 | 13.4 |
| Example 4 | 47.8 |
| Example 7 | 19.6 |
| Example 8 | 1.8 |
| Example 9 | 5.0 |
| Example 10 | 1.0 |
| Example 11 | 10.6 |
| Example 13 | 2.7 |
| Example 14 | 9.0 |
| Example 15 | 1.4 |
| Example 16 | 4.1 |
| Example 30 | 11.4 |
| Example 31 | 10.9 |
| Example 32 | 4.9 |
| Example 33 | 7.2 |
| Example 34 | 5.2 |
| Example 36 | 9.1 |
| Example 37 | 3.5 |

TABLE 1-continued

Enzymatic activities of the compounds of the examples in the present invention

| Compound No. | ASK1 IC$_{50}$ (nM) |
|---|---|
| Example 38 | 4.1 |
| Example 40 | 1.9 |
| Example 41 | 7.7 |
| Example 43 | 1.9 |
| Example 44 | 3.6 |
| Example 48 | 6.1 |
| Example 50 | 9.6 |
| Example 51 | 4.9 |
| Example 53 | 8.2 |
| Example 55 | 1.9 |
| Example 56 | 5.0 |
| Example 59 | 2.9 |
| Example 60 | 6.6 |
| Example 61 | 1.9 |
| Example 62 | 3.0 |
| Example 63 | 8.4 |
| Example 64 | 5.5 |
| Example 65 | 9.4 |

The above compounds of the examples all significantly inhibit the enzymatic activity of ASK1 kinase, and some compounds show a strong inhibition effect on ASK1 kinase, with IC$_{50}$ of inhibition of kinase activity less than 10 nM. These compounds, as potent ASK1 inhibitors, have a great potential in the treatment of NASH.

2. Pharmacokinetic (PK) Assay in Mice

The pharmacokinetic test of the preferred examples of the present invention in mice was carried out in Balb/c male mice (Shanghai Jiesijie Laboratory Animal Co., LTD).

Administration mode: single intragastric administration.
Administration dosage: 5 mg/10 ml/kg.
Formulation: 0.5% CMC-Na, ultrasonic dissolution.
Sampling points: 0.5, 1, 2, 4, 6, 8 and 24 hours after administration.
Sample process:

1) 0.1 mL of blood was taken from the orbit, placed in a K$_2$EDTA tube, and centrifuged for 5~20 min at room temperature at 1000~3000×g to separate the plasma, which was then stored at −80° C.

2) 160 µL of acetonitrile was added to 40 µL of plasma sample for precipitation, and then the mixture was centrifuged for 5~20 minutes at 500~2000×g.

3) 100 µL, of processed supernatant was taken and analyzed by LC/MS/MS assay to determine the concentration of the test compound.

LC-MS/MS Assay:
Liquid chromatography condition: Shimadzu LC-20AD pump
Mass spectrometry condition: AB Sciex API 4000 mass spectrometer
Chromatographic column: phenomenex Gemiu 5 µm C18 50×4.6 mm
Mobile phase: solution A was 0.1% aqueous formic acid solution, and solution B was acetonitrile
Flow rate: 0.8 mL/min
Elution time: 0-3.5 minutes gradient elution
Pharmacokinetics:

The main parameters were calculated using WinNonlin 6.1. The experimental results of the pharmacokinetic assay in mice are shown in Table 3 below:

TABLE 3

| | Pharmacokinetic assay (5 mg/kg) | | | | | |
|---|---|---|---|---|---|---|
| Example No. | Peak time $t_{max}$ (ng/mL) | Plasma concentration $C_{max}$ (ng/mL) | Area under curve AUC$_{0-t}$ (ng/mL × h) | Area under curve AUC$_{0-\infty}$ (ng/mL × h) | Half-life $t_{1/2}$ (h) | Mean residence time MRT (h) |
| 1 | 0.5 | 18267 | 104269 | 104291 | 2.9 | 4.2 |
| 8 | 1.0 | 4811 | 29682 | 29770 | 2.7 | 4.6 |
| 9 | 0.5 | 4373 | 38067 | 38413 | 4.4 | 5.5 |
| 10 | 0.5 | 8990 | 32427 | 32433 | 1.6 | 3.0 |
| 11 | 1.0 | 13177 | 29420 | 29422 | 1.1 | 2.1 |
| 13 | 1.0 | 5056 | 11698 | 11811 | 1.0 | 2.0 |
| 14 | 1.0 | 6150 | 20980 | 20987 | 1.3 | 2.8 |
| 16 | 1.0 | 6583 | 13599 | 13882 | 1.4 | 2.0 |
| 32 | 1.0 | 10923 | 46379 | 46391 | 2.6 | 3.9 |
| 33 | 0.5 | 5168 | 47861 | 48568 | 4.7 | 5.9 |
| 34 | 1.0 | 13467 | 81090 | 81176 | 2.5 | 4.4 |
| 35 | 1.0 | 13500 | 107169 | 107595 | 3.7 | 5.0 |
| 37 | 0.5 | 11733 | 43865 | 48024 | 2.1 | 3.4 |
| 38 | 0.5 | 19367 | 129328 | 130413 | 2.8 | 5.1 |
| 40 | 0.5 | 10700 | 26801 | 28270 | 1.7 | 2.7 |
| 41 | 1.0 | 17067 | 83887 | 83941 | 2.0 | 4.0 |
| 43 | 0.5 | 12167 | 80874 | 81897 | 3.9 | 5.3 |
| 51 | 1.0 | 5890 | 57157 | 57663 | 3.5 | 5.8 |
| 52 | 0.5 | 9967 | 70497 | 70569 | 3.0 | 4.7 |
| 55 | 0.5 | 9327 | 31515 | 31543 | 1.4 | 2.9 |
| 56 | 1.0 | 9937 | 38596 | 42464 | 2.4 | 3.6 |
| 59 | 1.0 | 7590 | 19686 | 20228 | 1.4 | 2.3 |
| 60 | 1.0 | 9180 | 29048 | 29854 | 1.3 | 2.6 |
| 61 | 1.0 | 11383 | 68649 | 68761 | 2.7 | 4.5 |

It can be seen from the results of the pharmacokinetics assay in mice in the table that the compounds of the examples of the present invention showed good metabolic properties, and both the exposure AUC and the maximum plasma concentration Cmax were good.

3. The effect of the compounds of the present invention on the ALT and AST levels of non-alcoholic steatohepatitis mice induced by HFD (high fat diet)+CCl$_4$ 1. Test Object:

The object of this test example is to determine whether the compounds of the present invention can down-regulate the ALT and AST levels in the serum of non-alcoholic steatohepatitis mice or not.

2. Test Materials and Instruments:

Alanine aminotransfease (ALT/GPT) kit: Nanjing Jiancheng Technology Co., Ltd.

Aspartate aminotransferase (AST/GOT) kit: Nanjing Jiancheng Technology Co., Ltd.

96-Well plate: Corning Co.;

BioTek Synergy H1 microplate reader: BioTek Co., USA

3. Test Process:

C57BL/6 mice were adaptively fed in a SPF (specific pathogen free) barrier for 3 to 7 days, and then fed with HFD feed with a feeding cycle of 8 weeks. At the fifth week of HFD feeding, the HFD-induced mice were randomly grouped according to body weight, and orally administrated with CCl$_4$ twice a week for 4 weeks. At the day of modeling with CCl$_4$, the test compounds were orally administrated once a day continuously for 28 days. The solvent control group was administrated with the corresponding solvent of the test compounds with an administration volume of 10 mL/kg. The mice were euthanized with CO$_2$ 48 hours after the last administration of CCl$_4$, and the non-anticoagulated venous blood was collected from the heart. The whole blood was left to stand at room temperature for at least 30 minutes, and then centrifuged for 5 minutes at 4° C. at 5000 rpm to separate the serum. The serum was dispensed into two portions in 1.5 mL EP tubes, and stored at −80° C. for later use.

The ALT and AST levels in mice serum were determined using the alanine aminotransfease (ALT/GPT) kit and aspartate aminotransferase (AST/GOT) kit. The ALT (or AST) test substrate solution was preheated in a 37° C. incubator; 20 μL of substrate solution were pipetted into a 96-well plate, and 5 μL of serum were pipetted into the 96-well plate as test well. After mixing well, the plate was sealed using a sealing film, and placed into the 37° C. incubator to incubate for 30 min. The ALT (or AST) standard curve was formulated, and 25 μL of which were pipetted into the 96-well plate; 20 μL of blood were pipetted into the 96-well plate as control well; 20 μL of 2,4-dinitrophenylhydrazine solution were added to each well. After mixing well, the plate was sealed using a sealing film, and placed into the 37° C. incubator to incubate for 20 min. 200 μL of 0.4 M NaOH solution were added to each well. The plate was placed on a shaker to shake for 15 min, and then measured on the BioTek Synergy H1 instrument using OD detection program at a wavelength of 510 nm. The absolute OD value was calculated from the OD value of each well. Absolute OD value=OD value of measured well−OD value of control well. The absolute OD value was taken into the standard curve to obtain the ALT (or AST) content of the sample. Samples that exceed the standard curve range should be re-tested after diluting the serum to an appropriate concentration.

Data processing: (% ALT reduction rate)=(solvent control group−test compound)/solvent control group×100%;

(% AST reduction rate)=(solvent control group−test compound)/solvent control group×100%.

4. Test Results:

|  | ALT(U/L) reduction rate (%) | AST(U/L) reduction rate (%) |
| --- | --- | --- |
| Solvent control group | — | — |
| GS-4997 | 40% | 35% |
| Example 10 | 50% | 46% |
| Example 15 | 54% | 58% |
| Example 37 | 57% | 62% |
| Example 40 | 50% | 65% |
| Example 43 | 65% | 58% |
| Example 55 | 56% | 55% |
| Example 61 | 50% | 54% |
| Example 64 | 51% | 47% |
| Example 65 | 46% | 52% |

5. Test Conclusion:

The compounds of the present invention showed a good effect in down-regulating the ALT and AST levels in the serum of non-alcoholic steatohepatitis mice.

What is claimed is:

1. A compound of formula (III):

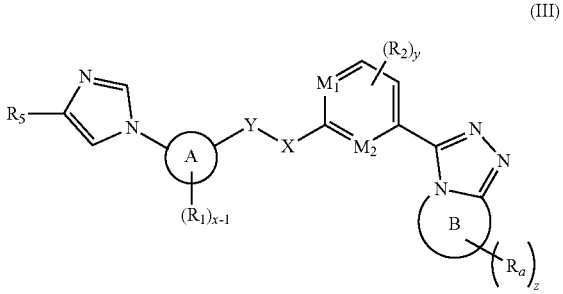

or a pharmaceutically acceptable salt or stereoisomer thereof, wherein:

ring A is phenylene, wherein the phenylene is optionally substituted by one or more substituents independently selected from the group consisting of deuterium, halogen, nitro, cyano, alkyl, deuterated alkyl, hydroxyalkyl, —(CH$_2$)$_n$C(O)R$_9$, —(CH$_2$)$_n$C(O)NR$_{10}$R$_{11}$, —(CH$_2$)$_n$C(O)OR$_9$, —(CH$_2$)$_n$NR$_{10}$R$_{11}$, —(CH$_2$)$_n$NR$_{10}$C(O)R$_9$, —(CH$_2$)$_n$NR$_{10}$S(O)$_m$R$_9$, —(CH$_2$)$_n$OR$_9$, —(CH$_2$)$_n$S(O)$_m$R$_9$, cycloalkyl, heterocyclyl, aryl, and heteroaryl;

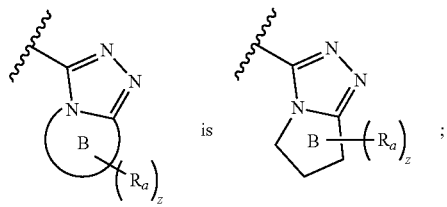

M₁ is CR₆;
M₂ is N;
X is —NR₇—;
Y is —C(O)—;
each $R_a$ is independently halogen, nitro, cyano, alkyl, deuterated alkyl, haloalkyl, hydroxyalkyl, —(CR₉R₁₀)ₙ—, alkenyl, alkynyl, —(CH₂)ₙC(O)R₉, —(CH₂)ₙC(O)NR₁₀R₁₁, —(CH₂)ₙC(O)OR₉, —(CH₂)ₙNR₁₀R₁₁, —(CH₂)ₙR₁₀C(O)R₉, —(CH₂)ₙNR₁₀S(O)ₘR₉, —(CH₂)ₙOR₉, —(CH₂)ₙS(O)ₘR₉, cycloalkyl, heterocyclyl, aryl, or heteroaryl, wherein each alkyl, haloalkyl, alkenyl, alkynyl, cycloalkyl, heterocyclyl, aryl, and heteroaryl is optionally and independently substituted by one or more substituents independently selected from the group consisting of deuterium, halogen, nitro, cyano, alkyl, haloalkyl, hydroxyalkyl, alkenyl, alkynyl, —(CH₂)ₙC(O)R₁₂, —(CH₂)ₙC(O)NR₁₂R₁₃, —(CH₂)ₙC(O)OR₁₂, —(CH₂)ₙNR₁₂R₁₃, —(CH₂)ₙNR₁₃C(O)R₁₂, —(CH₂)ₙNR₁₃S(O)ₘR₁₂, —(CH₂)ₙOR₁₂, —(CH₂)ₙS(O)ₘR₁₂, cycloalkyl, heterocyclyl, aryl, and heteroaryl;
each R₁ is independently halogen or alkyl;
each R₂ is independently hydrogen;
R₅ is halogen, nitro, cyano, alkyl, deuterated alkyl, haloalkyl, hydroxyalkyl, —(CH₂)ₙC(O)R₁₂, —(CH₂)ₙC(O)NR₁₂R₁₃, —(CH₂)ₙC(O)OR₁₂, —(CH₂)ₙNR₁₂R₁₃, —(CH₂)ₙNR₁₃C(O)R₁₂, —(CH₂)ₙNR₁₃S(O)ₘR₁₂, —(CH₂)ₙOR₁₂, —(CH₂)ₙS(O)ₘR₁₂, cycloalkyl, heterocyclyl, aryl, or heteroaryl;
each R₆ is independently hydrogen, deuterium, halogen, nitro, cyano, alkyl, deuterated alkyl, haloalkyl, —(CH₂)ₙC(O)R₉, —(CH₂)ₙC(O)NR₁₀R₁₁, —(CH₂)ₙC(O)OR₉, —(CH₂)ₙNR₁₀R₁₁, —(CH₂)ₙNR₁₀C(O)R₉, —(CH₂)ₙNR₁₀S(O)ₘR₉, —(CH₂)ₙOR₉, —(CH₂)ₙS(O)ₘR₉, cycloalkyl, heterocyclyl, aryl, or heteroaryl, wherein each alkyl, haloalkyl, cycloalkyl, heterocyclyl, aryl, and heteroaryl is optionally and independently substituted by one or more substituents independently selected from the group consisting of deuterium, halogen, nitro, cyano, alkyl, haloalkyl, hydroxyalkyl, —(CH₂)ₙC(O)R₁₂, —(CH₂)ₙC(O)NR₁₂R₁₃, —(CH₂)ₙC(O)OR₁₂, —(CH₂)ₙNR₁₂R₁₃, —(CH₂)ₙNR₁₃C(O)R₁₂, —(CH₂)ₙNR₁₃S(O)ₘR₁₂, —(CH₂)ₙOR₁₂, —(CH₂)ₙS(O)ₘR₁₂, cycloalkyl, heterocyclyl, aryl, and heteroaryl;
R₇ is hydrogen, deuterium, halogen, nitro, cyano, alkyl, deuterated alkyl, haloalkyl, —(CH₂)ₙC(O)R₉, —(CH₂)ₙC(O)NR₁₀R₁₁, —(CH₂)ₙC(O)OR₉, —(CH₂)ₙNR₁₀R₁₁, —(CH₂)ₙNR₁₀C(O)R₉, —(CH₂)ₙNR₁₀S(O)ₘR₉, —(CH₂)ₙOR₉, —(CH₂)ₙS(O)ₘR₉, cycloalkyl, heterocyclyl, aryl, or heteroaryl, wherein the alkyl, haloalkyl, cycloalkyl, heterocyclyl, aryl, or heteroaryl is optionally substituted by one or more substituents independently selected from the group consisting of deuterium, halogen, nitro, cyano, alkyl, haloalkyl, hydroxyalkyl, —(CH₂)ₙC(O)R₁₂, —(CH₂)ₙC(O)NR₁₂R₁₃, —(CH₂)ₙC(O)OR₁₂, —(CH₂)ₙNR₁₂R₁₃, —(CH₂)ₙNR₁₃C(O)R₁₂, —(CH₂)ₙNR₁₃S(O)ₘR₁₂, —(CH₂)ₙOR₁₂, —(CH₂)ₙS(O)ₘR₁₂, cycloalkyl, heterocyclyl, aryl, and heteroaryl;
each R₉ is independently hydrogen, deuterium, alkyl, deuterated alkyl, haloalkyl, amino, hydroxy, alkoxy, haloalkoxy, cycloalkyl, heterocyclyl, aryl, or heteroaryl, wherein each alkyl, haloalkyl, cycloalkyl, heterocyclyl, aryl, and heteroaryl is optionally and independently substituted by one or more substituents independently selected from the group consisting of deuterium, halogen, nitro, cyano, alkyl, hydroxyalkyl, —(CH₂)ₙC(O)R₁₂, —(CH₂)ₙC(O)NR₁₂R₁₃, —(CH₂)ₙC(O)OR₁₂, —(CH₂)ₙNR₁₂R₁₃, —(CH₂)ₙNR₁₃C(O)R₁₂, —(CH₂)ₙNR₁₃S(O)ₘR₁₂, —(CH₂)ₙOR₁₂, —(CH₂)ₙS(O)ₘR₁₂, cycloalkyl, heterocyclyl, aryl, and heteroaryl;
each R₁₀ is independently hydrogen, deuterium, alkyl, deuterated alkyl, haloalkyl, amino, hydroxy, cycloalkyl, heterocyclyl, aryl, or heteroaryl, wherein each alkyl, cycloalkyl, heterocyclyl, aryl, and heteroaryl is optionally and independently substituted by one or more substituents independently selected from the group consisting of deuterium, halogen, nitro, cyano, alkyl, hydroxyalkyl, —(CH₂)ₙC(O)R₁₂, —(CH₂)ₙC(O)NR₁₂R₁₃, —(CH₂)ₙC(O)OR₁₂, —(CH₂)ₙNR₁₂R₁₃, —(CH₂)ₙNR₁₃C(O)R₁₂, —(CH₂)ₙNR₁₃S(O)ₘR₁₂, —(CH₂)ₙOR₁₂, —(CH₂)ₙS(O)ₘR₁₂, cycloalkyl, heterocyclyl, aryl, and heteroaryl;
each R₁₁ is independently hydrogen, deuterium, alkyl, deuterated alkyl, haloalkyl, amino, hydroxy, cycloalkyl, heterocyclyl, aryl, or heteroaryl, wherein each alkyl, cycloalkyl, heterocyclyl, aryl, and heteroaryl is optionally and independently substituted by one or more substituents independently selected from the group consisting of deuterium, halogen, nitro, cyano, alkyl, hydroxyalkyl, —(CH₂)ₙC(O)R₁₂, —(CH₂)ₙC(O)NR₁₂R₁₃, —(CH₂)ₙC(O)OR₁₂, —(CH₂)ₙNR₁₂R₁₃, —(CH₂)ₙNR₁₃C(O)R₁₂, —(CH₂)ₙNR₁₃S(O)ₘR₁₂, —(CH₂)ₙOR₁₂, —(CH₂)ₙS(O)ₘR₁₂, cycloalkyl, heterocyclyl, aryl, and heteroaryl;
each R₁₂ is independently hydrogen, deuterium, alkyl, deuterated alkyl, haloalkyl, amino, hydroxy, cycloalkyl, heterocyclyl, aryl, or heteroaryl, wherein each alkyl, cycloalkyl, heterocyclyl, aryl, and heteroaryl is optionally and independently substituted by one or more substituents independently selected from the group consisting of deuterium, halogen, nitro, cyano, alkyl, hydroxyalkyl, amino, hydroxy, alkoxy, cycloalkyl, heterocyclyl, aryl, and heteroaryl;
each R₁₃ is independently hydrogen, deuterium, alkyl, deuterated alkyl, haloalkyl, amino, hydroxy, cycloalkyl, heterocyclyl, aryl, or heteroaryl, wherein each alkyl, cycloalkyl, heterocyclyl, aryl, and heteroaryl is optionally and independently substituted by one or more substituents independently selected from the group consisting of deuterium, halogen, nitro, cyano, alkyl, hydroxyalkyl, amino, hydroxy, alkoxy, cycloalkyl, heterocyclyl, aryl, and heteroaryl;
each m is independently 0, 1, or 2;
each n is independently 0, 1, 2, 3, 4, or 5;
x-1 is 2;
y is 2; and
z is 1 or 2.

2. The compound according to claim 1, or a pharmaceutically acceptable salt or stereoisomer thereof, wherein each $R_a$ is independently cyano, $C_{1-8}$ alkyl, $C_{1-8}$ haloalkyl, $C_{1-8}$ cyanoalkyl, $C_{1-8}$ hydroxyalkyl, —$(CH_2)_{1-5}OR_9$, —$(CR_9R_{10})_n$—, $C_{2-8}$ alkenyl, $C_{2-8}$ alkynyl, OH, O(deuterium), O($C_{1-8}$ alkyl), O(deuterated alkyl), O(haloalkyl), O(cycloalkyl), O(heterocyclyl), O(aryl), O(heteroaryl), —$(CH_2)_nC(O)R_9$, or $C_{3-8}$ cycloalkyl.

3. The compound according to claim 1, or a pharmaceutically acceptable salt or stereoisomer thereof, wherein each $R_1$ is independently halogen or $C_{1-8}$ alkyl.

4. The compound according to claim 1, or a pharmaceutically acceptable salt or stereoisomer thereof, wherein $R_5$ is halogen, $C_{1-8}$ alkyl, $C_{1-8}$ haloalkyl, $C_{1-8}$ hydroxyalkyl, O($C_{1-8}$ alkyl), O($C_{1-8}$ haloalkyl), $C_{3-8}$ cycloalkyl, or 3- to 10-membered heterocyclyl.

5. The compound according to claim 1, wherein the compound is of formula (IV):

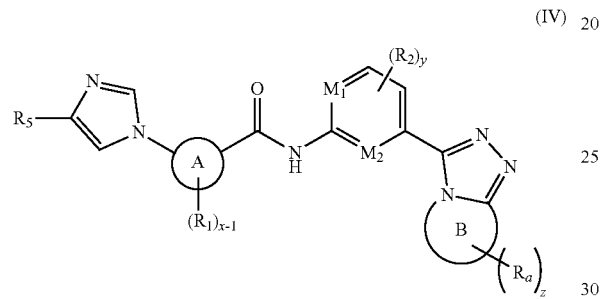

(IV)

or a pharmaceutically acceptable salt or stereoisomer thereof.

6. The compound according to claim 1, wherein the compound is of formula (V):

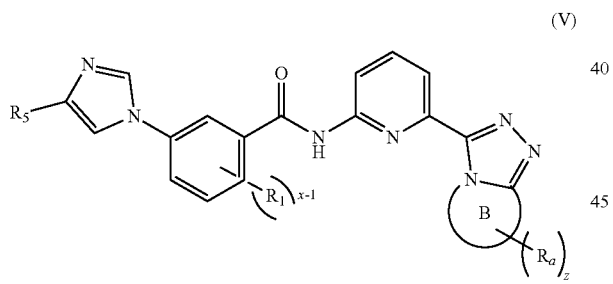

(V)

or a pharmaceutically acceptable salt or stereoisomer thereof.

7. The compound according to claim 6, wherein the compound is of formula (VI):

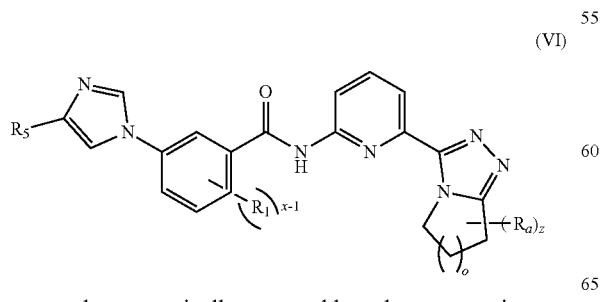

(VI)

or a pharmaceutically acceptable salt or stereoisomer thereof, wherein:
each $R_a$ is independently halogen, nitro, cyano, alkyl, deuterated alkyl, haloalkyl, —$(CH_2)_{1-5}OR_9$, —$(CR_9R_{10})_n$—, alkenyl, alkynyl, OH, O(alkyl), O(haloalkyl), cycloalkyl, heterocyclyl, aryl, or heteroaryl, wherein each alkyl, haloalkyl, alkenyl, alkynyl, cycloalkyl, heterocyclyl, aryl, and heteroaryl is optionally and independently substituted by one or more substituents independently selected from the group consisting of deuterium, halogen, nitro, cyano, alkyl, haloalkyl, hydroxyalkyl, —$(CH_2)_{1-5}OR_{12}$, alkenyl, alkynyl, $NH_2$, OH, O(deuterium), O(deuterated alkyl), O(haloalkyl), O(cycloalkyl), O(heterocyclyl), O(aryl), O(heteroaryl), cycloalkyl, heterocyclyl, aryl, and heteroaryl; and
is 1.

8. The compound according to claim 1, wherein the compound is of formula (VI-A):

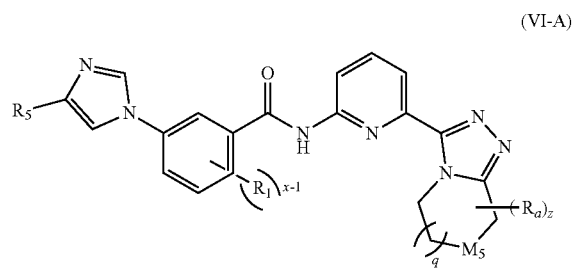

(VI-A)

or a pharmaceutically acceptable salt or stereoisomer thereof,
wherein:
$M_5$ is $CR_6$;
each $R_a$ is independently cyano, $C_{1-8}$ alkyl, $C_{1-8}$ haloalkyl, $C_{1-8}$ hydroxyalkyl, —$(CH_2)_{1-5}OR_9$, —$(CR_9R_{10})_n$—, $C_{2-8}$ alkenyl, $C_{2-8}$ alkynyl, —$(CH_2)_nC(O)R_9$, OH, $OC_{1-8}$ alkyl, $OC_{1-8}$ haloalkyl, $OC_{1-8}$ hydroxyalkyl, or $C_{3-8}$ cycloalkyl, wherein each $C_{1-8}$ alkyl, $C_{1-8}$ haloalkyl, $C_{2-8}$ alkenyl, $C_{2-8}$ alkynyl, $OC_{1-8}$ alkyl, and $C_{3-8}$ cycloalkyl is optionally and independently substituted by one or more substituents independently selected from the group consisting of deuterium, halogen, cyano, $C_{1-8}$ alkyl, $C_{1-8}$ hydroxyalkyl, OH, and $OC_{1-8}$ alkyl;
each $R_1$ is independently halogen or $C_{1-8}$ alkyl;
$R_5$ is $C_{1-8}$ alkyl, $C_{1-8}$ haloalkyl, $C_{1-8}$ hydroxyalkyl, $C_{3-8}$ cycloalkyl, or 3- to 6-membered heterocyclyl;
$R_6$ is hydrogen;
each $R_9$ is independently hydrogen, $C_{1-8}$ alkyl, $C_{1-8}$ haloalkyl, $C_{1-8}$ hydroxyalkyl, or $C_{1-8}$ alkoxy;
each $R_{10}$ is independently hydrogen, $C_{1-8}$ alkyl, $C_{1-8}$ haloalkyl, or $C_{1-8}$ hydroxyalkyl; and
q is 0.

9. The compound according to claim 1, wherein the compound is of formula (VII):

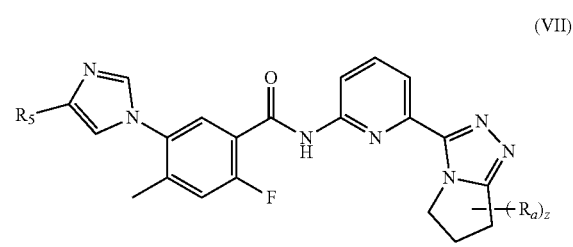

(VII)

or a pharmaceutically acceptable salt or stereoisomer thereof, wherein:

each $R_a$ is independently cyano, $C_{1-6}$ alkyl, $C_{1-6}$ haloalkyl, —(CH$_2$)$_{1-5}$OR$_9$, —(CR$_9$R$_{10}$)$_n$—, $C_{2-6}$ alkenyl, $C_{2-6}$ alkynyl, O($C_{1-6}$ alkyl), or $C_{3-6}$ cycloalkyl, wherein each $C_{1-6}$ alkyl, $C_{1-6}$ haloalkyl, $C_{2-6}$ alkenyl, $C_{2-6}$ alkynyl, and $C_{3-6}$ cycloalkyl is optionally and independently substituted by one or more substituents independently selected from the group consisting of halogen, cyano, $C_{1-6}$ alkyl, OH, and O($C_{1-6}$ alkyl).

10. The compound according to claim 1, or a stereoisomer thereof, wherein the compound, or stereoisomer thereof, is selected from the group consisting of:

8

9

10

11

12

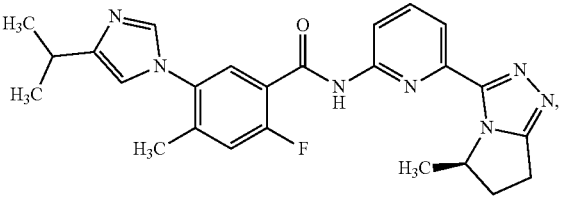

13

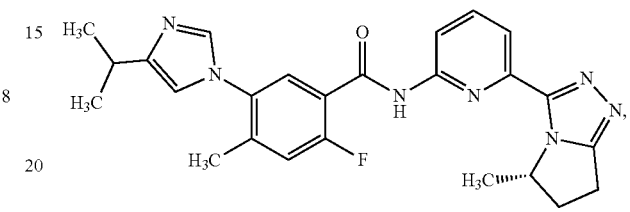

14, 15

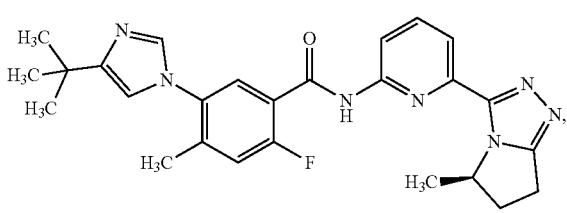

15, 16

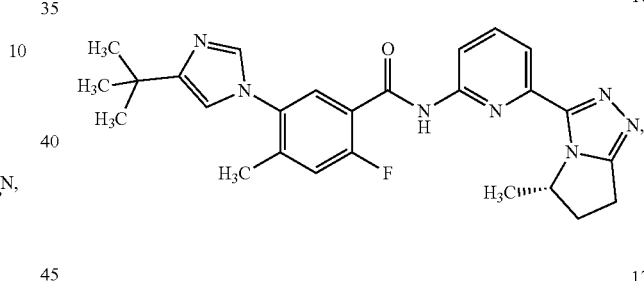

16, 17

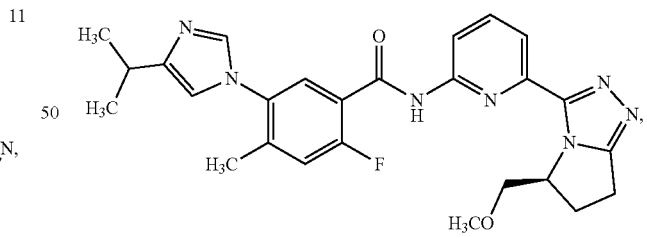

17, 18

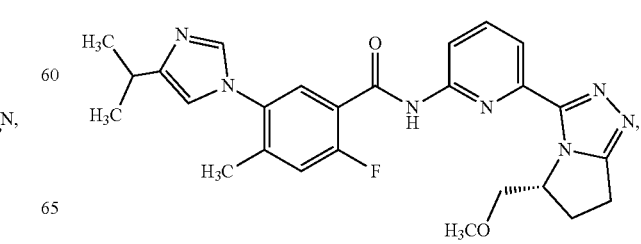

19
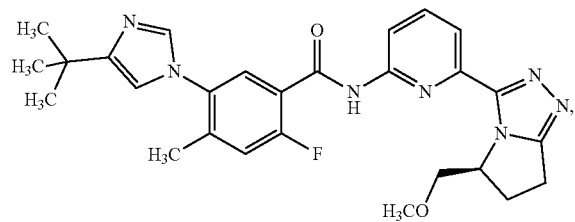
20
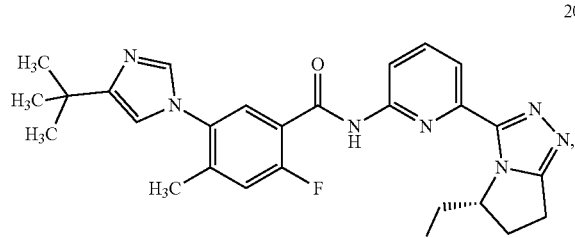
21
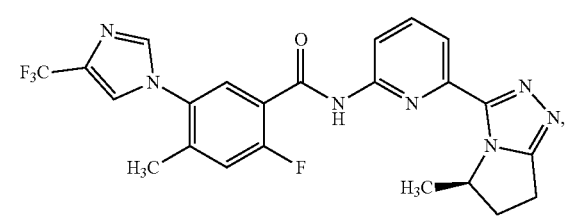
22
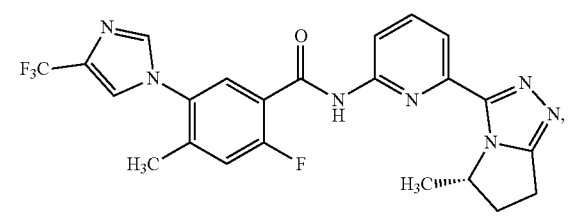
23
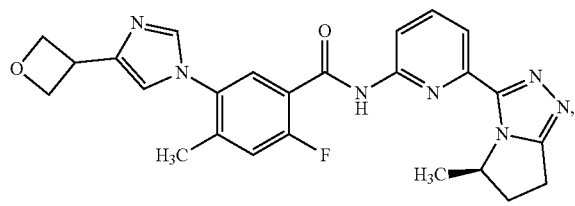
24
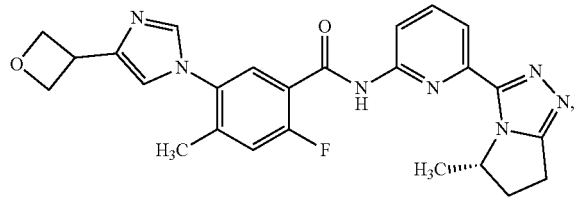
25
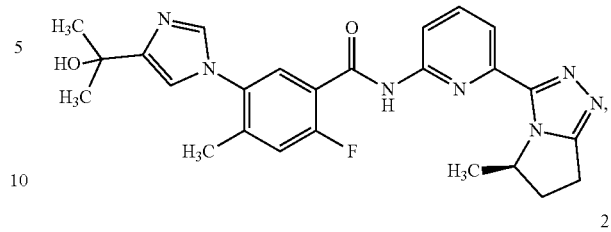
26
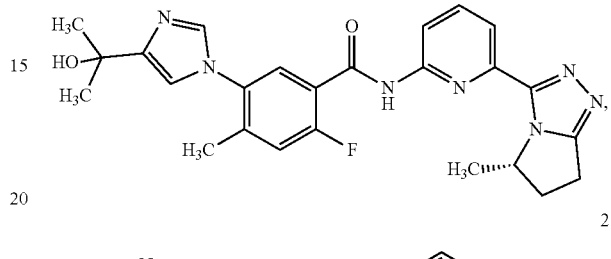
28
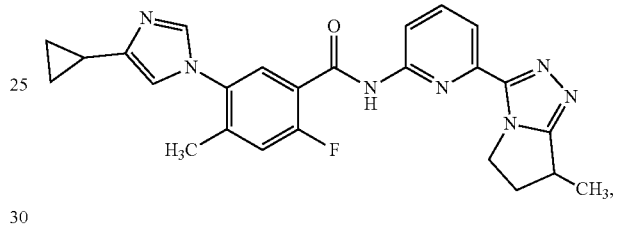
29
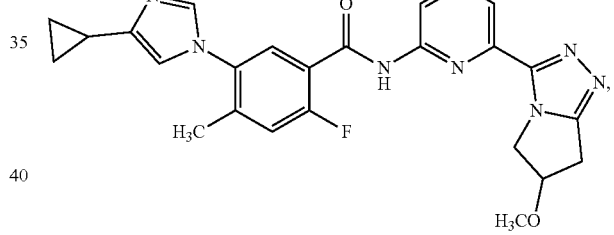
30
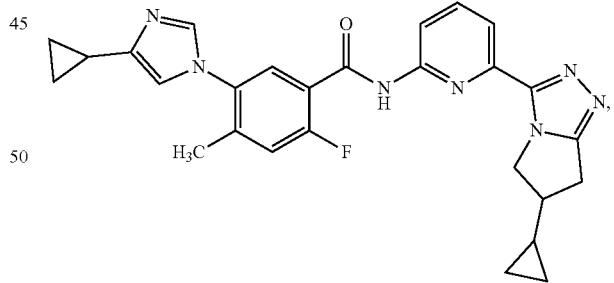
32
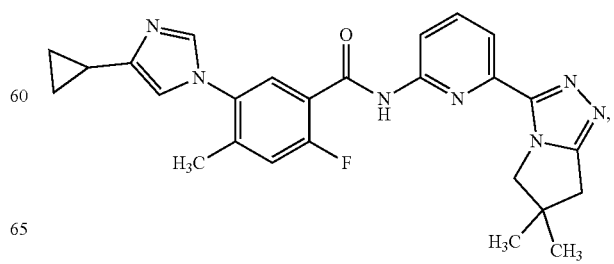

33
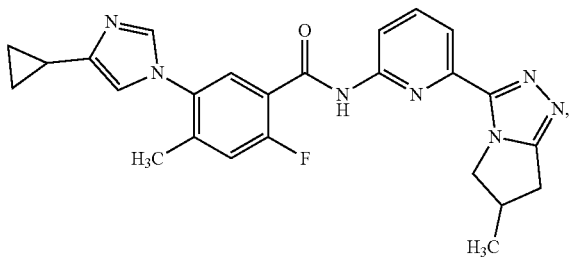
34
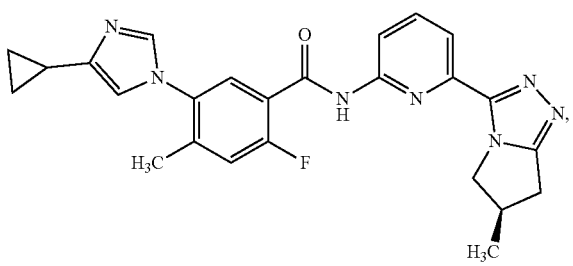
35
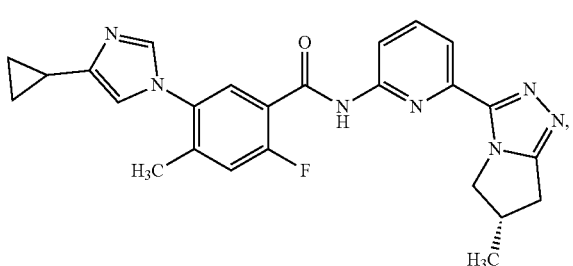
36
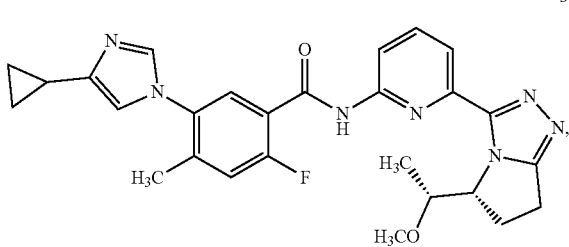
37
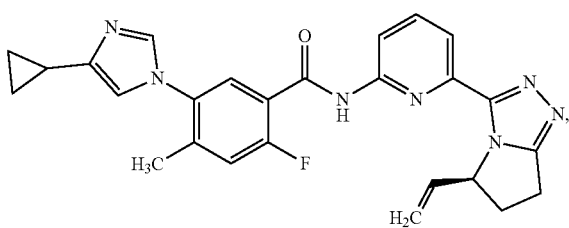
38
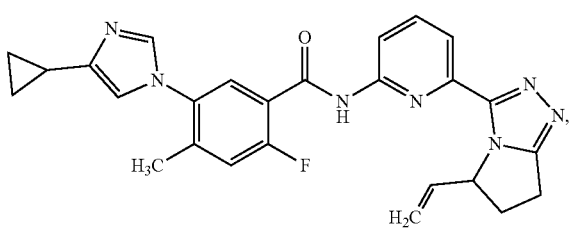
39
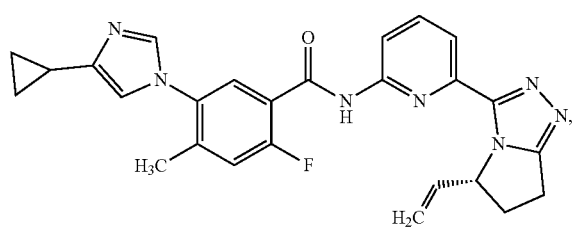
40
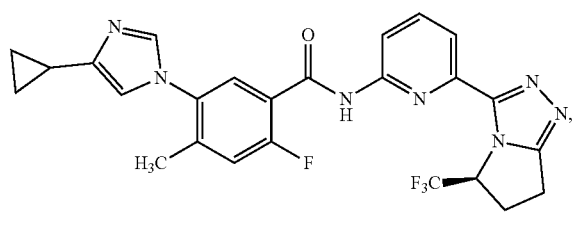
41
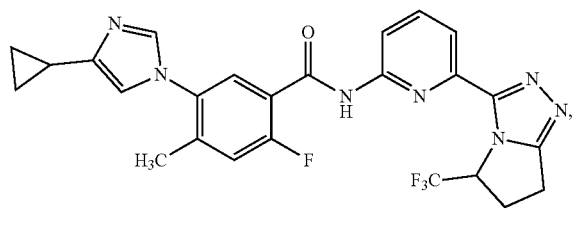
42
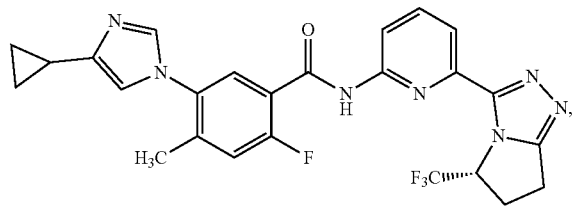
43
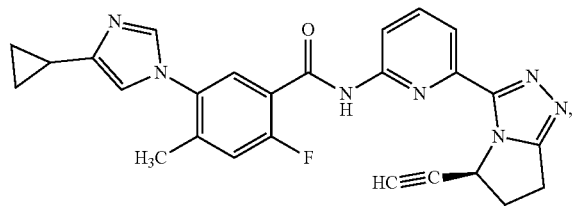
44
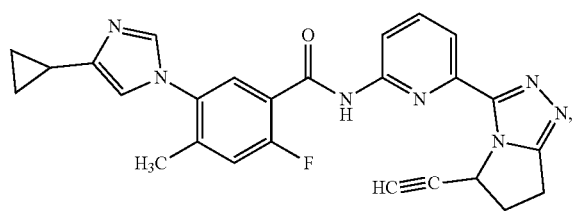

45
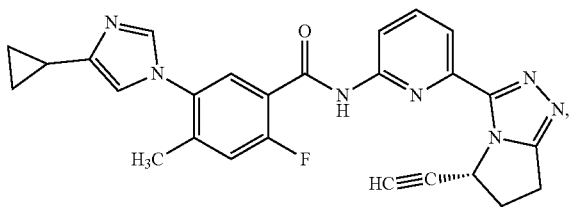
46
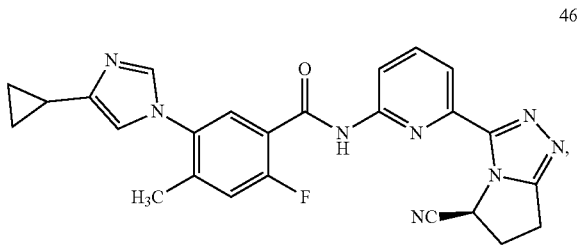
47
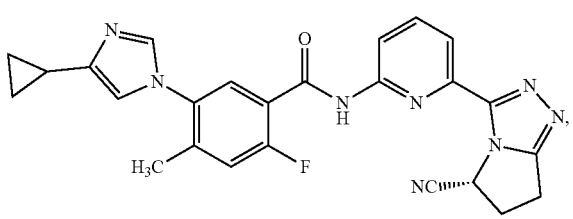
48
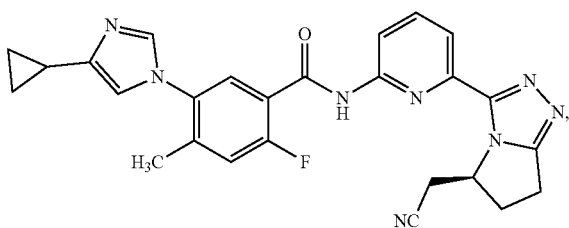
49
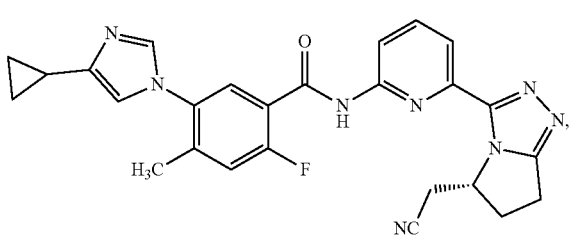
50
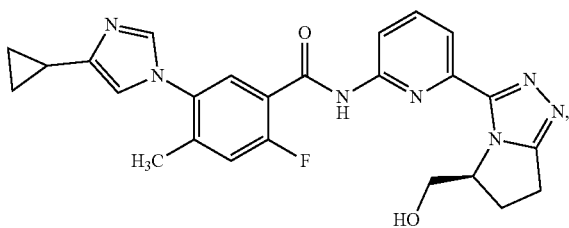
51
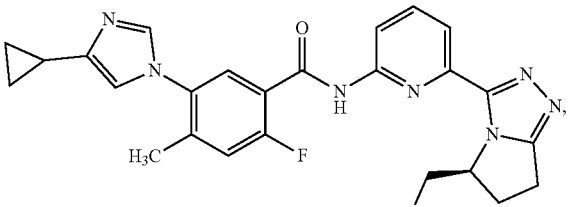
52
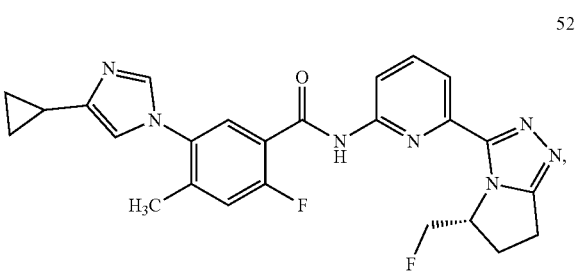
53
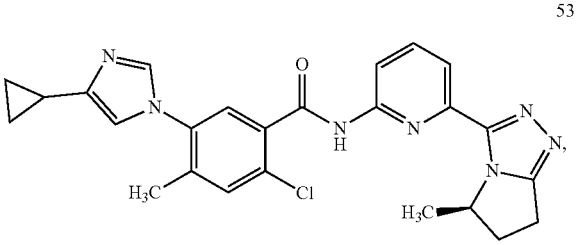
54
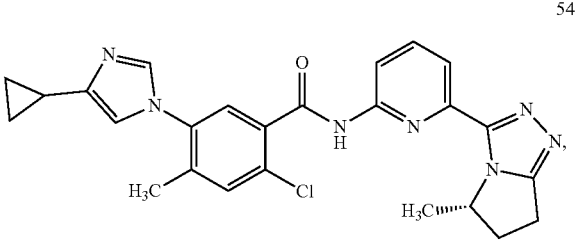
55
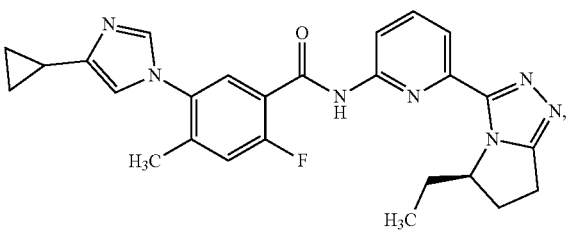
56
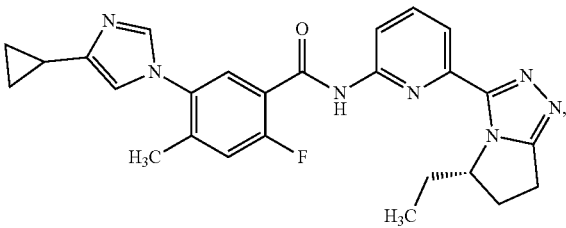

57

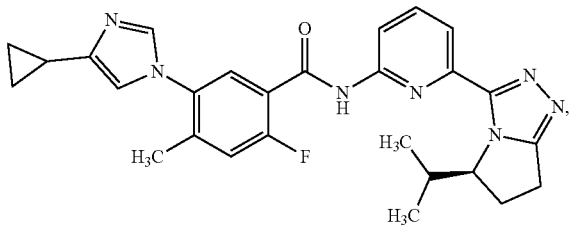

58

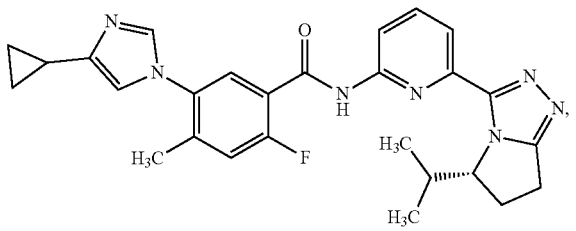

59

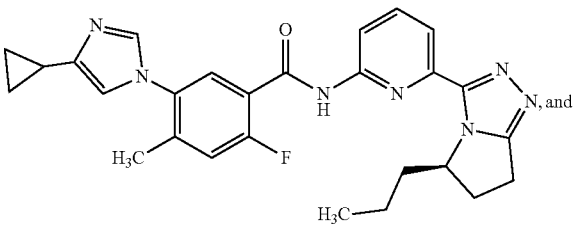

60

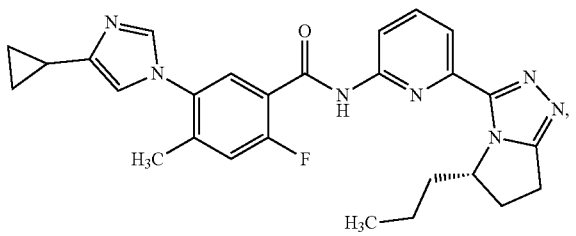

or a pharmaceutically acceptable salt thereof.

11. A pharmaceutical composition comprising one or more pharmaceutically acceptable carriers, diluents, or excipients and the compound according to claim 1, or a pharmaceutically acceptable salt or stereoisomer thereof.

12. A pharmaceutical composition comprising one or more pharmaceutically acceptable carriers, diluents, or excipients and the compound, or stereoisomer thereof, according to claim 10, or a pharmaceutically acceptable salt thereof.

13. A method for inhibiting apoptosis signal regulating kinase 1 activity in a subject in need thereof, comprising administering to the subject the pharmaceutical composition according to claim 11.

14. A method for inhibiting apoptosis signal regulating kinase 1 activity in a subject in need thereof, comprising administering to the subject the pharmaceutical composition according to claim 12.

15. A method for treating a neurodegenerative disorder, cardiovascular disorder, inflammatory disorder, or metabolic disorder in a subject in need thereof, comprising administering to the subject the pharmaceutical composition according to claim 11.

16. The method according to claim 15, wherein the inflammatory disorder is non-alcoholic steatohepatitis.

17. A method for treating a neurodegenerative disorder, cardiovascular disorder, inflammatory disorder, or metabolic disorder in a subject in need thereof, comprising administering to the subject the pharmaceutical composition according to claim 12.

18. The method according to claim 17, wherein the inflammatory disorder is non-alcoholic steatohepatitis.

* * * * *